(12) United States Patent
Hyde et al.

(10) Patent No.: US 10,010,704 B2
(45) Date of Patent: Jul. 3, 2018

(54) SYSTEMS, METHODS, AND DEVICES FOR DELIVERING TREATMENT TO A SKIN SURFACE

(71) Applicant: Elwha LLC, Bellevue, WA (US)

(72) Inventors: Roderick A. Hyde, Redmond, WA (US); Gary L. McKnight, Bothell, WA (US)

(73) Assignee: Elwha LLC, Bellevue, WA (US)

( * ) Notice: Subject to any disclaimer, the term of this patent is extended or adjusted under 35 U.S.C. 154(b) by 858 days.

(21) Appl. No.: 14/192,613

(22) Filed: Feb. 27, 2014

(65) Prior Publication Data

US 2015/0057622 A1 Feb. 26, 2015

Related U.S. Application Data

(63) Continuation-in-part of application No. 13/975,055, filed on Aug. 23, 2013, now Pat. No. 9,390,312, and
(Continued)

(51) Int. Cl.
*A61M 35/00* (2006.01)
*G06F 17/30* (2006.01)

(52) U.S. Cl.
CPC ....... *A61M 35/00* (2013.01); *G06F 17/30477* (2013.01)

(58) Field of Classification Search
CPC ..... A61B 5/00; G06F 17/30477; A61M 35/00
See application file for complete search history.

(56) References Cited

U.S. PATENT DOCUMENTS 4,384,288 A 5/1983 Walton
4,446,233 A 5/1984 Auditore-Hargreaves et al.
(Continued)

FOREIGN PATENT DOCUMENTS

JP 2002-284618 A 10/2002
WO WO 2008/086596 A1 7/2008
(Continued)

OTHER PUBLICATIONS

Ozalp et al.; "Antimicrobial aptamers for detection and inhibition of microbial pathogen growth"; Future Microbiology; Mar. 2013; pp. 387-401; vol. 8, No. 3; 1 page.
(Continued)

*Primary Examiner* — Amanda Lauritzen Moher
*Assistant Examiner* — Lisa Kinnard

(57) ABSTRACT

Systems, methods, and devices are described for delivering treatment to a skin surface of an individual based on a microbe profile, which include a skin-treatment delivery device including at least one treatment agent reservoir with at least one port with a controllable valve, at least one conduit, a location-capture component, a data storage component to store information associated with the microbe profile, and a computing component including a processor and circuitry to receive information associated with a measured feature of a location on the skin surface, correlate the received information associated with the measured feature of the location on the skin surface with the stored information associated with the microbe profile, select one or more treatment agents for application to the location on the skin surface from a database of treatment agents, and actuate the controllable valve of the at least one treatment agent reservoir to modulate release of the selected one or more treatment agents.

43 Claims, 26 Drawing Sheets

Related U.S. Application Data a continuation-in-part of application No. 14/091,762, filed on Nov. 27, 2013, now Pat. No. 9,526,480, and a continuation-in-part of application No. 14/091,832, filed on Nov. 27, 2013, now Pat. No. 9,549,703.

(56) References Cited

U.S. PATENT DOCUMENTS

| | | | |
|---|---|---|---|
| 5,077,210 A | | 12/1991 | Eigler et al. |
| 5,299,121 A | | 3/1994 | Brill et al. |
| 5,464,013 A | * | 11/1995 | Lemelson .......... A61K 41/0095 |
| | | | 128/925 |
| 5,544,651 A | * | 8/1996 | Wilk .................. A61B 5/14532 |
| | | | 600/310 |
| 5,728,028 A | | 3/1998 | Dusch |
| 5,747,022 A | | 5/1998 | Slavtcheff |
| 6,106,457 A | | 8/2000 | Perkins et al. |
| 6,199,557 B1 | | 3/2001 | Laughlin |
| 6,255,461 B1 | | 7/2001 | Mosbach et al. |
| 6,291,234 B1 | | 9/2001 | Raz et al. |
| 6,371,370 B2 | | 4/2002 | Sadler et al. |
| 6,379,920 B1 | | 4/2002 | El-Sayed et al. |
| 6,433,244 B1 | | 8/2002 | Roe et al. |
| 6,782,307 B2 | | 8/2004 | Wilmott et al. |
| 6,797,522 B1 | | 9/2004 | Still et al. |
| 6,802,811 B1 | | 10/2004 | Slepian |
| 6,905,692 B2 | | 6/2005 | Farmer |
| 6,961,517 B2 | | 11/2005 | Merola et al. |
| 7,070,590 B1 | | 7/2006 | Santini, Jr. et al. |
| 7,215,976 B2 | | 5/2007 | Brideglall |
| 7,303,875 B1 | | 12/2007 | Bock et al. |
| 7,314,453 B2 | | 1/2008 | Kuo |
| 7,319,038 B2 | | 1/2008 | Southard |
| 7,386,333 B1 | | 6/2008 | Birecki et al. |
| 7,413,567 B2 | | 8/2008 | Weckwerth et al. |
| 7,494,465 B2 | | 2/2009 | Brister et al. |
| 7,507,402 B1 | | 3/2009 | Farmer et al. |
| 7,931,592 B2 | | 4/2011 | Currie et al. |
| 8,028,708 B2 | | 10/2011 | Molema et al. |
| 8,041,147 B2 | | 10/2011 | Molnar et al. |
| 8,109,875 B2 | | 2/2012 | Gizewski |
| 8,260,010 B2 | | 9/2012 | Chhibber et al. |
| 8,358,348 B2 | | 1/2013 | Mohammadi et al. |
| 8,385,619 B2 | | 2/2013 | Soenksen |
| 8,475,789 B2 | | 7/2013 | Bisgaard-Frantzen |
| 8,557,560 B2 | | 10/2013 | Martin Jiménez et al. |
| 8,620,451 B2 | * | 12/2013 | Kennedy .............. A61N 5/0616 |
| | | | 607/101 |
| 9,028,846 B2 | | 5/2015 | Eddy |
| 9,186,278 B2 | | 11/2015 | Baym et al. |
| 9,289,140 B2 | * | 3/2016 | Ross ...................... A61B 5/026 |
| 2003/0007942 A1 | | 1/2003 | Koenig |
| 2003/0108896 A1 | | 6/2003 | Vogt |
| 2003/0173525 A1 | | 9/2003 | Seville |
| 2003/0225362 A1 | | 12/2003 | Currie et al. |
| 2004/0013828 A1 | | 1/2004 | Tewes-Schwarzer |
| 2004/0078219 A1 | | 4/2004 | Kaylor et al. |
| 2004/0111035 A1 | | 6/2004 | Kondoh et al. |
| 2004/0125996 A1 | | 7/2004 | Eddowes et al. |
| 2004/0202685 A1 | | 10/2004 | Manzo |
| 2004/0223985 A1 | | 11/2004 | Dunfield et al. |
| 2005/0019291 A1 | | 1/2005 | Zolotarsky et al. |
| 2005/0021173 A1 | | 1/2005 | Pinney et al. |
| 2005/0142093 A1 | | 6/2005 | Skover et al. |
| 2005/0154381 A1 | * | 7/2005 | Altshuler .............. A61B 18/203 |
| | | | 606/9 |
| 2005/0154382 A1 | | 7/2005 | Altshuler et al. |
| 2005/0171434 A1 | | 8/2005 | Madden et al. |
| 2005/0197652 A1 | | 9/2005 | Nat |
| 2006/0037197 A1 | | 2/2006 | Hawes et al. |
| 2006/0048278 A1 | | 3/2006 | Pitsolis |
| 2006/0052739 A1 | | 3/2006 | Henley et al. |
| 2006/0111620 A1 | | 5/2006 | Squilla et al. |
| 2006/0172318 A1 | | 8/2006 | Medinz et al. |
| 2006/0257993 A1 | | 11/2006 | McDevitt et al. |
| 2007/0016430 A1 | | 1/2007 | Goustova |
| 2007/0031028 A1 | | 2/2007 | Vetter et al. |
| 2007/0035815 A1 | * | 2/2007 | Edgar ................... A61B 5/0064 |
| | | | 359/359 |
| 2007/0059736 A1 | * | 3/2007 | Saito ................ B01L 3/502715 |
| | | | 435/6.13 |
| 2007/0128589 A1 | | 6/2007 | Sanders et al. |
| 2007/0134337 A1 | | 6/2007 | Villanueva et al. |
| 2007/0134649 A1 | | 6/2007 | Kolari et al. |
| 2008/0060148 A1 | | 3/2008 | Pinyayev et al. |
| 2008/0139974 A1 | | 6/2008 | Da Silva |
| 2008/0262321 A1 | | 10/2008 | Erad et al. |
| 2008/0262576 A1 | | 10/2008 | Creamer et al. |
| 2009/0001012 A1 | | 1/2009 | Kepner et al. |
| 2009/0041727 A1 | | 2/2009 | Suzuki et al. |
| 2009/0177639 A1 | | 7/2009 | Zerdoun |
| 2009/0186342 A1 | | 7/2009 | Bruno et al. |
| 2009/0202045 A1 | * | 8/2009 | Guertin .................... A61N 5/10 |
| | | | 378/195 |
| 2009/0286263 A1 | | 11/2009 | Graham et al. |
| 2010/0055161 A1 | | 3/2010 | Ahn |
| 2010/0063565 A1 | * | 3/2010 | Beerwerth ............ A61B 18/203 |
| | | | 607/88 |
| 2010/0068247 A1 | * | 3/2010 | Mou ...................... A45D 44/002 |
| | | | 424/443 |
| 2010/0074872 A1 | | 3/2010 | Blaser et al. |
| 2010/0185064 A1 | | 7/2010 | Bandic et al. |
| 2010/0204802 A1 | | 8/2010 | Wilson et al. |
| 2010/0239625 A1 | | 9/2010 | Puckett et al. |
| 2010/0292964 A1 | | 11/2010 | Tam et al. |
| 2010/0331641 A1 | | 12/2010 | Bangera et al. |
| 2011/0035898 A1 | | 2/2011 | Marek et al. |
| 2011/0040571 A1 | | 2/2011 | Warren |
| 2011/0117025 A1 | | 5/2011 | Dacosta et al. |
| 2011/0172591 A1 | * | 7/2011 | Babaev .................... A61M 35/00 |
| | | | 604/24 |
| 2011/0212485 A1 | | 9/2011 | Mitragotri et al. |
| 2011/0245094 A1 | | 10/2011 | Washburn et al. |
| 2011/0274676 A1 | | 11/2011 | Farmer et al. |
| 2011/0300196 A1 | | 12/2011 | Mohammadi et al. |
| 2012/0017929 A1 | * | 1/2012 | Samain ................ A61K 8/4986 |
| | | | 132/200 |
| 2012/0058464 A1 | | 3/2012 | Ermantraut et al. |
| 2012/0065086 A1 | | 3/2012 | Benson |
| 2012/0092461 A1 | | 4/2012 | Fisker et al. |
| 2012/0171193 A1 | | 7/2012 | Blaser et al. |
| 2012/0192884 A1 | | 8/2012 | Nasu et al. |
| 2012/0241391 A1 | | 9/2012 | Carlson et al. |
| 2012/0253224 A1 | | 10/2012 | Mir et al. |
| 2013/0057866 A1 | * | 3/2013 | Hillebrand ........... A45D 44/005 |
| | | | 356/421 |
| 2013/0078298 A1 | | 3/2013 | Av-Gay et al. |
| 2013/0079605 A1 | | 3/2013 | Bandaru et al. |
| 2013/0084259 A1 | | 4/2013 | Lee |
| 2013/0115317 A1 | | 5/2013 | Charbonneau et al. |
| 2013/0115610 A1 | | 5/2013 | Lanzalaco et al. |
| 2013/0178791 A1 | | 7/2013 | Javitt |
| 2013/0217947 A1 | * | 8/2013 | Fishman ................ A61B 8/085 |
| | | | 600/1 |
| 2013/0218024 A1 | | 8/2013 | Boctor et al. |
| 2013/0224155 A1 | | 8/2013 | Kaplan et al. |
| 2013/0244977 A1 | | 9/2013 | Lee et al. |
| 2013/0317741 A1 | | 11/2013 | Brashear et al. |
| 2013/0338039 A1 | | 12/2013 | Mazed et al. |
| 2014/0037688 A1 | | 2/2014 | Berkes et al. |
| 2014/0271964 A1 | | 9/2014 | Roberts, IV et al. |
| 2014/0309662 A1 | | 10/2014 | Brewer et al. |
| 2015/0054944 A1 | | 2/2015 | Bangera et al. |
| 2015/0054945 A1 | | 2/2015 | Bangera et al. |
| 2015/0148684 A1 | | 5/2015 | Baym et al. |
| 2015/0148685 A1 | | 5/2015 | Baym et al. |
| 2015/0339513 A1 | | 11/2015 | Bolea |
| 2016/0032365 A1 | | 2/2016 | Maitra et al. |

FOREIGN PATENT DOCUMENTS

| WO | WO 2010/093503 A2 | 8/2010 |
|---|---|---|
| WO | WO 2011/103144 A1 | 8/2011 |

(56) References Cited

FOREIGN PATENT DOCUMENTS

| WO | WO 2012/044794 A2 | 4/2012 |
|---|---|---|
| WO | WO 2013/012924 A2 | 1/2013 |
| WO | WO 2013/070893 A1 | 5/2013 |

OTHER PUBLICATIONS

"Antibody Mimetic"; Wikipedia; Feb. 6, 2011; pp. 1-2; located at: http://en.wikipedia.org/wiki/Antibody_mimetic.
Adak et al.; "Bishydrazide Glycoconjugates for Lectin Recognition and Capture of Bacterial Pathogens"; Bioconjug Chem; Nov. 17, 2010; pp. 1-27; vol. 21; No. 11.
Alexander et al.; "Molecular imprinting science and technology: a survey of the literature for the years up to and including 2003"; Journal of Molecular Recognition; Jan. 4, 2006; pp. 106-180; vol. 19; John Wiley & Sons, Ltd.
Ammor, Mohammed Salim; "Recent Advances in the Use of Intrinsic Fluorescence for Bacterial Identification and Characterization"; J Fluoresc; Mar. 12, 2007; pp. 1-5; Springer Science + Business Media, LLC.
Baddour et al.; "High Frequency Ultrasound Imaging of Changes in Cell Structure Including Apoptosis"; PDF created on Aug. 12, 2013; pp. 1-6; IEEE.
Barlen et al.; "Detection of *Salmonella* by Surface Plasmon Resonance"; Sensors; Aug. 7, 2007; pp. 1427-1446; vol. 7; MDPI.
Bernardini et al.; "The 3D Model Acquisition Pipeline"; Computer Graphics Forum; 2002; pp. 149-172; vol. 21; No. 2; The Eurographics Association and Blackwell Publishers Ltd.
Bhatta et al.; "Use of Fluorescence Spectroscopy to Differentiate Yeast and Bacterial Cells"; Applied Microbiology and Biotechnology; 2006; pp. 121-126; vol. 71; No. 1.
Blank et al.; "A force-based protein biochip"; PNAS; Sep. 30, 2003; pp. 11356-11360; vol. 100; No. 20; The National Academy of Sciences of the USA.
Bouchard et al.; "Optical characterization of Pseudomonas fluorescens on meat surfaces using time-resolved fluorescence"; Journal of Biomedical Optics; Jan./Feb. 2006; pp. 014011-1-014011-7; vol. 11; No. 1.
Brennan, John D.; "Preparation and Entrapment of Fluorescently Labeled Proteins for the Development of Reagentless Optical Biosensors"; Journal of Fluorescence; Apr. 28, 1999; pp. 295-312; vol. 9; No. 4; Plenum Publishing Corporation.
Bright et al.; "Regenerable Fiber-Optic-Based Immunosensor"; Analytical Chemistry; May 15, 1990; pp. 1065-1069; vol. 62, No. 10; American Chemical Society.
Cady et al.; "Optimized linkage and quenching strategies for quantum dot molecular beacons"; Molecular and Cellular Probes; PDF created on Aug. 19, 2013; pp. 116-124; vol. 21; Elsevier Ltd.
Cao et al.; "Molecular Beacon Aptamers for Protein Monitoring in Real-Time and in Homogeneous Solutions"; Current Proteomics; PDF created on Aug. 19, 2013; pp. 31-40; vol. 2; Bentham Science Publishers Ltd.
Chen et al.; "Aptamer from whole-bacterium SELEX as new therapeutic reagent against virulent Mycobacterium tuberculosis"; Biochemical and Biophysical Research Communications; Apr. 11, 2007; pp. 743-748; vol. 357; Elsevier Inc.
Chung et al.; "Size Comparisons among Integral Membrane Transport Protein Homologues in Bacteria, Archaea, and Eucarya"; Journal of Bacteriology; Feb. 2001; pp. 1012-1021; vol. 183; No. 3; American Society for Microbiology.
Cockburn et al.; "High throughput DNA sequencing to detect differences in the subgingival plaque microbiome in elderly subjects with and without dementia"; Investigative Genetics; PDF created Aug. 16, 2013; pp. 1-12; vol. 3; No. 19; Cockburn et al, Biomed Central Ltd.
Cole et al.; "The Ribosomal Database Project: improved alignments and new tools for rRNA analysis"; Nucleic Acids Research; published online Nov. 12, 2008; pp. D141-D145; vol. 37; The Author(s).

Cowan et al.; "Development of engineered biofilms on poly-L-lysine patterned surfaces"; Biotechnology Letters; Accepted May 23, 2001; pp. 1235-1241; vol. 23; Kluwer Academic Publishers; Netherlands.
Crawford et al.; "Peptide aptamers: Tools for biology and drug discovery"; Briefings in Functional Genomics and Proteomics; Apr. 2003; pp. 72-79; vol. 2; No. 1; Henry Stewart Publications.
Crowe et al.; "Candida albicans binds human plasminogen: identification of eight plasminogen-binding proteins"; Molecular Microbiology; PDF created Aug. 16, 2013; pp. 1637-1651; vol. 47; No. 6; Blackwell Publishing Ltd.
De Château et al.; "Protein PAB, an Albumin-binding Bacterial Surface Protein Promoting Growth and Virulence"; The Journal of Biological Chemistry; revised Jul. 22, 1996; pp. 26609-26615; vol. 271; No. 43; Issue of Oct. 25, 1996; The American Society for Biochemistry and Molecular Biology, Inc.; USA.
Dewhirst et al.; "The Human Oral Microbiome"; Journal of Bacteriology; Accepted Jul. 10, 2010; pp. 5002-5017; vol. 192; No. 19; American Society for Microbiology.
Didenko et al.; "Horseradish peroxidase-driven fluorescent labeling of nanotubes with quantum dots"; Biotechniques; NIH Public Access Author Manuscript; Mar. 2006; pp. 295-302; vol. 40; No. 3.
Doornbos et al.; "White Blood Cell Differentiation Using a Solid State Flow Cytometer"; Cytometry; accepted Mar. 16, 1993; pp. 589-594; vol. 14; Wiley-Liss, Inc.
Dwarakanath et al.; "Quantum dot-antibody and aptamer conjugates shift fluorescence upon binding bacteria"; Biochemical and Biophysical Research Communications; Received Oct. 11, 2004; pp. 739-743; vol. 325; Elsevier Inc.
Elston, Dirk M.; "Fluorescence of fungi in superficial and deep fungal infections"; BMC Microbiology; Sep. 24, 2001; pp. 1-4; vol. 1; No. 21; Elston.
Fan et al.; "Sensitive optical biosensors for unlabeled targets: A review"; Analytica Chimica Acta; PDF created Aug. 12, 2013; pp. 8-26; vol. 620; Elsevier B.V.
Fan et al.; "Structures in Bacillus subtilis Are Recognized by CD14 in a Lipopolysaccharide Binding Protein-Dependent Reaction"; Infection and Immunity; Jun. 1999; pp. 2964-2968; vol. 67; No. 6; American Society for Microbiology.
Fei-Fei et al.; "One-Shot Learning of Object Categories"; IEEE Transactions on Pattern Analysis and Machine Intelligence; Apr. 2006; pp. 594-611; vol. 28; No. 4; IEEE Computer Society.
Feng et al.; "Computer-assisted technique for the design and manufacture of realistic facial prostheses"; British Journal of Oral and Maxillofacial Surgery; PDF created on Aug. 12, 2013; pp. 105-109; vol. 48; The British Association of Oral and Maxillofacial Surgeons.
Freeman et al.; "Chemiluminescent and Chemiluminescence Resonance Energy Transfer (CRET) Detection of DNA, Metal Ions, and Aptamer—Substrate Complexes Using Hemin/G-Quadruplexes and CdSe/ZnS Quantum Dots"; Journal of the American Chemical Society; PDF created on Aug. 19, 2013; pp. 11597-11604; vol. 133; American Chemical Society.
Gaitanis et al.; "The *Malassezia* Genus in Skin and Systemic Diseases"; Clinical Microbiology Reviews; Jan. 2012; pp. 106-141; vol. 25; No. 1; American Society for Microbiology.
Gao et al.; "A Micro Sensing Probe for Detecting Individual Biological Cells"; Proceedings of the 25th Annual International Conference of the IEEE EMBS, Cancun, Mexico; Sep. 17-21, 2003; pp. 3348-3351; IEEE.
Gauglitz et al.; "Host Defence Against Candida albicans and the Role of Pattern-recognition Receptors"; Acta Derm Venereol; 2012; pp. 291-298; vol. 92; The Authors; Journal Compilation: Acta Dermato-Venereologica.
Giana et al.; "Rapid Identification of Bacterial Species by Fluorescence Spectroscopy and Classification Through Principal Components Analysis"; Journal of Fluorescence; Nov. 2003; pp. 489-493; vol. 13, No. 6; Plenum Publishing Corporation.
Gopinath et al.; "Aptamer That Binds to the gD Protein of Herpes Simplex Virus 1 and Efficiently Inhibits Viral Entry"; Journal of Virology; Jun. 2012; pp. 6732-6744; vol. 86; No. 12; American Society for Microbiology.

(56) References Cited

OTHER PUBLICATIONS

Graham, Anna R.; "Fungal Autofluorescence with Ultraviolet Illumination"; American Journal of Clinical Pathology; Feb. 1983; pp. 231-234; vol. 79; No. 2; American Society of Clinical Pathologists.

Grice et al.; "A diversity profile of the human skin microbiota"; Genome Research; PDF created on Aug. 12, 2013; pp. 1043-1050; vol. 18; Cold Spring Harbor Laboratory Press.

Grice et al.; "The skin microbiome"; Nature Reviews—Microbiology; Apr. 2011; pp. 244-253; vol. 9; Macmillan Publishers Limited.

Griffen et al.; "CORE: A Phylogenetically-Curated 16S rDNA Database of the Core Oral Microbiome"; PLoS One; Apr. 2011; pp. 1-10; vol. 6; Issue 4; Griffen et al.

Hagleitner et al.; "Smart single-chip gas sensor microsystem"; Nature; Nov. 15, 2001; pp. 293-296; vol. 414; Macmillan Magazines Ltd.

Harz et al.; "Vibrational Spectroscopy—A Powerful Tool for the Rapid Identification of Microbial Cells at the Single-Cell Level"; Cytometry Part A Journal of the International Society for Advancement of Cytometry; PDF created on Aug. 12, 2013; pp. 104-113; vol. 75A; International Society for Advancement of Cytometry.

Helm et al.; "Classification and identification of bacteria by Fourier-transform infrared spectroscopy"; Journal of General Microbiology; 1991; pp. 69-79; vol. 137; SGM; Printed in Great Britain.

Hildebrand et al.; "Acoustic microscopy of living cells"; Proc. Natl. Acad. Sci.; Mar. 1981; pp. 1656-1660; vol. 78; No. 3.

Hilton, Peter J.; "Laser induced fluorescence imaging of bacteria"; SPIE; PDF created on Aug. 12, 2013; pp. 1174-1178; vol. 3491.

Hornyak, Tim; "RFID Powder"; Scientific American; Feb. 2008; pp. 68-71; Scientific American, Inc.

Huff et al.; "Light-scattering sensor for real-time identification of Vibrio parahaemolyticus, Vibrio vulnificus and Vibrio cholera colonies on solid agar plate"; Microbial Biotechnology; PDF created on Aug. 12, 2013; pp. 607-620; vol. 5, No. 5; The Authors; Microbial Biotechnology—Society for Applied Microbiology and Blackwell Publishing Ltd.

Ikanovic et al.; "Fluorescence Assay Based on Aptamer-Quantum Dot Binding to Bacillus Thuringiensis Spores"; J Fluoresc; 2007; pp. 193-199; vol. 17; Springer Science + Business Media, LLC.
Jaiswal et al.; "Long-term multiple color imaging of live cells using quantum dot bioconjugates"; Nature Biotechnology; Jan. 2003; pp. 47-51; vol. 21; Nature Publishing Group; www.nature.com/naturebiotechnology.
Jhaveri et al.; "In vitro selection of signaling aptamers"; Nature Biotechnology; Dec. 2000; pp. 1293-1297; vol. 18; Nature America Inc.
Kashyap et al.; "Surface Plasmon Resonance-Based Fiber and Planar Waveguide Sensors"; Journal of Sensors; Accepted Jun. 26, 2009; pp. 1-9; vol. 2009; Hindawi Publishing Corporation.
Kim et al.; "Lens-Free Imaging for Biological Applications"; Journal of Laboratory Automation; Jan. 27, 2012; pp. 43-49; vol. 17; No. 1; Society for Laboratory Automation and Screening.
Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.
Koenig et al.; "Laser-Induced Autofluorescence for Medical Diagnosis"; Journal of Fluorescence; 1994; pp. 17-40; vol. 4; No. 1; Plenum Publishing Corporation.
Koo et al.; "Development of a Streptavidin-Conjugated Single-Chain Antibody That Binds Bacillus cereus Spores"; Applied and Environmental Microbiology; Jul. 1998; pp. 2497-2502; vol. 64; No. 7; American Society for Microbiology.
Kumar et al.; "AnimalLectinDB: An integrated animal lectin database"; Bioinformation; published Apr. 22, 2011; pp. 134-136; vol. 6; No. 3; Biomedical Informatics.
Kupper et al.; "Generation of human antibody fragments against *Streptococcus* mutans using a phage display chain shuffling approach"; BMC Biotechnology; Jan. 25, 2005; pp. 1-12; vol. 5; No. 4; Kupper et al.
Lee et al.; "A micro-machined LC-resonator for high-frequency magnetic sensor applications"; Intermag 2006; Downloaded on Nov. 17, 2009; pp. 1.
Lee et al.; "Graphene-Based Chemiluminescence Resonance Energy Transfer for Homogeneous Immunoassay"; ACS NANO; 2012; pp. 2978-2983; vol. 6; No. 4; American Chemical Society.
Liu et al.; "Deep Sequencing of the Oral Microbiome Reveals Signatures of Periodontal Disease"; PLos One; Jun. 2012; pp. 1-16; vol. 7; Issue 6; Liu et al.
Low et al.; "A DNA Aptamer Recognizes the Asp f 1 Allergen of Aspergillus fumigatus"; Biochem Biophys Res Commun.; Aug. 28, 2009; pp. 544-548; vol. 386; No. 3; Elsevier Inc.
Majid et al.; "Integration of stereophotogrammetry and triangulation-based laser scanning system for precise mapping of craniofacial morphology"; The International Archives of the Photogrammetry, Remote Sensing and Spatial Information Sciences; PDF created on Aug. 12, 2013; pp. 805-812; vol. XXXVII; Part B5; Beijing.
Markiewicz et al.; "The Use of 3D Imaging Tools in Facial Plastic Surgery"; Facial Plast Surg Clin N Am; PDF created on Aug. 12, 2013; pp. 655-682; vol. 19; Elsevier Inc.
Martin et al.; "Learning to Detect Natural Image Boundaries Using Local Brightness, Color, and Texture Cues"; IEEE Transactions on Pattern Analysis and Machine Intelligence; May 2004; pp. 530-549; vol. 26; No. 5; IEEE Computer Society.
Mateus et al.; "Adherence of Candida albicans to Silicone Induces Immediate Enhanced Tolerance to Fluconazole"; Antimicrobial Agents and Chemotherapy; Sep. 2004; pp. 3358-3366; vol. 48; No. 9; American Society for Microbiology.
Meerwaldt et al.; "Skin Autofluorescence, a Measure of Cumulative Metabolic Stress and Advanced Glycation End Products, Predicts Mortality in Hemodialysis Patients"; Journal of the American Society of Nephrology; 2005; pp. 3687-3693; vol. 16; American Society of Nephrology.
Modlin, Robert L.; "Innate Immunity: Ignored for decades, but not forgotten"; J Invest Dermatol.; Mar. 2012; pp. 882-886; vol. 132; No. 3.
Mohan et al.; "Bokode: Imperceptible Visual tags for Camera Based Interaction from a Distance"; PDF created on Aug. 12, 2013; pp. 1-8; http://cameraculture.media.mit.edu/bokode.
Mohanty et al.; "Micro Electrical Impedance Spectroscopy of Bovine Chromaffin Cells"; printed on Nov. 14, 2013; pp. 1-5.
Murakami et al.; "A miniature confocal optical microscope with mems gimbal scanner"; Transducers '03; The 12th International Conference on Solid State Sensors, Actuators and Microsystems, Boston, Jun. 8-12, 2003; pp. 587-590; IEEE.
Nakatsuji et al.; "Antibodies Elicited by Inactivated Propionibacterium acnes-Based Vaccines Exert Protective Immunity and Attenuate the IL-8 Production in Human Sebocytes: Relevance to Therapy for Acne Vulgaris"; Journal of Investigative Dermatology; published online May 8, 2008; pp. 2451-2457; vol. 128; The Society for Investigative Dermatology.
Nitsche et al.; "One-step selection of Vaccinia virus-binding DNA aptamers by MonoLEX"; BMC Biotechnology; published Aug. 15, 2007; pp. 1-12; vol. 7; No. 48; Nitsche et al.
Oberreuter et al.; "Identification of coryneform bacteria and related taxa by Fourier-transform infrared (FT-IR) spectroscopy"; International Journal of Systematic and Evolutionary Microbiology; 2002; pp. 91-100; vol. 52; IUMS.
Peppas et al.; "Polymers and Gels as Molecular Recognition Agents"; Pharmaceutical Research; May 2002; pp. 578-587; vol. 19; No. 5; Plenum Publishing Corporation.
Proske et al.; "Aptamers—basic research, drug development, and clinical applications"; Appl Microbiol Biotechnol; Published online Nov. 11, 2005; pp. 367-374; vol. 69; Springer-Verlag.
Quast et al.; "The SILVA ribosomal RNA gene database project: improved data processing and web-based tools"; Nucleic Acids Research; Published Nov. 28, 2012; pp. D590-D596; vol. 41; The Author(s) 2012; Oxford University Press.
Raghavan et al.; "BIAcore: a microchip-based system for analyzing the formation of macromolecular complexes"; Structure; Apr. 15, 1995; pp. 351-333; vol. 3; No. 4; Current Biology Ltd.

(56) References Cited

OTHER PUBLICATIONS

Rucker et al.; "Functional Antibody Immobilization on 3-Dimensional Polymeric Surfaces Generated by Reactive Ion Etching"; Langmuir; In Final Form Jun. 2, 2005; pp. 7621-7625; vol. 21; American Chemical Society.

Seidl et al.; "Opto-mechanical combination of a line scanning camera and a micro laser scanner system"; PDF created on Aug. 12, 2013; pp. 1-6.

Selinummi et al.; "Software for quantification of labeled bacteria from digital microscope images by automated image analysis"; BioTechniques; Dec. 2005; pp. 859-863; vol. 39; No. 6.

Shimobaba et al.; "Gigapixel inline digital holographic microscopy using a consumer scanner"; Physics Optics; May 27, 2013; pp. 1-6; Optical Society of America.

Snow et al.; "Chemical Detection with a Single-Walled Carbon Nanotube Capacitor"; Science; Mar. 25, 2005; pp. 1942-1945; vol. 307; American Association for the Advancement of Science.

Son et al.; "An implantable wireless microdosimeter for radiation oncology"; MEMS 2008, Tucson, AZ, USA; Jan. 13-17, 2008; pp. 256-259; IEEE.

Spear et al.; "Isolation, characterization, and recovery of small peptide phage display epitopes selected against viable malignant glioma cells"; Cancer Gene Therapy; Received Mar. 5, 2001; pp. 506-511; vol. 8, No. 7; Nature Publishing Group.

Sun et al.; "An Enhanced Active Shape Model for Facial Features Extraction"; 2008 11th IEEE International Conference on Communication Technology Proceedings; 2008; pp. 661-664; IEEE.

Sun et al.; "Broadband single cell impedance spectroscopy using maximum length sequences: theoretical analysis and practical considerations"; Measurement Science and Technology; 2007; pp. 2589-2868; vol. 18; IOP Publishing Ltd, UK.

Tachon et al.; "Experimental conditions affect the site of tetrazolium violet reduction in the electron transport chain of Lactococcus lactis"; Microbiology; Accepted Jun. 7, 2009; pp. 2941-2948; vol. 155; SGM.

Terada et al.; "Bacterial adhesion to and viability on positively charged polymer surfaces"; Microbiology; Accepted on Aug. 22, 2006; pp. 3575-3583; vol. 152; SGM.

Ulicny, J.; "Lorenz-Mie Light Scattering in Cellular Biology"; Gen. Physiol. Biophys.; 1992; pp. 133-151; vol. 11.

Valm et al.; "Systems-level analysis of microbial community organization through combinatorial labeling and spectral imaging"; PNAS; Mar. 8, 2011; pp. 4152-4157; vol. 108; No. 10.

Van Heerbeek et al.; "Three dimensional measurement of rhinoplasty results"; Rhinology; 2009; pp. 121-125; vol. 47.

Vashist, Sandeep Kumar; "A Review of Microcantilevers for Sensing Applications"; AZojono Journal of Nanotechnology Online; Jun. 2007; pp. 1-15; vol. 3; AZoM.com Pty Ltd.

Yasuda et al.; "Lectin Microarray Reveals Binding Profiles of Lactobacillus casei Strains in a Comprehensive Analysis of Bacterial Cell Wall Polysaccharides"; Applied and Environmental Microbiology; Jul. 2011; pp. 4539-4546; vol. 77, No. 13; American Society for Microbiology.

Ye et al.; "Molecularly imprinted polymers as antibody and receptor mimics for assays, sensors and drug discovery"; Anal Bioanal Chem; Published online Jan. 22, 2004; pp. 1887-1897; vol. 378; Springer-Verlag.

Yusa et al.; "Controlled multiple quantum coherences of nuclear spins in a nanometre-scale device"; Nature; Apr. 21, 2005; pp. 1001-1005; vol. 434; Nature Publishing Group.

Zelada-Guillen et al.; "Immediate Detection of Living Bacteria at Ultralow Concentrations Using a Carbon Nanotube Based Potentiometric Aptasensor"; Angew. Chem. Int. Ed; 2009; pp. 1-4; vol. 48; Wiley-VCH Verlag GmbH & Co. KGaA; Weinheim.

Zharov et al.; "In vivo high-speed imaging of individual cells in fast blood flow"; Journal of Biomedical Optics; Sep./Oct. 2006; pp. 054034-1-054034-4; vol. 11; No. 5; SPIE.

Zharov et al.; "In vivo Photothermal Flow Cytometry: Imaging and Detection of Individual Cells in Blood and Lymph Flow"; Journal of Cellular Biochemistry; 2006; pp. 916-932; vol. 97; Wiley-Liss, Inc.

Zheng et al.; "Enhanced active shape model for facial feature localization"; Proceedings of the Seventh International Conference on Machine Learning and Cybernetics, Kunming; Jul. 12-15, 2008; pp. 2841-2845; IEEE.

PCT International Search Report; International App. No. PCT/US2014/052081; dated Nov. 20, 2014; pp. 1-8.

PCT International Search Report; International App. No. PCT/US2014/052077; dated Nov. 28, 2014; pp. 1-4.

PCT International Search Report; International App. No. PCT/US2014/052086; dated Nov. 28, 2014; pp. 1-3.

PCT International Search Report; International App. No. PCT/US2014/051928; dated Dec. 1, 2014; pp. 1-3.

PCT International Search Report; International App. No. PCT/US2014/051934; dated Dec. 1, 2014; pp. 1-3.

Bateni et al.; The Use of Konjac Glucomannan Hydrolysates (GMH) to Improve the Health of the Skin and Reduce Acne Vulgaris; American Journal of Dermatology and Venereology; pp. 10-14; bearing a date of 2013; Scientific & Academic Publishing.

Buckley et al.; A Three-Dimensional Morphometric Study of Craniofacial Shape in Schizophrenia; Am J Psychiatry; Mar. 2005; pp. 606-608.

Chawla et al.; Applications & Practice—An Overview of Passive RFID; IEEE Applications & Practice; Sep. 2007; pp. 11-17.

Cho et al.; The Human Microbiome: at the interface of health and disease; National Institute of Health; bearing a date of Oct. 1, 2012; pp. 1-28; Nat. Rev. Genet.

Finkenzeller, Klaus; Fundamental Operating Principles; RFID Handbook: Fundamentals and Applications in Contactless Smart Cards and Identification; bearing a date of 2013; pp. 29-59; John Wiley & Sons, Ltd.

Grice et al.; The skin microbiome; Nature.com; Apr. 2011; pp. 244-253; vol. 9; Macmillan Publishers Limited.

Gueniche et al.; *Bifidobacterium longum* lysate, a new ingredient for reactive skin; Experimental Dermatology; bearing a date of Jun. 3, 2009; pp. 1-8; vol. 19; John Wiley & Sons A/S.

Hayes, Tim; Next-Generation Cell Phone Cameras; OPN Optics & Photonics News; Feb. 2012; pp. 16-21.

Martin et al.; Role of commensal and probiotic bacteria in human health: a focus on inflammatory bowel disease; Microbial Cell Factories; bearing a date of 2013; pp. 1-11; BioMed Central Ltd.

Schrezenmeir et al.; Probiotics, prebiotics, and synbiotics-approaching a definition; The American Journal of Clinical Nutrition; bearing a date of Jan. 14, 2014; pp. 361-364; American Society for Clinical Nutrition.

Sciarra et al.; Aerosols; Remington—The Science and Practice of Pharmacy; pp. 1000-1017 (plus cover); Lipponcott Williams & Wilkins.

Shu et al.; Fermentation of *Propionibacterium acnes*, a Commensal Bacterium in the Human Skin Microbiome, as Skin Probiotics against Methicillin-Resistant *Staphylococcus aureus*; PLOS One; Feb. 2013; pp. 1-11; vol. 8—Issue 2.

Szeliski, Richard; Image Alignment and Stitching: A Tutorial; Foundations and Trends in Computer Graphics and Vision; bearing a date of 2006; 105 pages; vol. 2; No. 2.

Zitvoá et al.; Image registration methods: a survey; Image and Vision Computing; bearing a date of Nov. 9, 2001; pp. 977-1000; Elsevier B.V.

European Patent Office, Supplementary European Search Report, Pursuant to Rule 62 EPC; App. No. EP 14838160; dated Mar. 27, 2017 (received by our Agent on Mar. 28, 2017); pp. 1-9.

European Patent Office, Supplementary European Search Report, Pursuant to Rule 62 EPC; App. No. EP 14838524; dated Apr. 3, 2017 (received by our Agent on Mar. 29, 2017); pp. 1-11.

European Patent Office, Supplement European Search Report, Pursuant to Rule 62 EPC; App. No. EP 14838438; dated Nov. 10, 2017 (received by our Agent on Nov. 16, 2017); pp. 1-11.

\* cited by examiner

FIG. 6

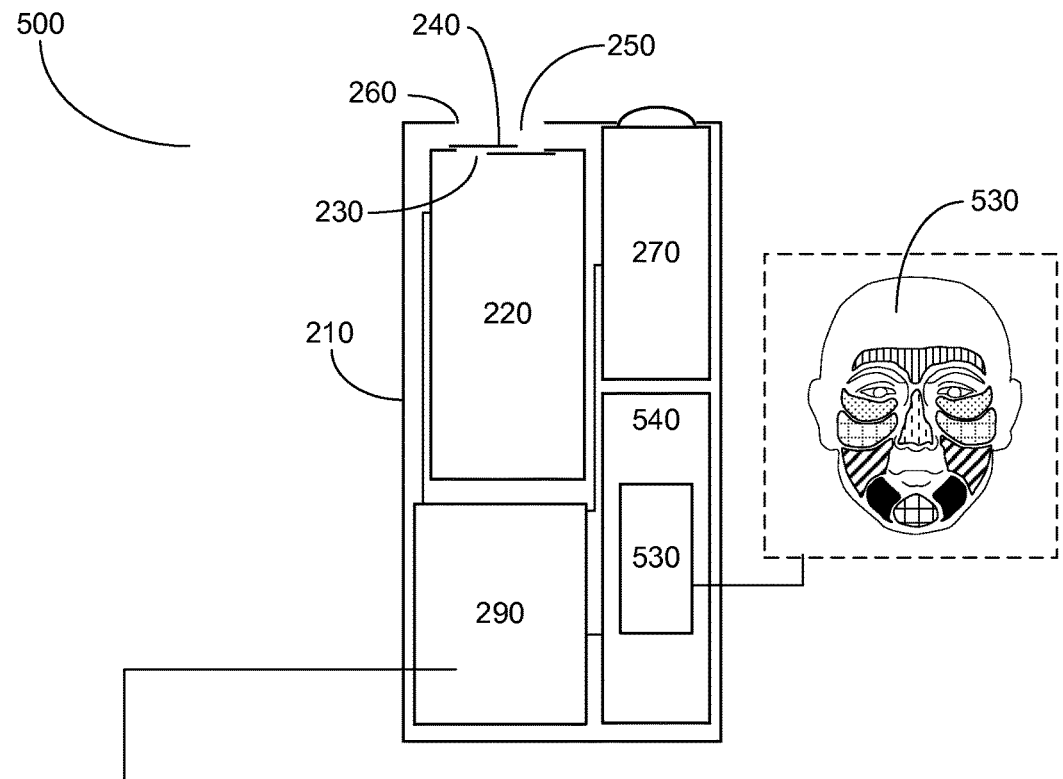

290 Computing component

600 Circuitry

610 Receive information associated with the measured feature of the location on the skin surface of the individual from the location-capture component

620 Correlate the received information associated with the measured feature of the location on the skin surface of the individual with the stored information associated with the microbe profile to determine a presence of at least one of the one or more types of microbes at said location

630 Select one or more treatment agents for application to the location on the skin surface of the individual from a database of treatment agents based on the presence of the at least one of the one or more types of microbes at said location

640 Actuate the controllable valve of at least one of the one or more treatment agent reservoirs to modulate release of the selected one or more treatment agents onto said location on the skin surface of the individual

FIG. 8

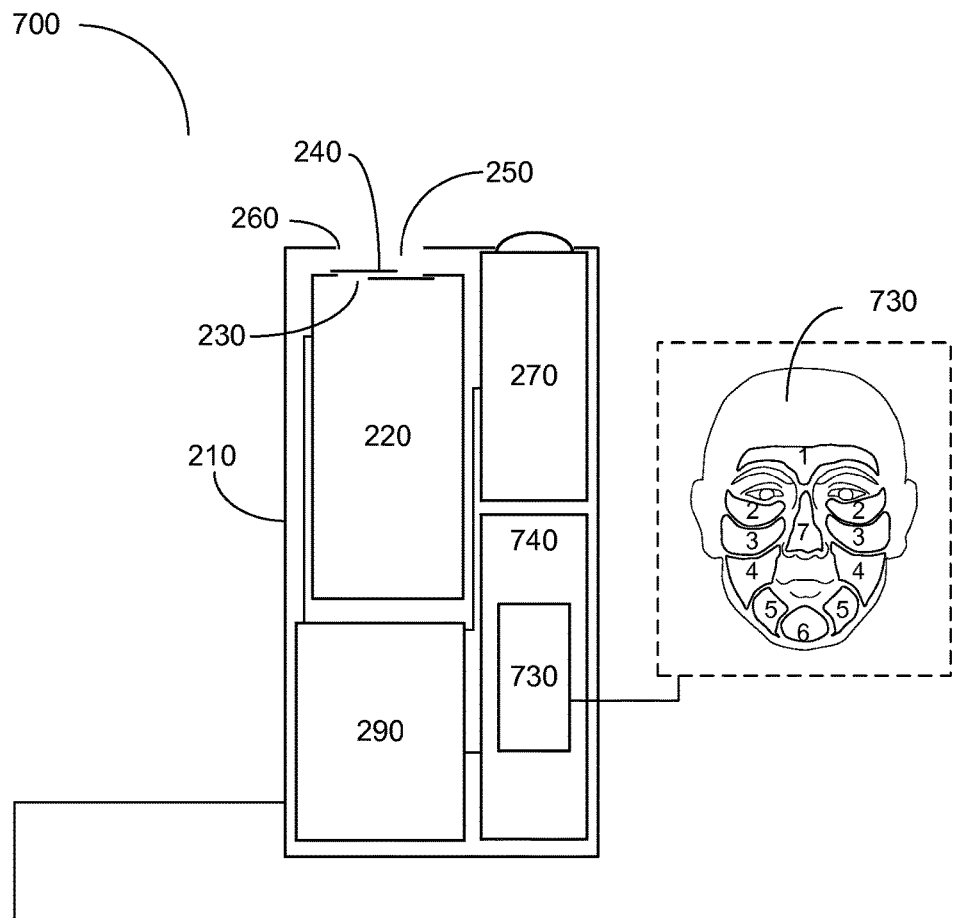

290 Computing Component

800 Circuitry

810 Receive information associated with the measured feature of the location on the skin surface of the individual from the location-capture component 820 Correlate the received information associated with the measured feature of the location on the skin surface of the individual with the stored information associated with the treatment map to select the one or more treatment agents for application at said location on the skin surface of the individual 830 Actuate the controllable valve of at least one of the one or more treatment agent reservoirs to modulate release of the selected one or more treatment agents for application at said location on the skin surface of the individual

1500
Receiving information associated with a location on the skin surface of an individual from a location-capture component of a skin-treatment delivery device, the skin-treatment delivery device including
    the location-capture component;
    one or more treatment agent reservoirs, each of the one or more treatment agent reservoirs including at least one port with a controllable valve;
    at least one conduit in fluid communication with the at least one port with the controllable valve and an opening defined by a surface of the skin treatment delivery device;
    a data storage component configured to store information associated with a microbe profile, the microbe profile including a two-dimensional spatial distribution of one or more types of microbes at each of one or more locations on the skin surface of the individual; and
    a computing component including a processor and circuitry, the computing component operably coupled to the location-capture component, the controllable valve of each of the one or more treatment agent reservoirs, and the data storage component

---

1510
Correlating the received information associated with the location on the skin surface of the individual with the stored information associated with the microbe profile to determine a presence of at least one of the one or more types of microbes at said location on the skin surface of the individual

---

1520
Selecting one or more treatment agents for application to the location on the skin surface of the individual from a database of treatment agents based on the presence of the at least one of the one or more types of microbes at said location on the skin surface of the individual

---

1530
Actuating the controllable valve of at least one of the one or more treatment agent reservoirs to modulate release of the selected one or more treatment agents onto said location on the skin surface of the individual

1500
Receiving information associated with a location on the skin surface of an individual from a location-capture component of a skin-treatment delivery device

---

1600 Receiving an update to the information associated with the location on the skin surface of the individual from the location-capture component in response to moving the skin-treatment delivery device to a new location on the skin surface of the individual

---

1610 Receiving the information associated with the microbe profile from a remote source

---

1620 Receiving an update to the information associated with the microbe profile

---

1510
Correlating the received information associated with the location on the skin surface of the individual with the stored information associated with the microbe profile to determine a presence of at least one of the one or more types of microbes at said location on the skin surface of the individual

1630 Aligning the received information associated with the location on the skin surface of the individual with one or more reference locations embedded in the microbe profile

---

1640 Alerting a user if the correlation between the received information associated with the location on the skin surface of the individual and the stored information associated with the microbe profile indicates that the location on the skin surface of the individual is outside a boundary of the microbe profile

---

1520
Selecting one or more treatment agents for application to the location on the skin surface of the individual from a database of treatment agents based on the presence of the at least one of the one or more types of microbes at said location on the skin surface of the individual

1650 Selecting one or more treatment agents for application to the location on the skin surface of the individual from a look-up table including treatment agents matched with type of microbes

---

1530
Actuating the controllable valve of at least one of the one or more treatment agent reservoirs to modulate release of the selected one or more treatment agents onto said location on the skin surface of the individual

1500
Receiving information associated with a location on the skin surface of an individual from a location-capture component of a skin-treatment delivery device 1510
Correlating the received information associated with the location on the skin surface of the individual with the stored information associated with the microbe profile to determine a presence of at least one of the one or more types of microbes at said location on the skin surface of the individual 1520
Selecting one or more treatment agents for application to the location on the skin surface of the individual from a database of treatment agents based on the presence of the at least one of the one or more types of microbes at said location on the skin surface of the individual 1530
Actuating the controllable valve of at least one of the one or more treatment agent reservoirs to modulate release of the selected one or more treatment agents onto said location on the skin surface of the individual 1700
Emitting one or more signals with a signal-generating component of the skin-treatment delivery device to notify a user of a condition 1710
Recording delivery data to the data storage component of the skin-treatment delivery device, the delivery data including the location on the skin surface of the individual and the one or more treatment agents delivered to said location 1720
Retrieving recorded delivery data from a past delivery event to inform a future delivery event 1730
Actuating the controllable valve of at least one of the one or more treatment agent reservoirs in response to a user interacting with an actuation component on the skin-treatment delivery device

FIG. 18

1800
Receiving information associated with a location on the skin surface of an individual from a location-capture component of a skin-treatment delivery device, the skin-treatment delivery device including
    the location-capture component;
    one or more treatment agent reservoirs, each of the one or more treatment agent reservoirs including at least one port with a controllable valve;
    at least one conduit in fluid communication with the at least one port with the controllable valve and an opening defined by a surface of the skin-treatment delivery device;
    a data storage component configured to store information associated with a treatment map, the treatment map including a two-dimensional spatial distribution of one or more treatment agents for application on the skin surface of the individual; and
    a computing component including a processor and circuitry, the computing component operably coupled to the location-capture component, the controllable valve of each of the one or more treatment agent reservoirs, and the data storage component 1810
Correlating the received information associated with the location on the skin surface of the individual with the stored information associated with the treatment map to select the one or more treatment agents for application at said location on the skin surface of the individual 1820
Actuating the controllable valve of at least one of the one or more treatment agent reservoirs to modulate release of the selected one or more treatment agents for application at said location on the skin surface of the individual

1800
Receiving information associated with a location on the skin surface of an individual from a location-capture component of a skin-treatment delivery device

---

1900 Receiving an update to the information associated with the location on the skin surface of the individual from the location-capture component in response to moving the skin-treatment delivery device to a new location on the skin surface of the individual

1910 Receiving the information associated with the treatment map from a remote source

1920 Receiving an update to the information associated with the treatment map

1930 Receiving the update to the information associated with the treatment map in response to an update to a microbe profile

---

1810
Correlating the received information associated with the location on the skin surface of the individual with the stored information associated with the treatment map to select the one or more treatment agents for application at said location on the skin surface of the individual

1940 Aligning the received information associated with the location on the skin surface of the individual with one or more reference locations embedded in the treatment map

---

1950 Alerting a user if the correlation between the received information associated with the location on the skin surface of the individual and the stored information associated with the treatment map indicates that the location on the skin surface of the individual is outside a boundary of the treatment map

---

1820
Actuating the controllable valve of at least one of the one or more treatment agent reservoirs to modulate release of the selected one or more treatment agents for application at said location on the skin surface of the individual

1800
Receiving information associated with a location on the skin surface of an individual from a location-capture component of a skin-treatment delivery device 1810
Correlating the received information associated with the location on the skin surface of the individual with the stored information associated with the treatment map to select the one or more treatment agents for application at said location on the skin surface of the individual 1820
Actuating the controllable valve of at least one of the one or more treatment agent reservoirs to modulate release of the selected one or more treatment agents for application at said location on the skin surface of the individual 2000
Emitting one or more signals with a signal-generating component of the skin-treatment delivery device to notify a user of a condition 2010
Recording delivery data to the data storage component of the skin-treatment delivery device, the delivery data including the location on the skin surface of the individual and the one or more treatment agents delivered to said location 2020
Retrieving recorded delivery data from a past delivery event to inform a future delivery event 2030
Actuating the controllable valve of at least one of the one or more treatment agent reservoirs in response to a user interacting with an actuation component on the skin-treatment delivery device

FIG. 21

2100
Receiving a two-dimensional microbe profile of a skin surface of an individual, the two-dimensional microbe profile including a two-dimensional spatial distribution of one or more types of microbes at each of one or more locations on the skin surface of the individual 2110
Selecting one or more treatment agents from a database of treatment agents, the selected one or more treatment agents to treat at least one of the one or more types of microbes at each of the one or more locations on the skin surface of the individual 2120
Generating the treatment map by mapping the selected one or more treatment agents to treat the at least one of the one or more types of microbes at each of the one or more locations on the skin surface of the individual to each of one or more corresponding locations on the two-dimensional microbe profile of the skin surface of the individual 2130
Reporting the generated treatment map to a user

FIG. 22

2100
Receiving a two-dimensional microbe profile of a skin surface of an individual, the two-dimensional microbe profile including a two-dimensional spatial distribution of one or more types of microbes at each of one or more locations on the skin surface of the individual > 2200 Receiving the two-dimensional microbe profile from an internal source > 2210 Receiving the two-dimensional microbe profile from an external source
>
>> 2220 Receiving the two-dimensional microbe profile from at least one of a microbe profiling device, a second computing device, or the Internet > 2230 Receiving the two-dimensional microbe profile overlaid with a feature map of the skin surface of the individual, the feature map of the skin surface of the individual including at least one of an image map, a fiducial marker map, or a coordinate map of the skin surface of the individual 2110
Selecting one or more treatment agents from a database of treatment agents, the selected one or more treatment agents to treat at least one of the one or more types of microbes at each of the one or more locations on the skin surface of the individual 2120
Generating a treatment map by mapping the selected one or more treatment agents to treat the at least one of the one or more types of microbes at each of the one or more locations on the skin surface of the individual to each of one or more corresponding locations on the two-dimensional microbe profile of the skin surface of the individual 2130
Reporting the generated treatment map to a user

FIG. 23

| 2100 Receiving a two-dimensional microbe profile of a skin surface of an individual, the two-dimensional microbe profile including a two-dimensional spatial distribution of one or more types of microbes at each of one or more locations on the skin surface of the individual |
|---|

| 2110 Selecting one or more treatment agents from a database of treatment agents, the selected one or more treatment agents to treat at least one of the one or more types of microbes at each of the one or more locations on the skin surface of the individual |
|---|
| 2300 Selecting one or more treatment agents from a database of treatment agents stored in the computing device |
| 2310 Selecting one or more treatment agents from a database of treatment agents stored in a remote location |
| 2320 Selecting one or more probiotics from the database of treatment agents |
| 2330 Selecting one or more prebiotics from the database of treatment agents |
| 2340 Selecting one or more of an antimicrobial agent, a therapeutic agent, or a chemotherapeutic agent from the database of treatment agents |

| 2120 Generating a treatment map by mapping the selected one or more treatment agents to treat the at least one of the one or more types of microbes at each of the one or more locations on the skin surface of the individual to each of one or more corresponding locations on the two-dimensional microbe profile of the skin surface of the individual |
|---|
| 2350 Incorporating information associated with the selected one or more treatment agents at each of the one or more corresponding locations on the two-dimensional microbe profile |
| 2360 Incorporating information associated with at least one of a name, dose, or a dose schedule associated with the selected one or more treatment agents at each of the one or more corresponding locations on the two-dimensional microbe profile |

| 2130 Reporting the generated treatment map to a user |
|---|

2100
Receiving a two-dimensional microbe profile of a skin surface of an individual, the two-dimensional microbe profile including a two-dimensional spatial distribution of one or more types of microbes at each of one or more locations on the skin surface of the individual

---

2110
Selecting one or more treatment agents from a database of treatment agents, the selected one or more treatment agents to treat at least one of the one or more types of microbes at each of the one or more locations on the skin surface of the individual

---

2120
Generating a treatment map by mapping the selected one or more treatment agents to treat the at least one of the one or more types of microbes at each of the one or more locations on the skin surface of the individual to each of one or more corresponding locations on the two-dimensional microbe profile of the skin surface of the individual

---

2400
Mapping the selected one or more treatment agents to treat the at least one of the one or more types of microbes at each of the one or more locations on the skin surface of the individual to each of one or more corresponding locations on a feature map associated with the two-dimensional microbe profile

---

2130
Reporting the generated treatment map to a user

> 2410 Reporting the generated treatment map to the user on a display

> 2420 Reporting the generated treatment map to the user on a printout

> 2430 Reporting the generated treatment map to the user on a second computing device

---

2440 Transmitting information associated with the generated treatment map to a remote source

---

2450 Transmitting information associated with the generated treatment map to a second computing device

---

2460 Transmitting information associated with the generated treatment map to a skin-treatment delivery device

FIG. 25

2500 A system for generating a treatment map, comprising

2510
Circuitry for receiving a two-dimensional microbe profile of a skin surface of an individual, the two-dimensional microbe profile including a two-dimensional spatial distribution of one or more types of microbes at each of one or more locations on the skin surface of the individual

2520
Circuitry for selecting one or more treatment agents from a database of treatment agents, the selected one or more treatment agents to treat at least one of the one or more types of microbes at each of the one or more locations on the skin surface of the individual

2530
Circuitry for generating the treatment map by mapping the selected one or more treatment agents to treat the at least one of the one or more types of microbes at each of the one or more locations on the skin surface of the individual to one or more corresponding locations on the two-dimensional microbe profile of the skin surface of the individual

2540
Circuitry for reporting the generated treatment map to a user

FIG. 26

2600

2610

2620 Circuitry

2630
Circuitry for receiving a two-dimensional microbe profile of a skin surface of an individual, the two-dimensional microbe profile including a two-dimensional spatial distribution of one or more types of microbes at each of one or more locations on the skin surface of the individual

2640
Circuitry for selecting one or more treatment agents from a database of treatment agents, the selected one or more treatment agents to treat at least one of the one or more types of microbes at each of the one or more locations on the skin surface of the individual

2650
Circuitry for generating the treatment map by mapping the selected one or more treatment agents to treat the at least one of the one or more types of microbes at each of the one or more locations on the skin surface of the individual to one or more corresponding locations on the two-dimensional microbe profile of the skin surface of the individual

2660
Circuitry for reporting the generated treatment map to a user

FIG. 27

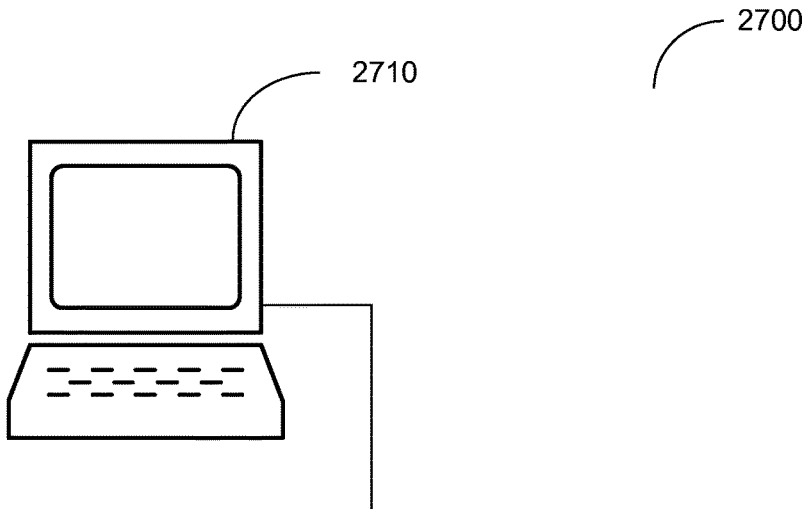

2720 Non-transitory signal-bearing medium bearing one or more instructions for generating a treatment map 2730
One or more instructions for receiving a two-dimensional microbe profile of a skin surface of an individual, the two-dimensional microbe profile including a two-dimensional spatial distribution of one or more types of microbes at each of one or more locations on the skin surface of the individual 2740
One or more instructions for selecting one or more treatment agents from a database of treatment agents, the selected one or more treatment agents to treat at least one of the one or more types of microbes at each of the one or more locations on the skin surface of the individual 2750
One or more instructions for generating the treatment map by mapping the selected one or more treatment agents to treat the at least one of the one or more types of microbes at each of the one or more locations on the skin surface of the individual to one or more corresponding locations on the two-dimensional microbe profile of the skin surface of the individual 2760
One or more instructions for reporting the generated treatment map to a user

FIG. 28

2800 An article of manufacture, comprising

2810 Non-transitory signal-bearing medium bearing one or more instructions for generating a treatment map

2820
One or more instructions for receiving a two-dimensional microbe profile of a skin surface of an individual, the two-dimensional microbe profile including a two-dimensional spatial distribution of one or more types of microbes at each of one or more locations on the skin surface of the individual

2830
One or more instructions for selecting one or more treatment agents from a database of treatment agents, the selected one or more treatment agents to treat at least one of the one or more types of microbes at each of the one or more locations on the skin surface of the individual

2840
One or more instructions for generating the treatment map by mapping the selected one or more treatment agents to treat the at least one of the one or more types of microbes at each of the one or more locations on the skin surface of the individual to one or more corresponding locations on the two-dimensional microbe profile of the skin surface of the individual

2850
One or more instructions for reporting the generated treatment map to a user

SYSTEMS, METHODS, AND DEVICES FOR DELIVERING TREATMENT TO A SKIN SURFACE

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 13/975,055, entitled SYSTEMS, METHODS, AND DEVICES FOR ASSESSING MICROBIOTA OF SKIN, naming Mahalaxmi G. Bangera, Michael H. Baym, Roderick A. Hyde, Jordin T. Kare, Eric C. Leuthardt, Gary L. McKnight, Tony S. Pan, Katherine E. Sharadin, Elizabeth A. Sweeney, Clarence T. Tegreene, and Lowell L. Wood, Jr. as inventors, filed 23, Aug. 2013, which is currently co-pending or is an application of which a currently co-pending application is entitled to the benefit of the filing date.

The present application constitutes a continuation-in-part of U.S. patent application Ser. No. 14/091,762, entitled DEVICES AND METHODS FOR PROFILING MICROBIOTA OF SKIN, naming Michael H. Baym, Roderick A. Hyde, Jordin T. Kare, Eric C. Leuthardt, Gary L. McKnight, Tony S. Pan, Elizabeth A. Sweeney, Clarence T. Tegreene, Lowell L. Wood, Jr. as inventors, filed 27, Nov. 2013, which is currently co-pending or is an application of which a currently co-pending application is entitled to the benefit of the filing date.

The present application constitutes a continuation-in-part of U.S. patent application Ser. No. 14/091,832, entitled DEVICES AND METHODS FOR SAMPLING AND PROFILING MICROBIOTA OF SKIN, naming Michael H. Baym, Roderick A. Hyde, Jordin T. Kare, Eric C. Leuthardt, Gary L. McKnight, Tony S. Pan, Elizabeth A. Sweeney, Clarence T. Tegreene, Lowell L. Wood, Jr. as inventors, filed 27, Nov. 2013, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a skin-treatment delivery device includes, but is not limited to, a hand-held housing including one or more treatment agent reservoirs, each of the one or more treatment agent reservoirs including at least one port with a controllable valve; at least one conduit in fluid communication with the at least one port with the controllable valve and an opening defined by a surface of the hand-held housing; a data storage component configured to store information associated with a microbe profile, the microbe profile including a two-dimensional spatial distribution of one or more types of microbes at each of one or more locations on a skin surface of an individual; a location-capture component including circuitry to measure a feature of a location on the skin surface of the individual; and a computing component including a processor, the computing component operably coupled to the controllable valve of each of the one or more treatment agent reservoirs, the data storage component, and the location-capture component, the computing component including circuitry to receive information associated with the measured feature of the location on the skin surface of the individual from the location-capture component; correlate the received information associated with the measured feature of the location on the skin surface of the individual with the stored information associated with the microbe profile to determine a presence of at least one of the one or more types of microbes at said location; select one or more treatment agents for application to the skin surface of the individual from a database of treatment agents based on the presence of the at least one of the one or more types of microbes at said location; and actuate the controllable valve of at least one of the one or more treatment agent reservoirs to modulate release of the selected one or more treatment agents onto said location on the skin surface of the individual. In addition to the foregoing, other device aspects are described in the claims, drawings, and text forming a part of the present disclosure.

In an aspect, a method of delivering a treatment to a skin surface includes, but is not limited to, receiving information associated with a location on the skin surface of an individual from a location-capture component of a skin-treatment delivery device, the skin-treatment delivery device including the location-capture component; one or more treatment agent reservoirs, each of the one or more treatment agent reservoirs including at least one port with a controllable valve; at least one conduit in fluid communication with the at least one port with the controllable valve and an opening defined by a surface of the skin-treatment delivery device; a data storage component configured to store information associated with a microbe profile, the microbe profile including a two-dimensional spatial distribution of one or more types of microbes at each of one or more locations on the skin surface of the individual; and a computing component including a processor and circuitry, the computing component operably coupled to the location-capture component, the controllable valve of each of the one or more treatment agent reservoirs, and the data storage component; correlating the received information associated with the location on the skin surface of the individual with the stored information associated with the microbe profile to determine a presence of at least one of the one or more types of microbes at said location on the skin surface of the individual; selecting one or more treatment agents for application to the location on the skin surface of the individual from a database of treatment agents based on the presence of the at least one of the one or more types of microbes at said location on the skin surface of the individual; and actuating the controllable valve of at least one of the one or more treatment agent reservoirs to modulate release of the selected one or more treatment agents onto said location on the skin surface of the individual. In addition to the foregoing, other method aspects are described in the claims, drawings, and text forming a part of the present disclosure.

In an aspect, a system for delivering a skin treatment includes, but is not limited to, one or more location-capture components including circuitry to determine a location on a skin surface of an individual; a treatment unit including one or more treatment agent reservoirs, each of the one or more treatment agent reservoirs including a controllable valve; and a computing device including a processor, the computing device operably coupled to the one or more location-capture components and the treatment unit, the computing device including a data storage component configured to store information associated with a microbe profile, the microbe profile including a two-dimensional spatial distribution of one or more types of microbes on the skin surface of the individual; and circuitry to receive information associated with the location on the skin surface of the individual from the one or more location-capture components; correlate the received information associated with the location on the skin surface of the individual with the stored information associated with the microbe profile to determine a presence of at least one of the one or more types of microbes at said location on the skin surface of the individual; select one or more treatment agents for application to the location of the skin surface of the individual from a database of treatment agents based on the presence of the at least one of the one or more types of microbes at said location on the skin surface of the individual; and actuate the controllable valve of at least one of the one or more treatment agent reservoirs to modulate release of the selected one or more treatment agents onto said location on the skin surface of the individual. In addition to the foregoing, other systems aspects are described in the claims, drawings, and text forming a part of the present disclosure.

In an aspect, a skin-treatment delivery device includes, but is not limited to, a hand-held housing including one or more treatment agent reservoirs, each of the one or more treatment agent reservoirs including at least one port with a controllable valve; at least one conduit in fluid communication with the at least one port with the controllable valve and an opening defined by a surface of the hand-held housing; a location-capture component including circuitry to measure a feature of a location on a skin surface of an individual; a data storage component configured to store information associated with a treatment map, the treatment map including a two-dimensional spatial distribution of one or more treatment agents for application to the skin surface of the individual; and a computing component including a processor, the computing component operably coupled to the controllable valve of the one or more treatment reservoirs, the location-capture component, and the data storage component, the computing component including circuitry to receive information associated with the measured feature of the location on the skin surface of the individual from the location-capture component; correlate the received information associated with the measured feature of the location on the skin surface of the individual with the stored information associated with the treatment map to select the one or more treatment agents for application at said location on the skin surface of the individual; and actuate the controllable valve of at least one of the one or more treatment agent reservoirs to modulate release of the selected one or more treatment agents for application at said location on the skin surface of the individual. In addition to the foregoing, other device aspects are described in the claims, drawings, and text forming a part of the present disclosure.

In an aspect, a method of delivering a treatment to a skin surface includes, but is not limited to, receiving information associated with a location on the skin surface of an individual with a location-capture component of a skin-treatment delivery device, the skin-treatment delivery device including the location-capture component; one or more treatment agent reservoirs, each of the one or more treatment agent reservoirs including at least one port with a controllable valve; at least one conduit in fluid communication with the at least one port with the controllable valve and an opening defined by a surface of the skin-treatment delivery device; a data storage component configured to store information associated with a treatment map, the treatment map including a two-dimensional spatial distribution of one or more treatment agents for application on the skin surface of the individual; and a computing component including a processor and circuitry, the computing component operably coupled to the location-capture component, the controllable valve of each of the one or more treatment agent reservoirs, and the data storage component; correlating the received information associated with the location on the skin surface of the individual with the stored information associated with the treatment map to select the one or more treatment agents for application at said location on the skin surface of the individual; and actuating the controllable valve of at least one of the one or more treatment agent reservoirs to modulate release of the selected one or more treatment agents for application at said location on the skin surface of the individual. In addition to the foregoing, other method aspects are described in the claims, drawings, and text forming a part of the present disclosure.

In an aspect, a system for delivering a skin treatment includes, but is not limited to, one or more location-capture components including circuitry to determine a location on a skin surface of an individual; a treatment unit including one or more treatment agent reservoirs, each of the one or more treatment agent reservoirs including a controllable valve; and a computing device, the computing device operably coupled to the one or more location-capture components and to the controllable valve of each of the one or more treatment agent reservoirs, the computing device including a data storage component configured to store information associated with a treatment map, the treatment map including a two-dimensional spatial distribution of one or more treatment agents for application to one or more locations on the skin surface of the individual; and circuitry to receive information associated with the location on the skin surface of the individual from the one or more location-capture components; circuitry to correlate the received information associated with the location on the skin surface of the individual with the stored information associated with the treatment map to select the one or more treatment agents for application at said location; and circuitry to actuate the controllable valve of at least one of the one or more treatment agent reservoirs to modulate release of the selected one or more treatment agents for application at said location on the skin surface of the individual. In addition to the foregoing, other system aspects are described in the claims, drawings, and text forming a part of the present disclosure.

In an aspect, a method of generating a treatment map includes, but is not limited to, receiving a two-dimensional microbe profile of a skin surface of an individual, the two-dimensional microbe profile including a two-dimensional spatial distribution of one or more types of microbes at each of one or more locations on the skin surface of the individual; selecting one or more treatment agents from a database of treatment agents, the selected one or more treatment agents to treat at least one of the one or more types of microbes at each of the one or more locations on the skin surface of the individual; generating the treatment map by mapping the selected one or more treatment agents to treat the at least one of the one or more types of microbes at each of the one or more locations on the skin surface of the individual to each of one or more corresponding locations on the two-dimensional microbe profile of the skin surface of the individual; and reporting the generated treatment map to a user. In addition to the foregoing, other method aspects are described in the claims, drawings, and text forming a part of the present disclosure.

In an aspect, a system for generating a treatment map includes, but is not limited to, circuitry for receiving a two-dimensional microbe profile of a skin surface of an individual, the two-dimensional microbe profile including a two-dimensional spatial distribution of one or more types of microbes at each of one or more locations on the skin surface of the individual; circuitry for selecting one or more treatment agents from a database of treatment agents, the selected one or more treatment agents to treat at least one of the one or more types of microbes at each of the one or more locations on the skin surface of the individual; circuitry for generating the treatment map by mapping the selected one or more treatment agents to treat the at least one of the one or more types of microbes at each of the one or more locations on the skin surface of the individual to one or more corresponding locations on the two-dimensional microbe profile of the skin surface of the individual; and circuitry for reporting the generated treatment map to a user. In addition to the foregoing, other system aspects are described in the claims, drawings, and text forming a part of the present disclosure.

In an aspect, a system includes, but is not limited to, a computer processor; and non-transitory signal-bearing medium bearing one or more instructions for generating a treatment map, the non-transitory signal-bearing medium including one or more instructions for receiving a two-dimensional microbe profile of a skin surface of an individual, the two-dimensional microbe profile including a two-dimensional spatial distribution of one or more types of microbes at each of one or more locations on the skin surface of the individual; one or more instructions for selecting one or more treatment agents from a database of treatment agents, the selected one or more treatment agents to treat at least one of the one or more types of microbes at each of the one or more locations on the skin surface of the individual; one or more instructions for generating the treatment map by mapping the selected one or more treatment agents to treat the at least one of the one or more type of microbes at each of the one or more locations on the skin surface of the individual to one or more corresponding locations on the two-dimensional microbe profile of the skin surface of the individual; and one or more instructions for reporting the generated treatment map to a user. In addition to the foregoing, other system aspects are described in the claims, drawings, and text forming a part of the present disclosure.

In an aspect, an article of manufacture includes, but is not limited to, non-transitory signal-bearing medium bearing one or more instructions for generating a treatment map, the non-transitory signal-bearing medium including one or more instructions for receiving a two-dimensional microbe profile of a skin surface of an individual, the two-dimensional microbe profile including a two-dimensional spatial distribution of one or more types of microbes at each of one or more locations on the skin surface of the individual; one or more instructions for selecting one or more treatment agents from a database of treatment agents, the selected one or more treatment agents to treat at least one of the one or more types of microbes at each of the one or more locations on the skin surface of the individual; one or more instructions for generating the treatment map by mapping the selected one or more treatment agents to treat the at least one of the one or more types of microbes at each of the one or more locations on the skin surface of the individual to one or more corresponding locations on the two-dimensional microbe profile of the skin surface of the individual; and one or more instructions for reporting the generating treatment map to a user. In addition to the foregoing, other article of manufacture aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 6 is a schematic of a skin-treatment delivery device with a microbe profile.

FIG. 8 is a schematic of a skin-treatment delivery device with a treatment map.

FIG. 15 is a flowchart of a method for treating a skin surface.

FIG. 16 illustrates further aspects of a method such as shown in FIG. 15.

FIG. 17 shows further aspects of a method such as illustrated in FIG. 15.

FIG. 18 is a flowchart of a method for treating a skin surface.

FIG. 19 illustrates further aspects of a method such as shown in FIG. 18.

FIG. 20 shows further aspects of a method such as illustrated in FIG. 18.

FIG. 21 is a flowchart of a method for generating a treatment map.

FIG. 22 illustrates further aspects of a method such as shown in FIG. 21.

FIG. 23 shows further aspects of a method such as depicted in FIG. 21.

FIG. 24 depicts further aspects of a method such as illustrated in FIG. 21.

FIG. 25 shows a system including circuitry for generating a treatment map.

FIG. 26 shows a system including circuitry and a computing device for generating a treatment map.

FIG. 27 shows a system including a computing device and non-transitory signal-bearing medium for generating a treatment map.

FIG. 28 shows an article of manufacture for generating a treatment map.

DETAILED DESCRIPTION

Figure 1:
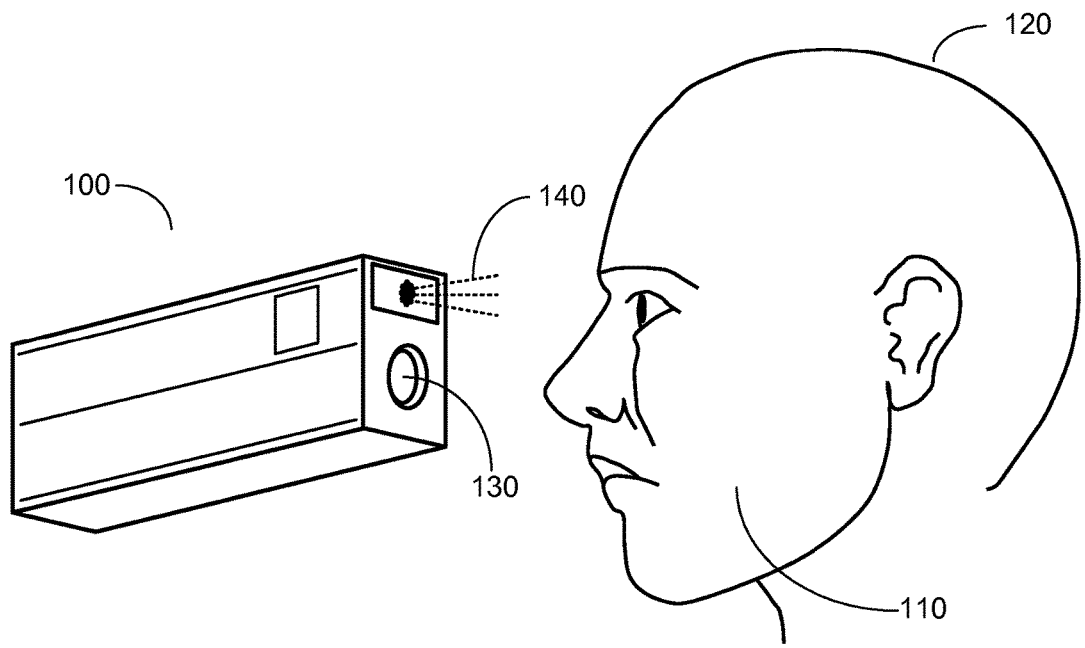
FIG. 1 illustrates an embodiment of a skin-treatment delivery device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The skin, the largest organ of the mammalian body, is inhabited at any one time by a diverse array of microbes. Such microbes can include bacteria, fungi, viruses, parasites, archaea, or small arthropods (e.g., mites). Variations in regional properties of the skin, e.g., variations in pH, moisture, pores, texture, and the like, from one body location to another contribute to the spatial diversity of skin-associated microbes. Similarly, the type of microbes and/or spatial distribution of one or more microbes on the skin surface may change in response to cleaning of the skin surface, application of anti-microbial agents, application of irritating agents, e.g., make-up, lotion, or sun screen, exposure to irritating conditions, e.g., diet, disease, wind, temperature, humidity, or sun exposure, or intrinsic individual factors, e.g., individual's genome, age, sex, and/or stage of sexual maturity. In some instances, skin-resident microbes on the skin surface, e.g., commensal bacteria, provide a benefit to the individual. For example, *Staphylococcus epidermidis* has been demonstrated to modulate the host innate immune response, inhibiting the growth of other bacterial pathogens such as *Staphylococcus aureus* and Group A *Streptococcus*. See, e.g., Grice & Segre (2011) *Nat. Rev. Microbiol.* 9:244-53, which is incorporated herein by reference. In some instances, microbes have been linked to pathological conditions including acne, psoriasis, and atopic dermatitis. See, e.g., Cho & Blaser (2012) *Nat. Rev. Genet.* 13:260-270, which is incorporated herein by reference. In general, understanding the identity and spatial distribution of microbes on the skin under normal and/or pathological conditions can contribute to decisions regarding therapeutic, preventative, and/or cosmetic treatments. Systems, methods, and devices for mapping microbes on the skin surface of an individual and generating a microbe profile have been described in U.S. patent application Ser. Nos. 13/975,055; 13/975,067; 13/975,079; 14/091,762; 14/091,793; 14/091,805; 14/091,832; and 14/091,856, each of which is incorporated herein by reference. Described herein are devices, systems, and methods for delivering a treatment regimen to the skin surface of an individual based on the spatial distribution of at least one type of microbe on the skin surface of individual. Described herein are systems and methods for generating a treatment map from a microbe profile.

With reference to FIG. 1, shown is an example of a skin-treatment delivery device 100 which can serve as a context for one or more devices, systems, and methods described herein for delivering a treatment regimen to the skin surface of an individual based on a microbe profile. Skin-treatment delivery device 100 includes a location-capture component 130 including circuitry to measure a feature of a location on skin surface 110 of an individual 120. Skin-treatment delivery device 100 includes circuitry to compare the measured feature of the location of skin surface 110 of individual 120 with a map or profile stored in a data storage component of skin-treatment delivery device 100. Skin-treatment delivery device 100 includes circuitry to modulate release of one or more treatment agents 140 to a location on skin surface 110 of individual 120 based on the type(s) of microbe at said location.

Figure 2:
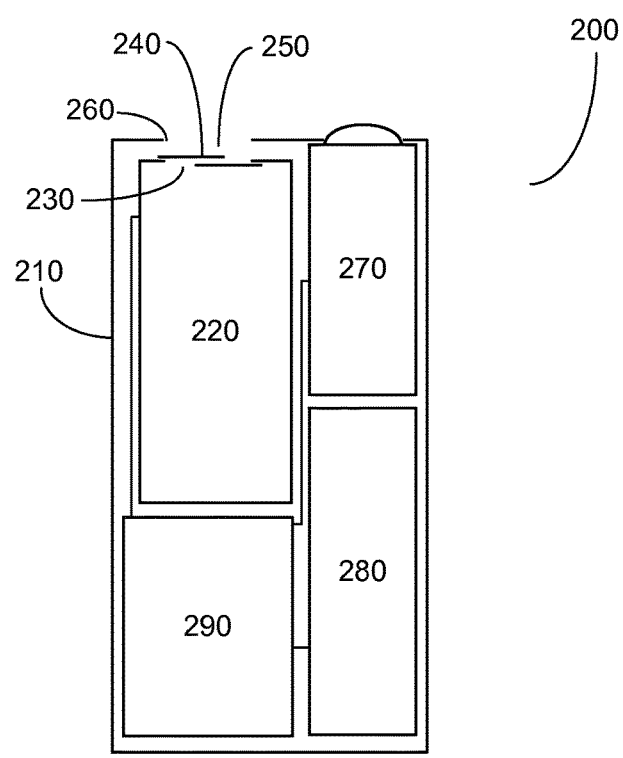
FIG. 2 is a schematic of a skin-treatment delivery device.

FIG. 2 shows further aspects of a skin-treatment delivery device. Skin-treatment delivery device 200 includes hand-held housing 210 sized for use with one hand. Hand-held housing 210 includes treatment agent reservoir 220. Treatment agent reservoir 220 is configured to store and controllably release one or more treatment agents. Treatment agent reservoir 220 includes at least one port 230 with a controllable valve 240. Hand-held housing 210 further includes conduit 250. Conduit 250 is in fluid communication with at least one port 230 with controllable valve 240 and opening 260 defined by a surface of hand-held housing 210. In an aspect, skin-treatment delivery device 200 includes one or more conduits for releasing the one or more treatment agents on a skin surface of an individual. Hand-held housing 210 of skin-treatment delivery device 200 further includes location-capture component 270. Location-capture component 270 includes circuitry to measure a feature, e.g., a physical landmark, of a location on the skin surface of the individual. Hand-held housing 210 further includes data storage component 280. Data storage component 280 is configured to store information, e.g., information associated with a microbe profile or a treatment map. Hand-held housing 210 further includes computing component 290 including a processor. Computing component 290 is operably coupled to controllable valve 240, location-capture component 270, and data storage component 280. Computing component 290 includes circuitry to receive information associated with the measured feature of the location on the skin surface of the individual from location-capture component 270, to correlate the received information associated with the measured feature of the location on the skin surface of the individual with stored information associated with the microbe profile or the treatment map, and to activate controllable valve 240 to modulate release of one or more treatment agents from treatment reservoir 220 and onto the location on the skin surface of the individual.

Hand-Held Housing

Skin-treatment delivery device 200 includes a hand-held housing. In an aspect, the hand-held housing is sized for use with one hand. For example, the hand-held housing can be sized for allowing a user to hold the device with a single hand, e.g., the size of an electric razor, and to easily move the device across the skin surface of an individual. In an aspect, the user is the individual undergoing treatment, e.g., the individual is self-administering one or more treatment agents in a location-based manner. In an aspect, the user is a medical practitioner or other practitioner, e.g., a cosmetologist. In an aspect, the hand-held housing is sized to accommodate the various components of the skin-treatment delivery device, e.g., sized to accommodate at least one treatment agent reservoir, the location-capture component, the data storage component, and the computing component, and any additional components, e.g., a power source, a transmission unit, a user interface, an actuation interface, a signal-generating component, and the like.

In an aspect, the hand-held housing is constructed of plastic. For example, the hand-held housing may be constructed of two or more pieces of molded plastic configured to enclose the various components of the skin-treatment delivery device. In this instance, the two or more pieces of plastic may be held together around the various components of the device by one or more screws, adhesive or glue, laser or heat welding, interlocking pins or snaps, or the like. In an aspect, the hand-held housing is constructed of one or more of plastic, metal, ceramic, resin, rubber, or polymer. For example, the hand-held housing can be constructed of a polymer, e.g., polycarbonate. For example, the hand-held housing can be constructed of a ceramic material, e.g., zirconia and/or alumina (see, e.g., U.S. Patent Application 2013/0078298, which is incorporated herein by reference). In an aspect, the hand-held housing includes an ergonomic design, e.g., features that allow for ease of gripping the skin-treatment delivery device with a single hand. For example, the hand-held housing may include molded exterior portions shaped to accommodate one or more fingers gripping the skin-treatment delivery device.

Treatment Agent Reservoir

Skin-treatment delivery device 200 includes one or more treatment agent reservoirs 220. In an aspect, each of the treatment agent reservoirs is configured to store and controllably release at least one of the one or more treatment agents for application to the location on the skin surface of the individual. The treatment agent reservoir further includes at least one port 230, e.g., an opening defined by a wall of the treatment agent reservoir, and controllable valve 240 in the at least one port 230 for modulating release of the one or more treatment agents from treatment agent reservoir 220.

The one or more treatment agent reservoirs are configured to store and controllably release one or more treatment agents. In an aspect, the one or more treatment agents include one or more agents configured to maintain, alter, and/or improve the skin microbiota, e.g., the types and quantity of microorganisms, on the skin surface of the individual. In an aspect, the one or more treatment agents include one or more agents configured to treat a condition or disease on the skin surface of the individual. Non-limiting examples of conditions or diseases of the skin include inflammation, e.g., eczema, hives, atopic dermatitis, or psoriasis; a microbial infection, e.g., a bacterial, fungal, or viral infection; acne, actinic keratosis, rosacea, seborrheic dermatitis, seborrheic keratosis, warts, or skin cancer, e.g., melanoma, squamous cell carcinoma, or basal cell carcinoma; tinea pedis; aging skin; and dry or sensitive skin.

In an aspect, the one or more treatment agents include one or more probiotics. In an aspect, the one or more probiotics include one or more skin commensal microorganisms which positively affect the skin microbiota. For example, the one or more probiotics can include microorganisms that positively affect the skin surface environment, e.g., by altering the pH or inhibiting growth of pathogenic microorganisms. In an aspect, the one or more probiotics can include one or more microorganisms naturally found on the skin surface of the individual. In an aspect, the one or more probiotics can include one or more microorganism that are not naturally found on the skin surface of the individual, but positively affect the skin surface environment. In an aspect, the one or more probiotics can include one or more engineered microorganisms. For example, the one or more probiotics can include a microorganism genetically engineered to have a property that positively affects the skin surface environment, e.g., by synthesizing and excreting an inhibitor of pathogenic microorganisms. See, e.g., Martin et al. (2013) *Microbial Cell Factories,* 12:71, which is incorporated herein by reference. In an aspect, the probiotic comprises live probiotic microorganisms. In an aspect, the probiotics may be included in a live form, dead form, semi-active or in deactivated form and fragments or fractions originating from the microorganism either live or dead (e.g., as a lyophilized powder). In an aspect, the probiotic includes culture supernatants of the microorganisms.

In an aspect, the one or more probiotics include one or more bacterial probiotics. See, e.g., U.S. Pat. No. 8,557,560, U.S. Patent Applications 2011/0274676, 2014/0037688, Schrezenmeir & De Vrese (2001) *Am. J. Clin. Nutr.* 73(suppl):361S-364S, and Gueniche et al. (2009) *Exp. Dermatol.* 19:e1-e8, which are incorporated herein by reference. In an aspect, the one or more bacterial probiotics include one or more of *Firmicutes, Actinobacteria, Bacteriodetes, Proteobacteria,* or *Cyanobacteria*. In an aspect, the one or more bacterial probiotics include one or more of *Corynebacteria, Propionibacteria, Micrococci,* or *Staphylococci*. In an aspect, the one or more bacterial probiotics include non-lactic acid and/or lactic acid producing bacteria (LAB) and can include *Bacteroides, Bifidobacterium,* and *Lactobacillus*. In an aspect, the one or more bacterial probiotics include certain strains of *Aerococcus, E. coli, Bacillus, Enterococcus, Fusobacterium, Lactococcus, Leuconostoc, Melissacoccus, Micrococcus, Oenococcus, Sporolactobacillus, Streptococcus, Staphylococcus, Saccharomyces, Pediococcus, Peptostreptococcus, Proprionebacterium,* and *Weissella*. A wide variety of strains of bacteria are available from the ATCC, Manassas, Va. In an aspect, the one or more probiotics include one or more non-pathogenic strains of pathogenic bacteria.

In an aspect, the one or more probiotic can include a bacterial strain that inhibits a second bacterial strain, e.g., by out competing for resources or by inhibiting the growth of the second bacterial stain. In an aspect, the one or more probiotics include skin commensal microorganism *Staphylococcus epidermidis*. For example, *Staphylococcus epidermidis* may be used as a probiotic to modulate growth of pathogenic bacteria on the skin surface by producing microbial peptides that inhibit *Staphylococcus aureus* biofilm formation and/or by producing lanthionine-containing antibacterial peptides, e.g., bacteriocins, which are known to exhibit antibacterial properties toward certain species of harmful bacteria, e.g., *Streptococcus aureus* and *Streptococcus pyogenes*. For example, *Staphylococcus epidermidis* may be used as a probiotic to stimulate the immune system by influencing the innate immune response of keratinocytes through Toll-like receptor ("TLR") signaling. For example, *Staphylococcus epidermidis* may be used as a probiotic to inhibit the action of more virulent microorganisms such as *Staphylococcus aureus* by occupying receptors on a host cell that also bind the virulent microorganism. See, e.g., Grice & Segre (2011) *Nat. Rev. Microbiol.* 9:244-53, which is incorporated herein by reference.

In an aspect, the one or more probiotics can include skin commensal microorganism *Propionibacterium acnes*. For example, *Propionibacterium acnes* can be used as a probiotic to consume skin oil and to produce byproducts such as short-chain fatty acids and propionic acid known to help maintain a healthy skin barrier. See, e.g., Shu et al. (2013) *PLoS ONE* 8(2):e55380, which is incorporated herein by reference.

In an aspect, the one or more treatment agents include one or more prebiotics. In an aspect, the one or more prebiotics are agents that promote the survival and/or growth of microorganisms of interest on the skin surface of the individual. In an aspect, the one or more prebiotics include at least one of galacto-oligosaccharides, fructo-oligosaccharides, inulin, or lactulose. In an aspect, the one or more prebiotics include one or more of iron, biotin, nicotinic acid, D-pantothenic acid, pyridoxal, pyridoxamine dihydrochloride, thiamin hydrochloride, valine, arginine, galactose, mannose, fructose, sucrose, lactose, or maltose. In an aspect, the one or more prebiotics include one or more of plant derived prebiotics, e.g., derived from acacia gum, konjac, chicory root, Jerusalem artichoke, asparagus, and dandelion greens. See, e.g., U.S. Patent Application 2013/0115317; and Bateni et al. (2013) *Am. J. Dermatology Venereology* 2:10-14, which are incorporated herein by reference.

In an aspect, the one or more treatment agents include one or more antimicrobial agents, e.g., antibacterial, antiviral, or antifungal agents. In an aspect, the one or more antimicrobial agents include at least one of an antibacterial agent, an antifungal agent, an antiparasitic agent, or an antiviral agent. In an aspect, the treatment agent reservoir includes one or more antibacterial agents configured to prevent or minimize bacterial infection on the skin surface of the individual. Non-limiting examples of antibacterial agents commonly used for topical applications include benzoyl peroxide, sodium sulfacetamide, erythromycin, mupirocin, retapamulin, bacitracin, neomycin, polymyxin b/e, silver sulfadiazine, or tetracycline. In an aspect, the treatment agent reservoir includes one or more antiviral agents configured to prevent or treat a viral infection. For example, the treatment agent reservoir can include an antiviral agent to prevent or treat viral infection of the skin surface associated with herpes simplex types 1 or 2. Non-limiting examples of antiviral agents commonly used for topical applications include acyclovir, docosanol, famciclovir, imiquimod, penciclovir, valacyclovir, and vidarabine. In an aspect, the treatment agent reservoir includes one or more antifungal agents configured to prevent or treat a fungal infection on the skin surface of the individual. Non-limiting examples of antifungal agents commonly used for topical applications include clotrimazole, amphotericin B, butaconazole, butenafine, ciclopirox olamine, econazole, ketoconazole, miconazole, naftifine, natamycin, nystatin, oxiconazole, sulconazole, terbinafine, terconazole, tioconazole, and tolnaftate.

In an aspect, the one or more treatment agents include one or more therapeutic agents. In an aspect, the one or more therapeutic agents include at least one of an anti-inflammatory agent, a chemotherapeutic agent, or an anti-acne agent.

In an aspect, the treatment agent reservoir includes one or more treatment agents to treat other conditions of the skin, e.g., inflammation or cancer. In an aspect, the one or more treatment agents include one or more of antiseptics, vitamins (e.g., Vitamin A or Vitamin D), or derivatives thereof, benzoyl peroxide, salicylic acid or other acids, hormone or retinoid creams, steroids, cortisone, emollients, moisturizers, chemotherapies, e.g., 5-fluorourasil. In an aspect, the one or more treatment agents include one or more retinoids for treating various conditions of the skin including, but not limited to, acne, psoriasis, photodamaged skin and cancers including AIDS-related Kaposi's sarcoma and cutaneous T-cell lymphoma. Non-limiting examples of retinoids for topical use include alitretinoin, bexarotene, adapalene, tazarotene, and isotretinoin.

In an aspect, the treatment agent reservoir includes one or more corticosteroid for treating various inflammatory dermatoses including, but not limited to, atopic dermatitis, psoriasis, lupus erythematosus, and the like. Non-limiting examples of corticosteroids for topical use include hydrocortisone and derivatives, betamethasone and derivatives, dexamethasone, prednisolone and derivatives, fluocinolone acetonide, fluorometholone, alclometasone dipropionate, triamcinolone acetonide, clocortolone pivalate, flumethasone pivalate, mometasone furoate, flurandrenolide, prednicarbate, fluticasone propionate, desonide, halcinonide, desoximetasone, flurandrenolide, fluocinonide, amcinonide, fluocinolone acetonide, and diflorasone diacetate.

In an aspect, the treatment agent reservoir includes one or more chemotherapy agents for treating cancer or other conditions of the skin surface. Non-limiting examples of chemotherapy agents for topical use include fluorouracil used for treating actinic keratoses and some types of basal cell carcinomas of the skin. In an embodiment, the at least one chemotherapy agent includes an immunomodulator, non-limiting examples of which include imiquimod, tacrolimus and pimecrolimus. In an embodiment, the at least one chemotherapy includes at least one agent for modulating pigmentation, non-limiting examples of which include hydroquinone, monobenzene, mequinol, trioxsalen and methoxsalen.

In an aspect, the treatment agent reservoir is configured to store and controllably release one or more buffers and/or media components for modulating and/or inhibiting microbial growth. For example, the one or more other agents can include buffers that modulate the pH conditions of the skin surface. For example, the one or more other agents can include a nutritional source, e.g., galactose, to encourage growth of microbes on the skin surface. Non-limiting examples of nutritional sources includes iron, biotin, nicotinic acid, D-pantothenic acid, glycerol, pyridoxal, pyridoxamine dihydrochloride, thiamin hydrochloride, valine, arginine, galactose, mannose, fructose, sucrose, lactose, or maltose.

In an aspect, the one or more treatment agents include at least one of a moisturizer, an anti-aging treatment agent, a retinoid, or a cosmetic agent. In an aspect, the one or more treatment agents include one or more of keratoregulators, keratolytics, healing and/or restructuring agents of the cutaneous barrier, PPAR, RXR or LXR agonists, sebum-regulating agents, anti-irritation and/or anti-inflammatory and/or soothing agents, antioxidant agents, anti-aging agents, depigmenting or hypopigmenting agents, pigmenting agents, lipolytic or lipogenesis inhibitor agents or anticellulitis or slimming agents, organic or mineral sunscreens and filters, preservatives, and immunomodulators.

In an aspect, the one or more treatment agents are formulated for topical administration. In an aspect, the one or more treatment agents are formulated in a form compatible with dispersal through the at least one controllable valve and onto the skin surface of the individual. In an aspect, the one or more treatment agents are formulated in liquid form. In an aspect, the one or more treatment agents are formulated in a liquid, emulsion, or semisolid concentrate form compatible with an aerosolized spray. In an aspect, the aerosolized spray is formed by air atomization, airless atomization, electrostatic, or ultrasonic means. For example, the one or more treatment agents can be formulated with a liquefied gas or compressed gas propellant. For example, the propellant can include fluorocarbons, hydrofluorocarbons, hydrochlorofluorcarbons, hydrocarbons, or ethers. For example, the propellant can include compressed gas, e.g., carbon dioxide, nitrous oxide, or nitrogen. For example, the one or more treatment agents can be formulated in a liquid under pressure which upon actuation of the controllable valve results in release of a spray containing the one or more treatment agents. For example, the one or more treatment agents can be formulated as a metered dose formulation including the one or more treatment agents, solvents, dispersing agents, and liquefied gas or compressed gas propellants. In an aspect, the one or more treatment agents are formulated in cream form. In an aspect, the one or more treatment agents are formulated in gel form. In an aspect, the one or more treatment agents are formulated in powder form. In an aspect, the one or more treatment agents are formulated in a solid or soft solid form which when rubbed directly on a skin surface leaves a film including the one or more treatment agents. For further reference regarding formulation of agents for topical application, see Sciarra & Sciarra, "Aerosols," in *Remington: The Science and Practice of Pharmacy.* 21$^{st}$ Edition (2006), Chapter 50, pp. 1000-1017, Lippincott Williams & Wilkins, Philadelphia, which is incorporated herein by reference.

Figure 3:
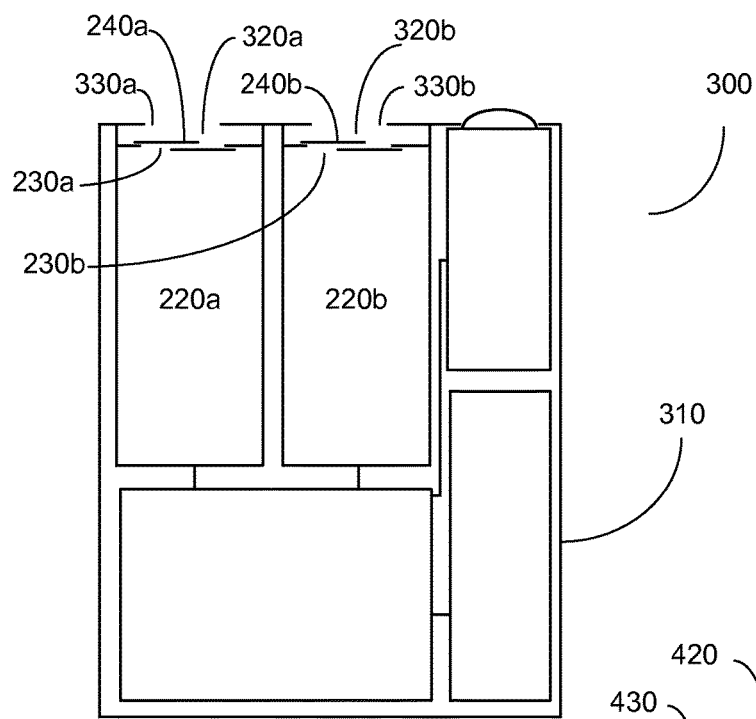
FIG. 3 is a schematic of a skin-treatment delivery device with two reservoirs.

Returning to FIG. 2, is an aspect, a skin-treatment delivery device includes one treatment agent reservoir to store and controllably release the one or more treatment agents. In an aspect, as shown in FIG. 3, a skin-treatment delivery device includes two or more treatment agent reservoirs, each with its own at least one port and controllable valve and each configured to store and controllable release one or more treatment agents. Skin-treatment delivery device 300 includes a hand-held housing 310 sized for use with a single hand and to accommodate the components of the device. Skin-treatment delivery device 300 includes a first treatment agent reservoir 220*a* and a second treatment agent reservoir 220*b*. First treatment agent reservoir 220*a* includes at least one port 230*a* with controllable valve 240*a*. A first conduit 320*a* is in fluid communication with at least one port 230*a* with controllable valve 240*a* and opening 330*a* of hand-held housing 310. Similarly, second treatment agent reservoir 220*b* includes at least one port 230*b* with controllable valve 240*b*. A second conduit 320*b* is in fluid communication with at least one port 230*b* with controllable valve 240*b* and opening 330*b* of hand-held housing 310. In an aspect, skin-treatment delivery device 300 includes at least one first treatment agent reservoir 220*a* configured to store and controllably release at least one treatment agent of a first type and at least one second treatment agent reservoir 220*b* configured to store and controllable release at least one treatment agent of a second type. For example, a first treatment agent reservoir may store and controllably release a first treatment agent, e.g., a probiotic agent, and a second treatment agent reservoir may store and controllably release a second treatment agent, e.g., a prebiotic agent. In an aspect, different combinations of the one or more treatment agents are delivered in varying concentrations through independent control of the respective controllable valves, e.g., controllable valves 240*a* and 240*b*. In an aspect, different combinations of the one or more treatment agents are delivered to a given location dependent upon the distribution of microbes in that location and the treatment needs.

In an aspect, the skin-treatment delivery device includes one or more treatment agent reservoirs configured to store and controllable release combinations of treatment agents appropriate for different parts of the body or conditions of the body. For example, one treatment agent reservoir may hold a combination of treatment agents appropriate for a skin surface associated with the face while a second treatment agent reservoir may hold a combination of treatment agents appropriate for skin surface on other parts of a body. For example, one treatment agent reservoir may hold a combination of treatment agents for a sebaceous site, a second treatment agent reservoir may hold a combination of treatment agents for moist sites, and a third treatment agent reservoir may hold a combination of treatment agents for dry sites. The combination of treatment agents released from the skin-treatment delivery device at any given location is dependent upon the distribution of microbes in said location and the treatment needs.

In an aspect, the treatment reservoir includes a series of compartments, each compartment containing a single dose of one or more treatment agents. Each of the series of compartments may be controllably opened to release the single dose of the one or more treatment agents. For example, the treatment reservoir may include a blister pack of compartments, each compartment containing a single dose of a treatment agent, each compartment further including a controllable valve, e.g., a penetrable seal.

In an aspect, the skin-treatment delivery device includes at least one treatment agent reservoir that is a replaceable cartridge. In an aspect, the contents of the replaceable cartridge include one or more treatment agents. In an aspect, the contents of the replaceable cartridge are personalized. In an aspect, the contents of the replaceable cartridge are personalized for a specific age, gender, ethnicity, or skin type, e.g., dry, oily, or combination skin. In an aspect, the contents of the replaceable cartridge are personalized for a specific condition, e.g., acne, rosacea, inflammation, psoriasis, actinic keratosis, or eczema. In an aspect, the contents of the replaceable cartridge are personalized for one or more specific microbes, e.g., one or more specific antimicrobials, one or more specific probiotic agents, or one or more specific prebiotic agents.

Controllable Valve

Each of the one or more treatment agent reservoirs of the skin-treatment delivery device includes at least one port with a controllable valve. In an aspect, the controllable valve is configured to controllably release one or more treatment agents from the treatment agent reservoir. In an aspect, the controllable valve of at least one of the one or more treatment agent reservoirs is at least partially opened to modulate release of the one or more treatment agents. In an aspect, the controllable valve of at least one of the one or more of the treatment agent reservoirs is at least partially closed to modulate release of the one or more treatment agents. Non-limiting examples of valves include ball valves, butterfly valves, control valves, diaphragm valves, gate valves, globe valves, plug valves, pinch valves, and needle valves. In an aspect, the at least one controllable valve is operably coupled to an actuator, e.g., a hydraulic actuator, a pneumatic actuator, an electric actuator, a piezoelectric actuator, or a mechanical actuator. In an aspect, the controllable valve releases the one or more treatment agents as a fine mist. In an aspect, the controllable valve releases the one or more treatment agents as a wet spray. In an aspect, the controllable valve releases the one or more treatment agents as a dry spray, e.g., a fine powder. In an aspect, the at least one controllable valve includes a penetrable seal, e.g., a heat-penetrable seal or a needle-penetrable seal, for single use dosing from one of one or more treatment agent reservoirs. For example, the at least one controllable valve can include a seal responsive to an electrical current. See, e.g., U.S. Pat. No. 7,070,590 to Santini et al. titled "Microchip drug delivery devices," which is incorporated herein by reference.

Conduit

A skin-treatment delivery device includes at least one conduit in fluid communication with at least one port with a controllable valve and an opening defined by a surface of the hand-held housing. The conduit forms a passageway from the at least one port of the treatment agent reservoir to a region outside the skin-treatment delivery device, e.g., in proximity to the skin surface of the individual. In an aspect, the skin-treatment delivery device is in contact with the skin surface of the individual. For example, the skin-treatment delivery device may be pushed along the skin surface of the individual while releasing the one or more treatment agents through the conduit. In an aspect, the skin-treatment delivery device is in close proximity to the skin surface of the individual. For example, the skin-treatment delivery device may be moved over the skin surface of the individual at a distance of about 0.5 to 1.0 centimeters above the skin surface while releasing one or more treatment agents through the conduit.

Figure 4:
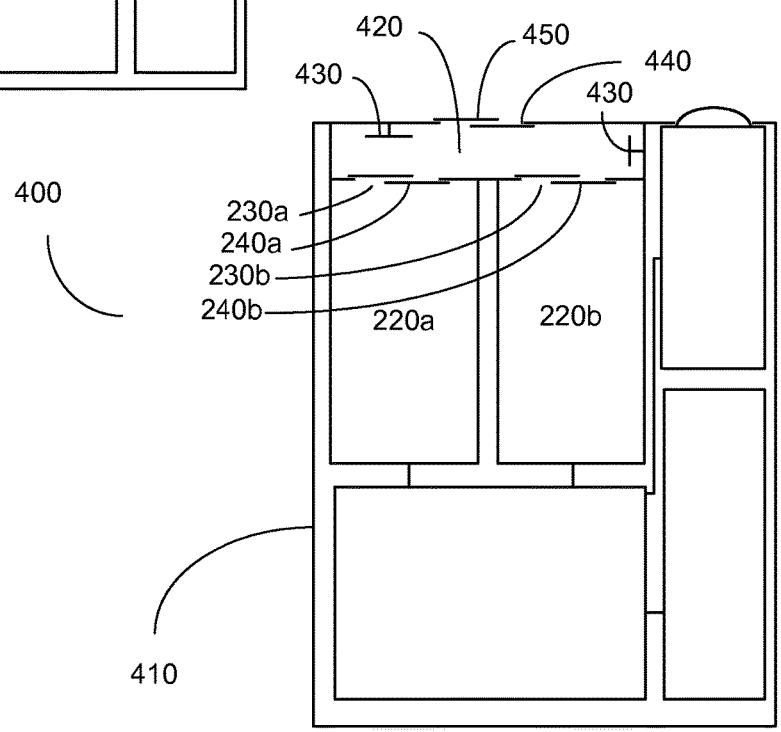
FIG. 4 is a schematic of a skin-treatment delivery device with a mixing chamber.

In an aspect, the skin-treatment delivery device includes one conduit in fluid communication with the controllable valve of each of one or more treatment agent reservoirs and an opening defined by the hand-held housing. For example, all of the treatment agent reservoirs may feed into a single conduit through which the one or more treatment agents are dispensed to the skin surface. In an aspect, the skin-treatment delivery device includes a mixing chamber including a mixing mechanism. In an aspect, the at least one conduit is in fluid communication with the mixing chamber. FIG. 4 shows a schematic of a skin-treatment delivery device including a mixing chamber fed by multiple treatment agent reservoirs and having an outlet through a common or single conduit. Skin-treatment delivery device 400 includes hand-held housing 410 sized for use with a single hand and to accommodate the components of the device. Skin-treatment delivery device 400 includes first treatment agent reservoir 220a and second treatment agent reservoir 220b. In an aspect, a skin-treatment delivery device can include more than two treatment agent reservoirs. First treatment agent reservoir 220a includes at least one port 230a with controllable valve 240a. Second treatment agent reservoir 220b includes at least one port 230b with controllable valve 240b. At least one port 230a with controllable valve 240a and at least one port 230b with controllable valve 240b are in fluid communication with mixing chamber 420. In an aspect, mixing chamber 420 is configured to serve as a chamber or holding area for combining one or more treatment agents controllably released from two or more treatment agent reservoirs. In an aspect, mixing chamber 420 includes a mixing mechanism 430. In an aspect, mixing mechanism 430 includes a rotating mixing blade. In an aspect, mixing mechanism 430 includes a vibrator that vibrates the mixing chamber to mix the one or more treatment agents. In an aspect, mixing chamber 420 forms a conduit in fluid communication with at least one port 230a with controllable valve 240a and at least one port 230b with controllable valve 240b and opening 440 defined by an outer surface of hand-held housing 410. In an aspect, the conduit formed between the mixing chamber and a space outside the device includes controllable valve 450 configured to modulate release of one or more treatment agents from mixing chamber 420.

Location-Capture Component

A skin-treatment delivery device as described herein further includes a location-capture component including circuitry configured to measure a feature of a location on a skin surface of an individual. In an aspect, the location-capture component includes circuitry to determine a location on the skin surface of an individual. In an aspect, the location-capture component measures an inherent feature of the location, e.g., a physical landmark on the skin surface of the individual. In an aspect, the one or more physical landmarks include one or more of a pigmentation, pigmented area, skin texture pattern, tattoo, blemish, scar, anatomical feature, or subsurface blood vessel on the skin surface of the individual. For example, the one or more physical landmarks can include one or more pigmented areas such as freckles or moles or one or more anatomical features such as a nose, lip, cheek, eye, brow, joint, or other anatomical features. An extensive list of landmarks of the facial area, for example, are described in Buckley et al., *Am. J. Psychiatry* (2005) 162:606-608, which is incorporated herein by reference.

In an aspect, the location-capture component measures an artificial feature of the location, e.g., one or more fiducial markers placed on the skin surface. In an aspect, the one or more fiducial markers can include one or more washable ink spots, adhesive dots or stickers, or other markings placed on the skin surface of the individual prior to measuring the locations. In an aspect, the one or more fiducial markers include one or more of radiofrequency identification (RFID) tags, electronic nodes, magnetic nodes, or audio nodes. For example, the one or more fiducial markers can include one or more RFID tags placed at various locations on a skin surface of an individual.

In an aspect, the location-capture component includes an image-capture device. In an aspect, the image-capture device is configured to capture one or more images of a location on the skin surface of the individual as the skin-treatment delivery device is moved over the skin surface. In an aspect, the location-capture component includes an image-capture device configured to capture one or more visible, infrared, or ultraviolet images of a location on the skin surface of the individual. In an aspect, the location-capture component includes at least one of a visible, infrared, ultraviolet, polarized, or spectrally limited light source. For example, the image-capture device can include one or more passive or active scanners, digital cameras, charge-coupled device (CCD), complementary metal oxide semiconductor (CMOS), infrared sensor, ultraviolet sensor, or any other device suited to capturing an image of a skin surface. Other non-limiting examples of an image-capture device include an ultrasound device, a photoacoustic device, a thermal imaging device, a capacitance measuring device, an electomyographic device, or other biomedical imaging devices.

In an aspect, the image-capture device includes at least one camera, e.g., a digital camera, configured to capture one or more images of a location on the skin surface of an individual. In an aspect, the at least one camera may capture one or more images in the visible spectrum. In an aspect, the at least one camera may capture one or more images in other portions of the electromagnetic spectrum, e.g., infrared or ultraviolet. The image-capture device can include one or more electronic image sensors, e.g., photodiodes, photoresistors, charge-coupled devices (CCD), and/or complementary metal oxide semiconductor (CMOS) devices. In an aspect, the image-capture device includes a single-shot capture device with one CCD with a Bayer filter mosaic or three separate image sensors, which are exposed to the same image via a beam splitter. In an aspect, the image-capture device includes a multi-shot capture device. For example, a single CCD sensor may obtain additive color information by capturing an image three times, each with a different filter (e.g., red, green, and blue).

In an aspect, the location-capture component includes an active scanner. An active scanner emits some form of radiation or light which when beamed onto a skin surface creates a measureable reflection. The emitted radiation or light can include electromagnetic radiation, ultrasound, or x-ray. Non-limiting examples of active non-contact scanners include hand-held laser scanners as well as a number of three-dimensional scanners (3D scanners) including time-of-flight scanners, triangulation laser scanners, structured-light scanners, and modulated light scanners. In some embodiments, the one or more active scanners can include one or more time-of-flight laser scanners in which a laser rangefinder is used to determine the distance between a surface, e.g., the one or more regions of an individual, and the laser emitter by timing the round-trip time of a pulse of light. The time-of-flight laser scanner scans the entire field of view one point at a time by changing the rangefinders view. Scanners for scanning head, face and/or whole body are commercially available (from, e.g., Cyberware, Monterery Calif.; Accurex Measurement Inc., Swathmore, Pa.; 3dMD Atlanta, Ga.; Konica/Minolta, Ramsey, N.J.)

In an aspect, the location-capture component includes a fiducial reader. In an aspect, the location-capture component includes a fiducial reader that reads one or more fiducials on the skin surface of the individual. In an aspect, the one or more fiducials are inherent properties of the skin surface, e.g., physical landmarks on the skin surface of the individual. For example, the one or more physical landmarks can include one or more of a pigmentation, pigmented area, skin texture pattern, tattoo, blemish, scar, anatomical feature, or subsurface blood vessel on the skin surface of the individual.

In an aspect, the fiducial reader reads one or more fiducial markers, e.g., spots or templates, placed on the skin surface of the individual prior to microbe profiling. For example, the fiducial reader, e.g., an image-capture device such as a digital camera, can image one or more washable ink spots, adhesive dots or stickers, or other marking agents placed on the skin surface of the individual prior to treatment with the skin-treatment delivery device. In an aspect, the one or more fiducial markers include one or more of radiofrequency identification (RFID) tags, electronic nodes, magnetic, or audio nodes. For example, the fiducial reader can include a radiofrequency antenna including circuitry to receive a radiofrequency signal from one or more RFID tags placed on the skin surface of the individual. For example, three tags can be placed on a skin surface in a triangular pattern in the area to be treated and the three tags used to triangulate the location of the skin-treatment delivery device at any given time while it is being moved over the skin surface. In an aspect, the location-capture component includes a fiducial reader that includes a receiver for signals sent from one or more fiducial markers that are electronic nodes. In an aspect, the location-capture component includes a fiducial reader that includes an audio receiver, e.g., a microphone, for signals sent from one or more fiducial markers that are audio nodes.

In an aspect, the location-capture component includes one or more receivers/transmitters for use with a local position system. For example, the location-capture component may include receivers/transmitters to receive/transmit ultrasonic or radiofrequency signals from one or more beacons to allow triangulation of the position of the skin-treatment delivery device relative to a location on the skin surface of the individual.

In an aspect, the location-capture component includes an inertial navigation device. In an aspect, the inertial navigation device includes at least one or an accelerometer, a multi-axis accelerometer, or a gyroscope. In an aspect, the inertial navigation device can include a miniaturized inertial navigation device such as describe in U.S. Patent Application 2013/0317741 to Brashear et al titled "System on a Chip Inertial Navigation System," which is incorporated herein by reference. For example, the location-capture component can include a MEMS miniature multi-axis accelerometer such as that available from Systron Donner Inertial, Concord, Calif. In an aspect, the inertial navigation device uses one or more of an accelerometer or a gyroscope to track the position of the skin-treatment delivery device relative to a known starting point on the skin surface of the individual. In an aspect, the inertial navigation device is operably coupled to the computing component to correlate an inertially determined location offset from the measured feature of the location on the skin surface of the individual with the stored information associated with the treatment map. In an aspect, the measured feature includes at least one of a pore, a mole, a hair follicle, a fiducial, a tattoo, a wrinkle, a scar, an anatomical feature, or a skin marking. For example, the inertial navigation device can be oriented relative to one or more fiducial markers placed on the skin surface of the individual. For example, the inertial navigation device can be oriented relative to one or more physical landmarks on the skin surface of the individual, e.g., one or more moles.

In an aspect, the location-capture component includes circuitry to determine the location of the one or more regions on the skin surface of the individual using triangulation, trilateration, multilateration, or a combination thereof. In an aspect, the location can be defined as coordinates. In an aspect, the coordinates for each location are further mapped to a reference image of the skin surface of the individual.

In an aspect, the location-capture component measures a feature of a location on a skin surface of an individual as the skin-treatment delivery device is moved over the skin surface. For example, the location-capture component can measure features of locations on the skin surface of an individual as a user manually moves the skin-treatment delivery device over the skin surface. For example, the location-capture component can measure features of locations on the skin surface of an individual as the skin-treatment delivery device is automatically moved in a pattern over the skin surface of the individual under control of a computing device.

Data Storage Component

A skin-treatment delivery device such as described herein includes a data storage component. In an aspect, the data storage component is configured to store information associated with a microbe profile. In an aspect, the data storage component is configured to store information associated with a treatment map. In an aspect, the data storage component includes a non-volatile data storage component. In an aspect, the data storage component includes a recordable data storage component. In an aspect, the data storage component includes a mass storage device. In an aspect, the data storage component is operably coupled to a central processing unit of the computing component through input/output channels. In an aspect, the data storage component includes data storage media. In an aspect, the data storage component is included in a hard drive of the computing component. In an aspect, the data storage component is removable. In an aspect, the data storage component includes a removable data storage component. In an aspect, the data storage component includes a removable memory card. In an aspect, the data storage component includes a removable memory stick. Non-limiting examples of removable data storage include flash memory cards, Memory Sticks, mass storage devices, CompactFlash, non-volatile memory cards, Secure Digital™ (SD) cards, miniSD cards, microSD cards, USB flash drive, or XQD cards.

Computing Component

The skin-treatment delivery device includes computing component 290 including a microprocessor. The computing component further includes circuitry configured to receive information associated with the measured feature of the location on the skin surface of the individual from the location-capture component; correlate the received information associated with the measured feature of the location on the skin surface of the individual with information stored in the data storage component; and activate the controllable valve of at least one of the one or more treatment agent reservoirs to modulate release of the one or more treatment agents onto the location on the skin surface of the individual.

The computing component includes circuitry to execute one or more instructions for operating the location-capture component, the data storage component, and the controllable valve(s). The computing component includes circuitry to execute one or more instructions for operating any or all other components incorporated into the skin-treatment delivery device, e.g., a transmission unit, a user interface, an actuation interface, a signal-generating component, or other components of the device. The computing component includes circuitry to execute one or more instructions for receiving information associated with a measured feature of a location on the skin surface of an individual from the location-capture component; one or more instructions for correlating the receive information associated with the measured feature of the location on the skin surface of the individual with information stored in the data storage component; and one or more instructions for activating the controllable valve of at least one of the one or more treatment agent reservoirs to modulate release of the one or more treatment agents onto the location on the skin surface of the individual.

In an aspect, the computing component includes a microprocessor, e.g., a central processing unit, for controlling one or more functions of the skin-treatment delivery device. The computing component further includes a system memory and a system bus that couples various system components including the system memory to the microprocessor. The microprocessor can include a processing unit, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an aspect, the computing component includes one or more ASICs having a plurality of pre-defined logic components. In an aspect, the computing component includes one or more FPGA having a plurality of programmable logic commands.

In an aspect, image-based applications such as viewers and/or toolkits (e.g., Insight Segmentation and Registration Toolkit (ITK)), are incorporated for further intake of information. In an aspect, CAD implementations, image segmentation, or other image analysis algorithms may allow processing of images received from the location-capture component.

The computing component can further include memory chips, e.g., ROM or flash memory chips, for providing storage of operating systems, look-up tables, database information, e.g., a database of treatment agents, and algorithms for comparing input data with reference data. The system memory of the computing component may include read-only memory (ROM) and random access memory (RAM). A number of program modules may be stored in the ROM or RAM, including an operating system, one or more application programs, other program modules and program data.

The computing component may further include or be capable of connecting to a flash card memory. For example, the computing device may be capable of connecting to a data storage component that is a flash card memory. The computing component may further include or be capable of connecting with a network through a network port and network interface, and through wireless port and corresponding wireless interface may be provided to facilitate communication with other peripheral devices, for example, a smart phone, a computer, a display monitor, and/or a printer.

The computing component includes computer-readable media products and may include any media that can be accessed by the computing component including both volatile and nonvolatile media, removable and non-removable media. By way of example, and not of limitation, computer-readable media may include non-transitory signal-bearing media. Non-limiting examples of non-transitory signal-bearing media include a recordable type medium such as magnetic tape, a hard disk drive, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, flash memory, magnetic tape, MINIDISC, non-volatile memory card, EEPROM, optical disk, optical storage, RAM, ROM, system memory, web server, cloud, or the like. By way of example, and not of limitation, computer-readable media may include computer storage media, e.g., magnetic tape, magnetic disk storage, optical disk storage, memory cards, flash memory cards, electrically erasable programmable read-only memory (EEPROM), solid state RAM, and solid state ROM or any other medium which can be used to store the desired information and which can be accessed by the computing component. By way of further example, and not of limitation, computer-readable media may include a communication media, e.g., wired media, such as a wired network and a direct-wired connection, and wireless media such as acoustic, RF, optical, and infrared media.

Skin-Treatment Delivery Device with Microbe Profile

Figure 5:
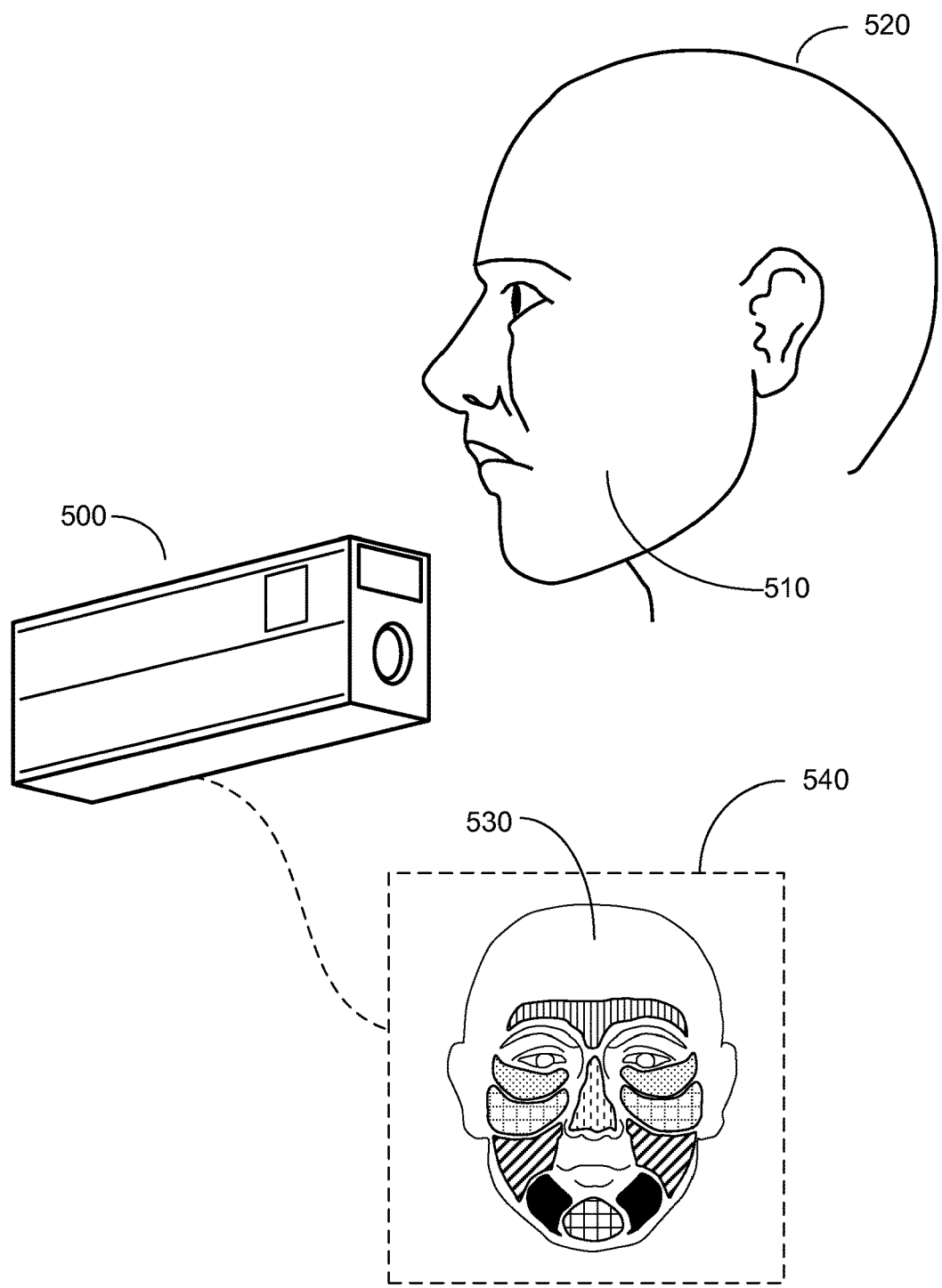
FIG. 5 is a schematic of a skin-treatment delivery device with a microbe profile.

In an aspect, a skin-treatment delivery device delivers one or more treatment agents based on a microbe profile. FIGS. 5 and 6 show aspects of a skin-treatment delivery device including stored information associated with a microbe profile. With reference to FIG. 5, skin-treatment delivery device 500 is a hand-held device configured to deliver one or more treatment agents on skin surface 510 of individual 520. Skin-treatment delivery device 500 includes circuitry to measure a feature, e.g., a physical landmark, of a location on skin surface 510 of individual 520 with a location-capture component. Skin-treatment delivery device 500 includes circuitry to compare the measured feature of the location of skin surface 510 with microbe profile 530 stored in data storage component 540 of skin-treatment delivery device 500. Microbe profile 530 includes a two-dimensional spatial distribution of one or more types of microbes at each of one or more locations on skin surface 510 of individual 520. Skin-treatment delivery device 500 further includes circuitry to modulate release of one or more treatment agents to a location on skin surface 510 of individual 520 based on the type(s) of microbe at said location.

FIG. 6 shows further aspects of a skin-treatment delivery device 500. Skin-treatment delivery device 500 includes hand-held housing 210 sized for use with one hand. Hand-held housing 210 includes one or more treatment agent reservoirs 220. Each of the one or more treatment agent reservoirs 220 is configured to store and controllably release at least one of the one or more treatment agents for application to the location on the skin surface of the individual. Treatment agent reservoir 220 includes at least one port 230 with a controllable valve 240. Hand-held housing 210 of skin-treatment delivery device 500 further includes at least one conduit 250 in fluid communication with the at least one port 230 with the controllable valve 240 and opening 260 defined by a surface of hand-held housing 210. In an aspect, skin-treatment delivery device 500 can include more than one conduit in fluid communication with multiple treatment agent reservoirs and one or more openings defined by a surface of the hand-held housing. Hand-held housing 210 of skin-treatment delivery device 500 further includes location-capture component 270 including circuitry to measure a feature, e.g., a physical landmark, of a location on the skin surface of the individual. Non-limiting examples of location-capture components have been described above herein.

Skin-treatment delivery device 500 further includes data storage component 540. Data storage component 540 is configured to store information associated with microbe profile 530, microbe profile 530 including a two-dimensional spatial distribution of one or more types of microbes at each of one or more locations on a skin surface of an individual. In an aspect, the data storage component includes circuitry to receive the information associated with the microbe profile from a remote source, e.g., from a remote computing device, a microbe profiling device, or the Internet. In an aspect, the data storage component receives the information associated with the microbe profile through a transmission unit operably coupled to the computing component. In an aspect, the data storage component receives the information associated with the microbe profile by connecting a removable data storage component, (e.g., a memory card), to a remote source, (e.g., a computing device or microbe profiling device), downloading the information, and subsequently connecting the removable data storage component to the skin-treatment delivery device.

In an aspect, data storage component 540 is incorporated into computing component 290. In an aspect, computing component 290 includes circuitry to receive the microbe profile from a remote source, e.g., a microbe profiling device, a second computing device, or through the Internet.

In an aspect, data storage component 540 is configured to store the actual microbe profile, e.g., a digital representation of the microbe profile. In an aspect, the data storage component is configured to store information on how and/or where to access the microbe profile in a remote location. For example, the data storage component may include information for accessing the microbe profile through a web connection, e.g., through the Internet. For example, the data storage component may include information for accessing the microbe profile from a second device, e.g., a microbe profiling device. In an aspect, the data storage component receives information associated with the microbe profile from one or more microbe profiling components incorporated into the skin-treatment delivery device.

Microbe profile 530 includes a two-dimensional spatial distribution of one or more types of microbes at each of one or more locations on the skin surface of the individual. In an aspect, microbe profile 530 includes a two-dimensional map of a skin surface of an individual, the two-dimensional map including the two-dimensional spatial distribution of one or more types of microbes at each of one or more locations on the skin surface of the individual. For example, the microbe profile can include a two-dimensional spatial distribution of one or more types of microbes on one or more locations on the skin surface of an individual's face. For example, the microbe profile can include a two-dimensional spatial distribution of *Propionibacterium acnes* on the skin surface of an individual's face. In an aspect, the microbe profile includes an identity of at least one of the one or more types of microbes at each of the one or more locations one the skin surface of the individual. In an aspect, the microbe profile includes a quantity of at least one of the one or more types of microbes at each of the one or more locations on the skin surface of the individual. For example, the microbe profile can include a specific number representative of the quantity of the at least one of the one or more types of microbes at each of one or more locations on the skin surface of the individual. In an aspect, the microbe profile includes a relative abundance of at least one of the one or more types of microbes at each of the one or more locations on the skin surface of the individual. For example, the microbe profile may include a color code, e.g., a gradient of color, to indicate relative abundance of the one or more types of microbes on the skin surface of the individual. In an aspect, the information associated with the microbe profile is updateable. For example, the information associated with the microbe profile may be updated when a new microbe profile is acquired. For example, the information associated with the microbe profile may be updated to add or subtract information, e.g., the quantity, relative abundance, or the identity of one or more of the one or more types of microbes in the microbe profile.

In an aspect, the microbe profile is personalized for the individual. In an aspect, the microbe profile for a given individual is generated using a microbe profiling device. In an aspect, the microbe profiling device can include a mask that is placed over a skin surface to sample the microbes as described in U.S. patent application Ser. No 13/975,055, which is incorporated herein by reference. In an aspect, the microbe profiling device can include a hand-held device such as described in U.S. patent application Ser. Nos. 14/091,762 and 14/091,832, which are incorporated herein by reference. In an aspect, the microbe profile is received from the microbe profiling device through a wired communication. In an aspect, the microbe profile is received from the microbe profiling device through a wireless communication. In an aspect, the microbe profile is received from the microbe profiling device through a form of media, e.g., a flash drive, or other means of transferring data. In an aspect, the microbe profile is received from the microbe profiling device through the Internet or other web-based communication link. In an aspect, the skin-treatment delivery device includes one or more microbe profiling components configured to generate a microbe profile for the individual.

In an aspect, the data storage component is configured to store information associated with a microbe profile that is not the individual's microbe profile. In an aspect, the microbe profile is an idealized microbe profile, e.g., the microbe profile of an individual with desirable skin qualities. In an aspect, the microbe profile is a normalized microbe profile, e.g., a healthy microbe profile. In an aspect, the microbe profile is generalized from a population of individuals. For example, the microbe profile can be generalized from a population of individuals of a given age or age range. For example, the microbe profile can be generalized from a population of individuals of the same gender. For example, the microbe profile can be generalized from a population of individuals of the same ethnicity. For example, the microbe profile can be generalized from a population of individuals in a specific region of the world.

In an aspect, the microbe profile includes a feature map of the skin surface of the individual. In an aspect, the feature map is representative of the skin surface of the individual. In an aspect, the feature map of the skin surface of the individual includes one or more images of the skin surface of the individual. For example, the microbe profile can include one or more images of the skin surface of the individual overlaid with a color coded two-dimensional spatial distribution of the one or more types of microbes on the skin surface of the individual. In an aspect, the feature map of the skin surface of the individual includes one or more fiducial markers on the skin surface of the individual. For example, the microbe profile can include a map, pattern, or grid of fiducial markers on the skin surface of the individual overlaid with a color coded two-dimensional spatial distribution of the one or more types of microbe on the skin surface of the individual. In an aspect, the one or more fiducial markers are physical landmarks, e.g., moles or freckles, on the skin surface of the individual. In an aspect, the one or more fiducial markers are artificial landmarks, e.g., optical, RFID, magnetic, audio, or electronic tags, placed on the skin surface of the individual as reference. In an aspect, the feature map of the skin surface of the individual includes one or more coordinates representative of locations on the skin surface of the individual. For example, the microbe profile includes a series or grid of coordinates, e.g., x-y coordinates, overlaid with a coded two-dimensional spatial distribution of the one or more types of microbes on the skin surface of the individual.

Referring back to FIG. 6, skin-treatment delivery device 500 further includes computing component 290 including a processor. Computing component 290 is operably coupled to controllable valve 240, location-capture component 270, and data storage component 540. Computing component 290 of skin-treatment delivery device 500 includes circuitry 600. Circuitry 600 includes circuitry 610 to receive information associated with the measured feature of the location of the skin surface of the individual from the location-capture component 270; circuitry 620 to correlate the received information associated with the measured feature of the location on the skin surface of the individual with the stored information associated with the microbe profile 530 to determine a presence of at least one of the one or more types of microbes at said location; circuitry 630 to select one or more treatment agents for application to the location on the skin surface of the individual from a database of treatment agents based on the presence of the at least one of the one or more types of microbes at said location; and circuitry 640 to actuate controllable valve 240 of at least one of the one or more treatment agent reservoirs 220 to modulate release of the selected one or more treatment agents onto said location on the skin surface of the individual.

Skin-treatment delivery device 500 includes circuitry 610 to receive information associated with the measured feature of the location on the skin surface of the individual. In an aspect, the computing component includes circuitry to receive the information associated with the measured feature of the location on the skin surface of the individual from an image-capture device, e.g., a visible, infrared, or ultraviolet camera. In an aspect, the computing component includes circuitry to receive information associated with one or more images of the location on the skin surface of the individual. For example, the computing component can include circuitry to receive one or more visible, infrared, or ultraviolet images of the location on the skin surface of the individual. In an aspect, the computing component includes circuitry to receive the information associated with the measured feature of the location on the skin surface of the individual from a fiducial reader, e.g., an image-capture device, electronic reader, magnetic reader, acoustic reader, or RFID tag reader. In an aspect, the computing component includes circuitry to receive information associated with one or more fiducial markers of the location on the skin surface of the individual. For example, the computing component can include circuitry to receive information associated with one or more physical markers, e.g., freckles or other skin features, or artificial markers, e.g., RFID tags, optical markers, magnetic markers, electronic markers, or acoustic markers, placed on the skin surface of the individual. In an aspect, the computing component can include circuitry to receive information associated with one or more coordinates representative of the location on the skin surface of the individual. For example, the computing component can include circuitry to receive one or more coordinates from an inertial navigation device.

Skin-treatment delivery device 500 includes circuitry 620 to correlate the received information associated with the measured feature of the location on the skin surface of the individual with the stored information associated with the microbe profile 530 to determine a presence of at least one of the one or more types of microbes at said location. In an aspect, skin-treatment delivery device 500 includes circuitry to align the measured feature of the location on the skin surface of the individual with features of one or more locations on a feature map of the skin surface of the individual embedded in microbe profile 530. For example, the microbe profile including the spatial distribution and identity of one or more types of microbes on the skin surface of the individual can be overlaid with a feature map, e.g., an image map, a fiducial map, and/or a coordinate map. For example, the microbe profile can consist of a series of colors representative of the spatial distribution of the one or more types of microbes overlaid on a feature map, e.g., one or more images of the skin surface of the individual. In an aspect, the computing component includes circuitry to align one or more images of the location on the skin surface of the individual with images of one or more locations on the feature map of the skin surface of the individual embedded in the microbe profile. In an aspect, the computing component includes circuitry to align one or more fiducial markers of the location on the skin surface of the individual with fiducial markers of one or more locations on the feature map of the skin surface of the individual embedded in the microbe profile. In an aspect, the computing component includes circuitry to align one or more coordinates of the location on the skin surface of the individual with coordinates of one or more locations on the feature map of the skin surface of the individual embedded in the microbe profile.

In an aspect, skin-treatment delivery device 500 includes circuitry configured to access one or more algorithms for aligning the measured feature of the location on the skin surface of the individual with features of one or more locations on a feature map embedded in the microbe profile. For example, the computing component can include circuitry to align one or more images of the location on the skin surface of the individual with a feature map, e.g., a large reference image, of the skin surface of the individual. In an aspect, the feature map can include one or more visual, infrared, or ultraviolet images covering at least the area of the skin surface covered by the microbe profile. In an aspect, the feature map can include a series, e.g., a grid of fiducial markers or coordinates associated with specific locations on the skin surface of the individual. In an aspect, the computing component may include circuitry to align one or more images of the location on the skin surface of the individual with the feature map of the skin surface based on aligning one or more physical landmarks, e.g., one or more of pigmentation, pigmented areas, tattoos, skin texture patterns, blemishes, scars, anatomical features, or subsurface blood vessels.

In an aspect, the computing component includes circuitry to align the one or more images, fiducial markers, or coordinates of the location on the skin surface of the individual with the one or more features of the feature map of the skin surface using any of a number of image registration algorithms, programs, or software. In an aspect, the computing component includes circuitry configured to detect one or more features depicted in the one or more images, e.g., the physical landmarks, and match these features with features in the reference image. Features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. The computing component is further operable to match the features detected in the one or more images of skin surface of the individual with features in the reference image using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods. The following references are incorporated by reference and include descriptions of computational methods for image registration: Szeliski *Foundations and Trends in Computer Graphics and Vision*, Vol. 2, No. 1 (2006) 1-104, Zitova & Flusser *Image Vision Computing* (2003) 21:977-1000.

Skin-treatment delivery device 500 includes circuitry 630 to select one or more treatment agents for application to the location on the skin surface of the individual from a database of treatment agents based on the presence of the at least one of the one or more types of microbes at said location. In an aspect, the database of treatment agents is stored in data storage component 540. In an aspect, the database of treatment agents reflects the one or more treatment agents available for use with skin-treatment delivery device 500. In an aspect, the database of treatment agents includes at least the one or more treatment agents in the one or more treatment agent reservoirs 220. In an aspect, the database of treatment agents is updateable. For example, the database of treatment agents can be updated to add or subtract one or more treatment agents. For example, the database of treatment agents can be updated to reflect the one or more treatment agents currently present in the one or more treatment agent reservoirs of the skin-treatment delivery device. For example, each removable treatment agent reservoir may include a code, e.g., a bar code, including information to update the database of treatment agents. For example, updates to the database of treatment agents may reflect changes in the treatment map and/or the microbe profile of the individual. In an aspect, the database of treatment agents includes a look-up table including one or more treatment agents matched with one or more types of microbes. In an aspect, the database of treatment agents includes information associated with one or more treatment agents matched with information associated with one or more types of microbes. In an aspect, the skin-treatment delivery device includes circuitry to alert a user if the one or more treatment agents selected from the database of treatment agents are not currently available in the one or more treatment agent reservoirs. In an aspect, the skin-treatment delivery device includes circuitry to alert the user to change and/or replace one or more treatment agent reservoirs to include one or more treatment agent reservoirs including the selected one or more treatment agents.

Skin-treatment delivery device 500 includes circuitry 640 to actuate the controllable valve of at least one of the one or more treatment agent reservoirs to modulate release of the selected one or more treatment agents onto said location on the skin surface of the individual. In an aspect, circuitry 640 includes circuitry to at least partially open or at least partially close the controllable valve of at least one of the one or more treatment agent reservoirs to modulate release of the selected one or more treatment agents.

In an aspect, the computing component of skin-treatment delivery device 500 includes circuitry to store delivery data. In an aspect, the delivery data is stored in data storage component 540 of skin-treatment delivery device 500. In an aspect, the delivery data includes at least one of a treatment agent, a dose, a skin-surface location, a time, or a date. For example, at each location, delivery data associated with the type and amount of treatment agent can be stored. In an aspect, computing component of skin-treatment delivery device 500 includes circuitry to report the delivery data to a user. In an aspect, the user includes the individual being treated. In an aspect, the user includes a medical practitioner or other practitioner. In an aspect, the user includes a commercial entity, e.g., the manufacturer of the skin-treatment delivery device or the manufacturer of the one or more treatment agents. In an aspect, the computing component of skin-treatment delivery device 500 includes circuitry to retrieve previously stored delivery data to inform delivery of one or more treatment agents in the future. In an aspect, skin-treatment delivery device 500 includes circuitry to manually actuate the controllable valve at specific locations to deliver one or more treatment agents and to collect delivery data for each of the specific locations, e.g., what was delivered, how much, and when. In an aspect, the computing component of skin treatment-delivery device 500 includes circuitry to convert the delivery data into a treatment map.

Skin-Treatment Delivery Device with Treatment Map

Figure 7:
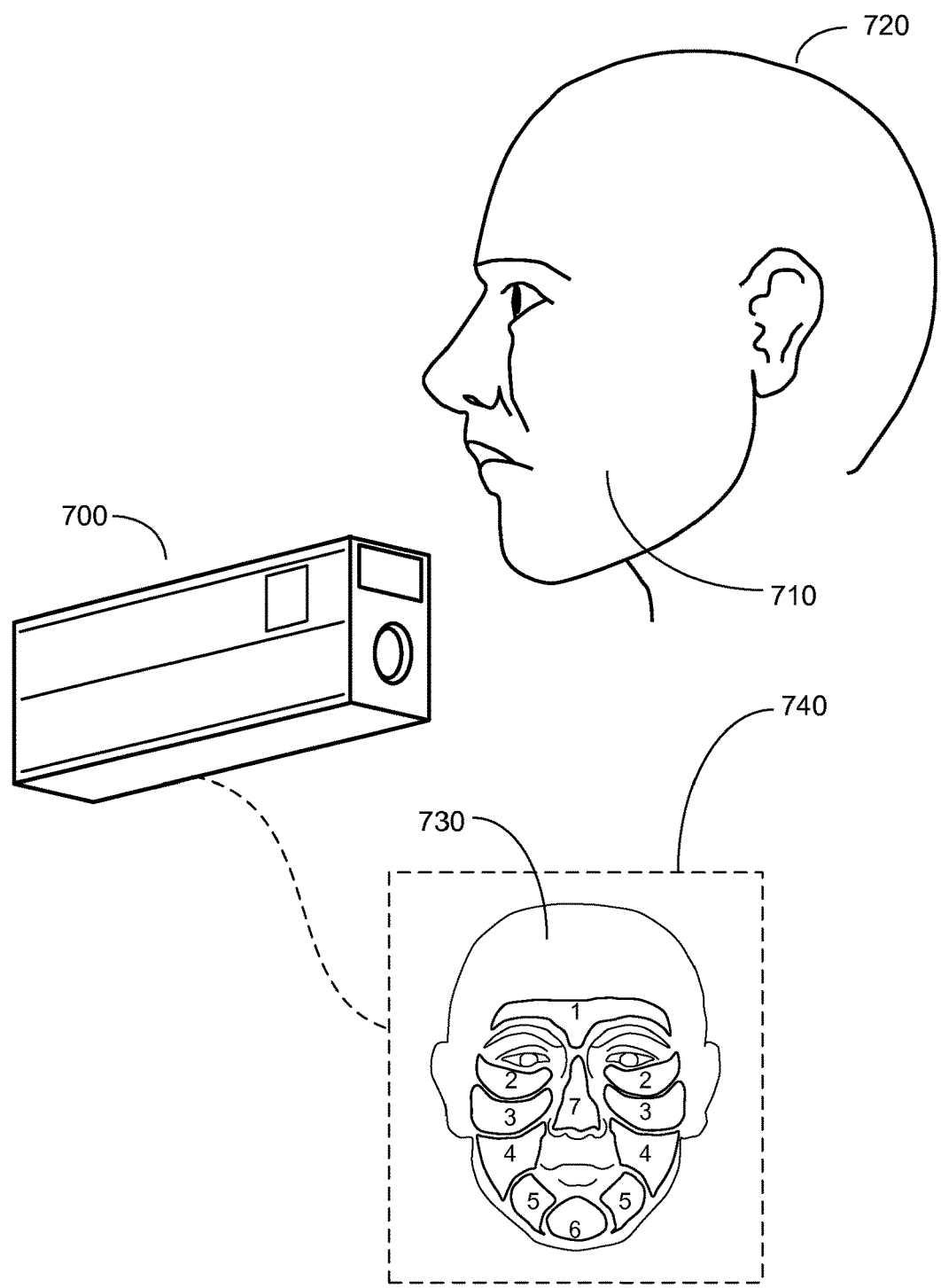
FIG. 7 is a schematic of a skin-treatment delivery device with a treatment map.

In an aspect, a skin-treatment delivery device delivers one or more treatment agents based on a treatment map. FIGS. 7 and 8 show aspects of a skin-treatment delivery device including stored information associated with a treatment map. With reference to FIG. 7, skin-treatment delivery device 700 is a hand-held device configured to deliver one or more treatment agents to skin surface 710 of individual 720. Skin-treatment delivery device 700 includes a location-capture component including circuitry to measure a feature, e.g., a physical landmark, of a location on skin surface 710 of individual 720 with a location-capture component. Skin-treatment delivery device 700 includes circuitry to compare the measured feature of the location of skin surface 710 with treatment map 730 stored in data storage component 740 of skin-treatment delivery device 700. Treatment map 730 includes a two-dimensional spatial distribution of one or more treatment agents for application to skin surface 710 of individual 720. Skin-treatment delivery device 700 further includes circuitry to modulate release of one or more treatment agents to a location on skin surface 710 of individual 720 based on the treatment specified by the treatment map at said location.

FIG. 8 shows further aspects of a skin-treatment delivery device 700. Skin-treatment delivery device 700 includes hand-held housing 210 sized for use with one hand. Hand-held housing 210 includes one or more treatment agent reservoirs 220. In an aspect, each of the treatment agent reservoirs 220 is configured to store and controllably release at least one of the one or more treatment agents for application to the skin surface of the individual. In an aspect, at least one first treatment agent reservoir is configured to store and controllably release at least one treatment agent of a first type and at least one second treatment agent reservoir is configured to store and controllably release at least one treatment agent of a second type. In an aspect, the one or more treatment agent reservoirs include a replaceable cartridge. Non-limiting examples of treatment reservoirs and treatment agents have been described above herein. Treatment agent reservoir 220 includes at least one port 230 with a controllable valve 240. Hand-held housing 210 of skin-treatment delivery device 700 further includes at least one conduit 250 in fluid communication with at least one port 230 with controllable valve 240 and opening 260 defined by a surface of hand-held housing 210. In an aspect, skin-treatment delivery device 700 can include one or more conduits in fluid communication with multiple treatment agent reservoirs and one or more openings defined by a surface of the hand-held housing. Hand-held housing 210 of skin-treatment delivery device 700 further includes location-capture component 270 including circuitry to measure a feature, e.g., a physical landmark, of a location on the skin surface of the individual. In an aspect, the location-capture component includes at least one of an image capture device, a fiducial reader, or an inertial navigation device. Non-limiting examples of location-capture components have been described above herein.

Skin-treatment delivery device 700 further includes data storage component 740. Data storage component 740 is configured to store information associated with treatment map 730, treatment map 730 including a two-dimensional spatial distribution of one or more treatment agents for application to the skin surface of the individual. In an aspect, data storage component 740 includes non-volatile memory. In an aspect, data storage component 740 includes a recordable data storage component. In an aspect, data storage component 740 is removable. For example, the data storage component can include a medium that is inserted into a docking site, e.g., a USB port or other connection port, of the skin-treatment delivery device. In an aspect, data storage component 740 includes a removable memory card. In an aspect, data storage component 740 includes a removable memory stick. In an aspect, data storage component 740 is incorporated into the computing component. Non-limiting examples of data storage components have been described above herein.

Data storage component 740 of device 700 is configured to store information associated with treatment map 730. Treatment map 730 includes a two-dimensional spatial distribution of one or more treatment agents for application to the skin surface of the individual. In an aspect, treatment map 730 includes a two-dimensional spatial distribution of one or more probiotics for application to the skin surface of the individual. In an aspect, treatment map 730 includes a two-dimensional spatial distribution of one or more prebiotics for application to the skin surface of the individual. In an aspect, treatment map 730 includes a two-dimensional spatial distribution of at least one of an antimicrobial agent, a therapeutic agent, or a chemotherapeutic agent. In an aspect, treatment map 730 can include one or more probiotics, prebiotics, antimicrobial agents, therapeutic agents, chemotherapeutic agents, or combinations thereof. In an aspect, treatment map 730 can include one or more other agents, e.g., moisturizers, anti-aging agents, sunscreens, and the like. Non-limiting examples of treatment agents have been described above herein.

In an aspect, treatment map 730 corresponds to a microbe profile, the microbe profile including a two-dimensional spatial distribution of one or more types of microbes on the skin surface of the individual. In an aspect, the two-dimensional spatial distribution of the one or more treatment agents for application to the skin surface of the individual overlaps a two-dimensional spatial distribution of one or more microbes on the skin surface of the individual. In an aspect, the treatment map provides a "road map" for treating the skin surface of the individual at any given location based on the types and abundance of microbes at that given location. In an aspect, the skin-treatment delivery device and associated components and circuitry automatically release one or more treatment agents at a given location based on correlating said location with the treatment map. For example, the type and quantity of microbes at a specific location on the skin surface of the individual dictates the corresponding treatment agent to be used at that specific location. For example, the skin surface of the cheeks of an individual may include a first type of microbe to be treated with a first type of treatment agent and the skin surface of the forehead of the individual may include a second type of microbe to be treated with a second type of treatment agent. In an aspect, information associated with the type and quantity of microbes at a specific location on the skin surface of the individual is derived from a microbe profile. In an aspect, the treatment map is a personalized map based on a personalized microbe profile. For example, the treatment map, i.e., the spatial map of treatment application at one or more locations on the skin surface of the individual, may be generated based on the identity and spatial distribution of one or more types of microbes at said one or more locations on the skin surface of the individual. In an aspect, the treatment map is a personalized map based on a generalized microbe profile. For example, the treatment map may be based on a generalized microbe profile of a specific population, e.g., a teen population, and include one or more generalized treatment agents for a specific condition, e.g., anti-acne agents, as well as one or more personalized treatment agents based on the individual's specific microbe profile. In an aspect, the treatment map is based on an idealized microbe profile, e.g., the microbe profile of an individual(s) with desirable skin qualities. In an aspect, the treatment map is based on a normalized microbe profile, e.g., a healthy microbe profile. In an aspect, the treatment map is based on a generalized microbe profile from a population of individuals of the same gender, ethnicity, and/or geographical location.

In an aspect, treatment map 730 includes a feature map of the skin surface of the individual. In an aspect, a measured feature, e.g., an image, a fiducial marker, or a coordinate, of a location on the skin surface of the individual is mapped to the feature map embedded in the treatment map. In an aspect, the feature map of the skin surface of the individual includes one or more images of the skin surface of the individual. For example, the treatment map including the spatial distribution of one or more treatment agents for application to locations on the skin surface of the individual can be overlaid on one or more images of said locations on the skin surface of the individual. In an aspect, the feature map of the skin surface of the individual includes one or more fiducial markers on the skin surface of the individual. For example, the treatment map including the spatial distribution of one or more treatment agents for application to locations on the skin surface of the individual can be overlaid on one or more fiducial markers, e.g., physical landmarks or artificial tags, of said locations on the skin surface of the individual. In an aspect, the feature map of the skin surface of the individual includes one or more coordinates of the skin surface of the individual. For example, the treatment map including the spatial distribution of one or more treatment agents for application to locations on the skin surface of the individual can be overlaid on a coordinate grid of said locations on the skin surface of the individual.

In an aspect, treatment map 730 is updateable. For example, the treatment map may be updated to add or subtract one or more treatment agents. For example, the treatment map may be updated to change the application location of one or more treatment agents. In an aspect, the treatment map is updated in response to changes in the microbe profile of the individual. For example, the treatment map may be altered in response to changes in the microbe profile due to the onset or resolution of a microbial infection or other skin condition. For example, the treatment map may be updated in response to changes in the microbe profile as a result of previous treatment with one or more treatment agents. In an aspect, updates to the treatment map are directly written to the data storage component. In an aspect, updates to the treatment map are wirelessly transmitted to the data storage component.

In an aspect, data storage component 740 includes circuitry to receive treatment map 730 generated within the computing component of the skin-treatment delivery device based on a microbe profile. In an aspect, data storage component 740 includes circuitry to receive treatment map 730 from a remote source. In an aspect, data storage component 740 includes circuitry to receive treatment map 730 from a remote computing device. For example, a data storage component can include circuitry to receive a wireless transmission including the treatment map from a computing device located in the office of a medical practitioner or other practitioner. For example, a removable data storage component, e.g., a memory card or stick, can include circuitry to directly write the treatment map from the remote computing device. In an aspect, data storage component 740 includes circuitry to receive treatment map 730 from a microbe profiling device. For example, the data storage component can include circuitry to receive a wireless transmission including the treatment map from a separate microbe profiling device. For example, a removable data storage component, e.g., a memory card or stick, can include circuitry to directly write the treatment map from the microbe profiling device. In an aspect, data storage component 740 includes circuitry to receive the treatment map through the Internet.

Skin-treatment delivery device 700 includes computing component 290 including circuitry 800. Circuitry 800 includes circuitry 810 to receive information associated with the measured feature of the location on the skin surface of the individual from location-capture component 270; circuitry 820 to correlate the received information associated with the measured feature of the location on the skin surface of the individual with the stored information associated with treatment map 730 to select the one or more treatment agents for application at said location on the skin surface of the individual; and circuitry 830 to actuate the controllable valve 240 of at least one of the one or more treatment agent reservoirs 220 to modulate release of the selected one or more treatment agents for application at said location on the skin surface of the individual.

In an aspect, circuitry 800 of skin-treatment delivery device 700 includes circuitry to receive the information associated with the measured feature of the skin surface of the individual from an image capture device, e.g., a digital camera. In an aspect, circuitry 800 of skin-treatment delivery device 700 includes circuitry to receive the information associated with the measured feature of the skin surface of the individual from a fiducial reader, e.g., a magnetic, electronic, or RFID tag reader. In an aspect, the information associated with the measured feature of the location on the skin surface of the individual includes information associated with one or more images of the location on the skin surface of the individual. In an aspect, the information associated with the measured feature of the location on the skin surface of the individual includes information associated with one or more fiducial markers of the location on the skin surface of the individual. In an aspect, the information associated with the measured feature of the location on the skin surface of the individual includes information associated with one or more coordinates representative of the location on the skin surface of the individual.

In an aspect, circuitry 800 of skin-treatment delivery device 700 includes circuitry to align the measured feature of the location on the skin surface of the individual with features of one or more locations of the individual incorporated into the treatment map. For example, the circuitry can include circuitry to align the measured feature of the location on the skin surface of the individual with a feature map embedded, e.g., overlaid on, the treatment map. In an aspect, circuitry 800 includes circuitry to align one or more images of the location on the skin surface of the individual with images of one or more locations on the skin surface of the individual incorporated into the treatment map. In an aspect, circuitry 800 includes circuitry to align one or more fiducial markers of the location on the skin surface of the individual with fiducial markers of one or more locations on the skin surface of the individual incorporated into the treatment map. In an aspect, circuitry 800 includes circuitry to align one or more coordinates of the location on the skin surface of the individual with coordinates of one or more locations on the skin surface of the individual incorporated into the treatment map.

In an aspect, the computing component of skin-treatment delivery device 700 includes circuitry to store delivery data. In an aspect, the delivery data is a record of the treatment applied at any given location. In an aspect, delivery data includes at least one of a treatment agent, a dose, a location, a time, or a date. In an aspect, the delivery data is stored in data storage component 740. In an aspect, the computing component of skin-treatment delivery device 700 includes circuitry to report the delivery data to a user. In an aspect, the computing component of skin-treatment delivery device 700 includes circuitry to convert the delivery data into a treatment map. For example, the treatment map can be generated de novo from delivery data obtained while manually delivering one or more treatment agents to the skin surface of the individual. For example, the delivery data can be recorded, e.g., to the data storage component, as a user, e.g., a medical practitioner, moves the skin-treatment delivery device over the skin surface of the individual and manually actuates the controllable valve of at least one of the one or more treatment agent reservoirs. The delivery data can include the name of the one or more treatment agents delivered, the location on the skin surface of the delivery, the dosage, and the date and time of day. For example, the delivery data recorded by the skin-treatment delivery device while being operated by the medical practitioner can be converted to a treatment map and stored in the data storage component of the device for future reference when using the skin-treatment delivery device. For example, the delivery data recorded by the skin-treatment delivery device while being operated by the medical practitioner can be converted to a treatment map and stored on a removable data storage component, e.g., a memory card, which can be inserted into a home version of the skin-treatment delivery device for use at a later date by the individual. In an aspect, the computing component of skin-treatment delivery device 700 includes circuitry to update the treatment map based on the delivery data.

In an aspect, skin-treatment delivery device 700 includes circuitry to at least partially open the controllable valve of at least one of the one or more treatment agent reservoirs to modulate release of the one or more treatment agents. In an aspect, skin-treatment delivery device 700 includes circuitry to at least partially close the controllable valve of at least one of the one or more treatment agent reservoirs to modulate release of the one or more treatment agents.

Other Components of a Skin-Treatment Delivery Device

Figure 9:
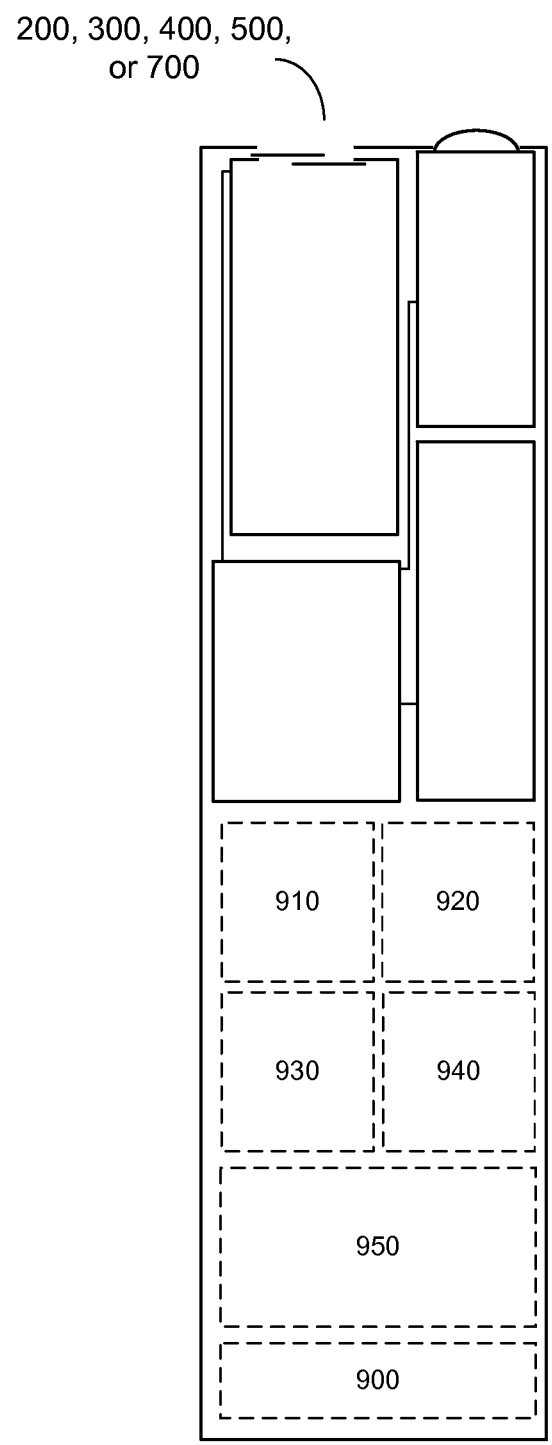
FIG. 9 is a schematic showing further aspects of a skin-treatment delivery device such as shown in FIG. 2.

A skin-treatment delivery device, non-limiting examples of which have been described in FIGS. 1-8, can include additional components. FIG. 9 shows further aspects of a skin-treatment delivery device, e.g., skin-treatment delivery device 200, 300, 400, 500, or 700, with one or more components in addition to the components previously described, e.g., a hand-held housing, one or more treatment agent reservoirs, at least one port with a controllable valve for each of the one or more treatment agent reservoirs, at least one conduit, a location-capture component, a data storage component, and a computing component with a processor and circuitry.

In an aspect, a skin-treatment delivery device can include power source 900 to power one or more components of the skin-treatment delivery device. In an aspect, the power source includes one or more batteries. In an aspect, the one or more batteries include one or more disposable batteries, e.g., cells, buttons, thin-film batteries, or microbatteries. For example, the components of the skin-treatment delivery device can be powered by a conventional battery, e.g., a disposable 9 volt battery. Non-limiting examples of disposable batteries include zinc-carbon, alkaline, lithium, zinc-chloride, zinc-air, or silver-oxide batteries. In an aspect, the one or more batteries include one or more rechargeable batteries. For example, the components of the skin-treatment delivery device can be powered by one or more rechargeable lithium-ion batteries. Non-limiting examples of rechargeable batteries include nickel-cadmium, nickel-zinc, nickel metal hydride, silver-zinc, or lithium ion. In an aspect, the components of the skin-treatment delivery device are powered through kinetic energy, which may include stored kinetic energy.

In an aspect, the components of the skin-treatment delivery device are powered through an electrical cord accessing power through a common electrical output/socket, a USB port, a line connector, or a plug for a car cigarette lighter outlet.

In an aspect, the skin-treatment delivery device includes user interface 910. In an aspect, the user interface is operably coupled to computing component 290. User interface 910 includes one or more input components and/or output components for use by a user to interface with the skin-treatment delivery device. The one or more input components can be used to enter information into the skin-treatment delivery device, e.g., patient information, operating instructions, or treatment regimen, and may be integrated into the skin-treatment delivery device or may be one or more peripheral devices operably connected through a wired or wireless connection to the skin-treatment delivery device. Non-limiting examples of input components include a graphical user interface, a display, a keyboard, a keypad, a touch-screen, a microphone, a stylus pen, a switch, a dial, or the like. In some embodiments, the user interface is user driven. For example, the user inputs data or operating conditions into the skin-treatment delivery device using the user interface, e.g., a touch-screen. In some embodiments, the user interface, e.g., a switch, is circuitry driven. For example, an on/off switch may be toggled based on proximity of a portion of the skin-treatment delivery device to the skin surface of an individual.

The user interface includes one or more output components over which processed information is viewed as output results and may be integrated into the skin-treatment delivery device or may be one or more peripheral devices operably connected through a wired or wireless connection to the skin-treatment delivery device. For example, the user interface may be used to report to a user a microbe profile, a treatment map, recorded delivery data, or retrieved delivery data. For example, the user interface may be used to inform the use of the skin-treatment delivery device. In an aspect, the skin-treatment delivery device includes a display incorporated into the hand-held housing, the display including circuitry to display at least one of the microbe profile, the treatment map, the feature map, or a combination thereof. For example, a display showing a microbe profile or a treatment map overlaid on a feature map of the skin surface of the individual can inform the user as to where treatment should be initiated or to where the device should be moved next. Non-limiting examples of output components include but are not limited to television screens, computer monitors, liquid crystal displays, audio speakers, audio headphones, and printers.

In an aspect, the one or more input/output components are connected to the processor of the computing component through one or more user input interfaces that are coupled to the system bus, but may be connected by other interfaces and bus structures, such as a parallel port, game port, or a universal serial bus (USB). For example, external input components or output components may be connected to the processor through a USB port.

In an aspect, a skin-treatment delivery device includes actuation interface 920. In an aspect, a skin-treatment delivery device includes an actuation interface accessible on an outer surface of the hand-held housing, the actuation interface including circuitry to transmit one or more signals to the computing component. In an aspect, the actuation interface allows a user to manually actuate the controllable valve of at least one of the one or more treatment agent reservoirs. In an aspect, the actuation interface includes at least one of a switch, a button, or a toggle. For example, the skin-treatment delivery device can include a button that the user can push to manually actuate the controllable valve of at least one of the one or more treatment agent reservoirs. In an aspect, the actuation interface includes a microphone. For example, the skin-treatment delivery device can include a microphone into which a user can vocalize a command to manually actuate the controllable valve of at least one of the one or more treatment agent reservoirs. In an aspect, the actuation interface includes circuitry to transmit one or more signals to the computing component of the skin-treatment delivery device. In an aspect, the computing component of the skin-treatment delivery device includes circuitry to actuate the controllable valve of at least one of the one or more treatment agent reservoirs in response to one or more signals received from the actuation interface.

In an aspect, the skin-treatment delivery device includes a signal-generating component 930. In an aspect, the signal-generating component includes an optical signal-generating component. For example, the signal-generating component can include a light source, e.g., a small light emitting diode (LED), which lights up, flashes, or otherwise signals the user. In an aspect, the signal-generating component includes an audible signal-generating component. For example, the signal-generating component can include a small speaker that emits an audible noise, e.g., a beep, in response to a signal from an audio chip. In an aspect, the signal-generating component includes a haptic signal-generating component. For example, the signal-generating component can include an element that vibrates in response to input from the computing component. For example, the haptic signal-generating component can include a vibrotactor with an eccentric mass on a small motor or a moving mass on a coil actuator. For example, the haptic signal-generating component can include piezoelectric materials or electroactive polymers. Vibrating elements, e.g., tactors, are available from commercial sources (from, e.g., Engineering Acoustics, Inc., Winter Park, Fla.).

In an aspect, the signal-generating component is operably coupled to the computing component of the skin-treatment delivery device and is configured to emit one or more signals in response to receiving input, e.g., one or more signals, from the operably coupled computing component. In an aspect, the signal-generating component includes circuitry to emit one or more signals based upon proximity of the skin-treatment delivery device to a treatment location associated with the microbe profile and/or treatment map. For example, the signal-generating component can be configured to emit one or more signals when alerted by the computing component that the current location detected on the skin surface is outside the region of skin surface defined by the microbe profile. For example, the signal-generating component can be configured to emit one or more signals when alerted by the computing component that the current location detected on the skin surface is outside the region of skin surface defined by the treatment map. In an aspect, the signal-generating component includes circuitry to emit one or more signals in response to completion of delivery of the one or more treatment agents at a treatment location associated with the microbe profile and/or treatment map. For example, the signal-generating component can emit one or more signals indicating that treatment at the location on the skin surface of the individual is complete and that the skin-treatment delivery device can be moved to a new location on the skin surface of the individual.

In an aspect, the signal-generating component is used in conjunction with an actuation interface to manually actuate a controllable valve of at least one of the one or more treatment agent reservoirs. For example, the signal-generating component can be configured to emit one or more signals to indicate that a location has been reached on the skin surface and that the user should engage an actuation interface, e.g., push a button, to actuate the controllable valve of at least one of the one or more treatment agent reservoirs. For example, the signal-generating component can be configured to emit one or more signals to indicate completion of treatment at the location on the skin surface of the individual and to indicate that the user should disengage the actuation interface, e.g., stop pushing the button, and move the skin-treatment delivery device to a new location on the skin surface of the individual.

In an aspect, a skin-treatment delivery device can include transmission unit 940. In an aspect, the transmission unit is operably coupled to the computing component of the skin-treatment delivery device and includes an antenna. In an aspect, the transmission unit includes circuitry to receive at least one of the microbe profile, the treatment map, or delivery data from a remote device. In an aspect, the transmission unit includes circuitry to transmit at least one of the microbe profile, the treatment map, or the delivery data to a remote device. In an aspect, the remote device includes a remote computing device, e.g., a desktop, laptop, or tablet computer. In an aspect, the remote device includes a personal communication device, e.g., a cellular phone or smart phone device. In an aspect, the remote device includes a microbe profiling device. A "transmission unit," as used herein, can be one or more of a variety of units that are configured to send and/or receive signals, such as signals carried as electromagnetic waves. A transmission unit generally includes at least one antenna and associated circuitry. A transmission unit can include a transmitter and a receiver. A transmission unit can include volatile or non-volatile memory. A transmission unit can include a processor and/or be operably connected to a processor. A transmission unit can be operably connected to an energy source, such as a battery. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit can include an oscillator and encoder configured to generate a programmable pulse position-modulated signal in the radio frequency range (see, e.g., U.S. Pat. No. 4,384,288, which is incorporated herein by reference). A transmission unit can include a radio frequency identification device (RFID), which can be a passive RFID device, a semi-passive RFID device, or an active RFID device, depending on the embodiment (see, e.g., Chawla & Ha, "An Overview of Passive RFID," *IEEE Applications and Practice,* 11-17 (September 2007), which is incorporated herein by reference). A transmission unit including an RFID device can be configured to transmit signals in the UHF standard range. A transmission unit can include a battery-assisted passive RFID device, such as sold by Alien Technology®, Morgan Hill, Calif. A transmission unit can include an optical transmission unit. A transmission unit can include a hybrid backscatter system configured to function in an RFID, IEEE 802.11x standard and Bluetooth system (see, e.g., U.S. Pat. No. 7,215,976, which is incorporated herein by reference). A transmission unit can include a near field communication (NFC) device. A transmission unit can include a Wireless Identification and Sensing Platform (WISP) device.

In an aspect, a skin-treatment delivery device can include one or more microbe profiling component 950 for profiling the microbe of a skin surface. In an aspect, the one or more microbe profiling components include a microbe capture component including a microbe capture region to capture one or more microbes from one or more regions of the skin surface of the individual and at least one sensor component including circuitry to detect one or more signals emitted or reflected from the microbe capture component, the one or more signals representative of the captured one or more microbes.

In an aspect, the one or more microbe profiling components are configured to sample and generate a profile, e.g., a two-dimensional spatial distribution, of one or more types of microbes on the skin surface of the individual. In an aspect, the skin-treatment delivery device includes one or more of the microbe profiling components described in U.S. patent application Ser. No. 14/091,762 or 14/091,832, which are incorporated herein by reference. In an aspect, the skin-treatment delivery device includes at least one of an epidermis-engaging component, e.g., a brush, bladed structure, or a pad, the epidermis-engaging component configured to dislodge one or more microbes from the skin surface of the individual. In an aspect, the skin-treatment delivery device includes a microbe capture region configured to capture one or more microbes from the skin surface of the individual. In an aspect, the microbe capture region includes at least one of a charged surface, an adhesive, a gel, and/or a biomolecule-binding polymer. In an aspect, the microbe capture region includes a plurality of specific microbe binding elements. In an aspect, the plurality of specific microbe binding elements includes a plurality of specific microbe binding antibodies, oligonucleotides, etc. In an aspect, the microbe-capture region includes a plurality of signal-generating complexes. In an aspect, each of the signal-generating complexes includes at least one signal-generating element operably coupled to at least one specific-microbe binding element, the at least one signal-generating element to emit or reflect one or more signals in response to the operably coupled at least one specific microbe binding element binding and/or interacting with one or more microbes. In an aspect, the skin-treatment delivery device includes at least one sensor configured to detect one or more signals emitted from the microbe capture region, the one or more signals indicative of the presence of one or more microbes captured from the skin surface of the individual.

In an aspect, the one or more microbe profiling components are operably coupled to the computing component of the skin-treatment delivery device. In an aspect, the computing component includes circuitry to receive information associated with the one or more regions of the skin surface of the individual from the location-capture component of the skin-treatment delivery device, to receive sensor output from the at least one sensor component, the sensor output including information associated with the detected one or more signals emitted or reflected from the microbe capture region, to correlate the information associated with the location of said one or more regions of the skin surface of the individual with the information associated with the detected one or more signals, and to generate a two-dimensional microbe profile based on the correlation between the information associated with the location of said one or more regions of the skin surface of the individual and the information associated with the detected one or more signals. In an aspect, the computing component further includes circuitry to generate a treatment map from the two-dimensional microbe profile. In an aspect, the computing component further includes circuitry to modify the treatment in response to a difference between a measured microbe profile and a stored microbe profile.

Systems for Treating a Skin Surface

Figure 10:
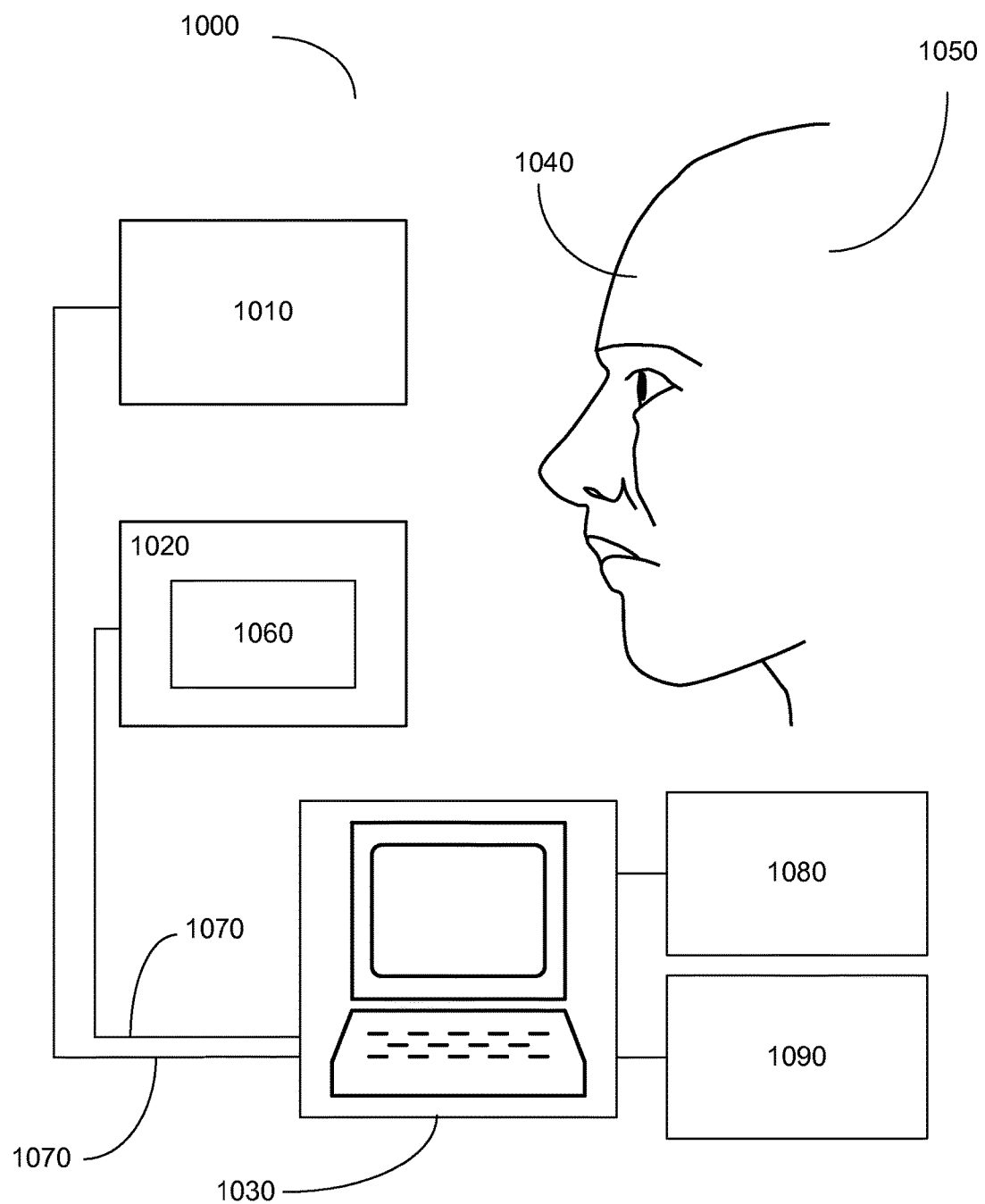
FIG. 10 shows a system for treating a skin surface.

FIG. 10 illustrates aspects of a system for treating a skin surface of an individual. System 1000 includes one or more location-capture components 1010, treatment unit 1020, and computing device 1030. One or more location-capture components 1010 of system 1000 include circuitry to determine a location on skin surface 1040 of individual 1050. In an aspect, one or more location-capture components 1010 include circuitry to measure a feature, e.g., one or more physical landmarks or fiducial markers, on skin surface 1040 of individual 1050. Treatment unit 1020 of system 1000 includes one or more treatment agent reservoirs 1060. Each of the one or more treatment agent reservoirs 1060 includes at least one controllable valve. System 1000 further includes computing device 1030. Computing device 1030 is operably coupled to one or more location-capture components 1010 and treatment unit 1020 through one or more communication links 1070. Communication links 1070 can include at least one of a wireless communication link, e.g., Bluetooth or other radio transmission link, or a wired communication link, e.g., through a USB port. Computing device 1030 further includes data storage component 1080 configured to store information associated with a profile and/or a map. Computing device 1030 further includes circuitry 1090 configured to receive information associated with the location of skin surface 1040 on individual 1050 from one or more location-capture components 1010, to correlate the location with one or more locations on the stored profile and/or map, and to actuate the controllable valve of at least one of the one or more treatment agent reservoirs 1060 of treatment unit 1020 to modulate release of one or more treatment agents at said location.

System 1000 includes location-capture component 1010. In an aspect, the location-capture component includes at least one image capture device, e.g., at least one digital camera. In an aspect, the location-capture component includes at least one fiducial reader, e.g., at least one of an optical reader, magnetic reader, audible reader, electronic reader, or RFID tag reader. In an aspect, the location-capture component includes an inertial navigation device. Non-limiting examples of location-capture components have been described above herein.

System 1000 includes treatment unit 1020 including one or more treatment agent reservoirs 1060, each of the one or more treatment agent reservoirs including at least one controllable valve. In an aspect, the treatment unit includes a hand-held unit operably coupled to the computing device through a wired connection, e.g., through a USB port. In an aspect, the treatment unit includes a hand-held unit operably coupled to the computing device through a wireless connection, e.g., through a Bluetooth connection. In an aspect, the treatment unit and the one or more location-capture components are incorporated into a walk-in enclosure sized to treat the entirety of the skin surface of the individual. For example, the treatment unit can include a walk-in treatment unit, e.g., a booth, into which the individual can enter and all or part of the skin surface treated. In an aspect, the one or more location-capture components and the treatment unit are incorporated into the same structure. For example, one or more location-capture components, e.g., one or more digital cameras, may be positioned in the head of the treatment unit. For example, one or more location-capture components may be incorporated into a walk-in treatment unit.

Treatment unit 1020 includes one or more treatment agent reservoirs 1060, each of the one or more treatment agent reservoirs configured to store and controllably release one or more treatment agents. In an aspect, the one or more treatment reservoirs include a single source of one or more treatment agents with a single controllable valve. For example, a single treatment agent reservoir can include a combination of one or more treatment agents, the combination configured to be differentially (more or less) applied to the skin surface. In an aspect, the one or more treatment agent reservoirs include a single source of treatment agents with multiple controllable valves connected through tubing to the single source of treatment agents. For example, a single treatment agent reservoir may distribute one or more treatment agents to one or more controllable valves, e.g., one or more spray units, through a series of tubing. In an aspect, treatment unit 1020 includes two or more treatment agent reservoirs 1060. In an aspect, each of the two of more treatment agent reservoirs includes one or more treatment agents. In an aspect, the computing device of the system includes circuitry to actuate the controllable valve of each of the two or more treatment agent reservoirs. In an aspect, the treatment unit includes at least one first treatment agent reservoir configured to store and controllably release at least one treatment agent of a first type and at least one second treatment agent reservoir configured to store and controllably release at least one treatment agent of a second type. In an aspect, the computing device of the system includes circuitry to actuate the controllable valve of each of the two or more treatment agent reservoirs in a treatment pattern. For example, the controllable valves may be actuated sequentially in a treatment pattern.

In an aspect, different combinations of one or more treatment agents are delivered in varying concentrations through independent control of the respective controllable valves. In an aspect, different combinations of one or more treatment agents are delivered to a given location dependent upon the distribution of microbes in that location and the treatment needs. In an aspect, the treatment unit includes one or more treatment agent reservoirs configured to store and controllably release combinations of treatment agents appropriate for different parts of the body or conditions of the body. For example, one treatment agent reservoir may hold a combination of treatment agents appropriate for the face while a second treatment agent reservoir may hold a combination of treatment agents appropriate for other parts of the body. For example, one treatment agent reservoir may hold a combination of treatment agents for a sebaceous site, a second treatment agent reservoir may hold a combination of treatment agents for moist sites, and a third treatment agent reservoir may hold a combination of treatment agents for dry sites. The combination of treatment agents released from the one or more treatment agent reservoirs of the treatment unit at any given location is dependent upon the distribution of microbes in said location and the treatment needs.

In an aspect, the treatment unit includes at least one treatment agent reservoir that is a replaceable cartridge. In an aspect, the contents of the replaceable cartridge include one or more treatment agents. In an aspect, the contents of the replaceable cartridge are personalized. In an aspect, the contents of the replaceable cartridge are personalized for a specific age, gender, ethnicity, or skin type, e.g., dry, oily, or combination skin. In an aspect, the contents of the replaceable cartridge are personalized for a specific condition, e.g., rosacea, inflammation, psoriasis, actinic keratosis, or eczema. In an aspect, the contents of the replaceable cartridge are personalized for one or more specific microbes, e.g., one or more specific antimicrobials, one or more specific probiotic agents, or one or more specific prebiotic agents.

In an aspect, each of the one or more treatment agent reservoirs of the treatment unit is configured to store and controllably release one or more treatment agents. In an aspect, at least one of the one or more treatment agent reservoirs is configured to store and controllably release one or more treatment agents. For example, in one embodiment, only a subset of the treatment agent reservoirs of the treatment unit are filled with one or more treatment agents. In an aspect, the computing device of the system includes circuitry to actuate the controllable valve of each of two or more treatment agent reservoirs. In an aspect, the computing device of the system includes circuitry to actuate the controllable valve of each of the two or more treatment agent reservoirs in a treatment pattern. In an aspect, the one or more treatment agents include one or more agents to treat a condition on the skin surface of an individual, non-limiting examples of which have been described above herein.

In an aspect, the one or more treatment agents include one or more probiotics, e.g., one or more microorganisms that positively affect the skin surface environment, non-limiting examples of which have been described above herein. In an aspect, the one or more treatment agents include one or more prebiotics, e.g., one or more agents that promote the survival and/or growth of microorganisms that positively affect the skin surface environment, non-limiting examples of which have been described above herein. In an aspect, the one or more treatment agents include one or more antimicrobial agents, inflammatory agents, chemotherapy agents, or other agents for treating or improving a condition of the skin, non-limiting examples of which have been described above herein.

In an aspect, the one or more treatment agents in the one or more treatment agent reservoirs of the treatment unit are formulated for topical administration, e.g., in liquid, gel, foam, cream, dry powder, or aerosol form. For example, the one or more treatment agents can be formulated in a liquid form with a liquefied propellant from spray application. Other non-limiting examples of formulation for topical administration have been described above herein.

System 1000 includes computing device 1030. Computing device 1030 includes data storage component 1080 and circuitry 1090. Computing device 1030 can take various forms or be part of an object, and can include, but is not limited to, a computer, a laptop computer, a personal electronic device, a dedicated computing device, a limited resource computing device, a wireless communication device, a mobile wireless communication device, a handheld electronic writing device, a tablet, a digital camera, a scanner, a cell phone, a PDA, an electronic tablet device, a printer, or any other like device that takes information as an input and gives it back to the end-users. In an aspect, computing device 1030 can be part of an object, e.g., treatment unit 1020 or a kiosk. Computing device 1030 can include a digital single processor, ASIC, microprocessor, or other type of processor operating on a system such as a personal computer, server, a router, of other device capable of processing data including network interconnection device. Computing device 1030 can include a user interface, e.g., a keyboard or touchscreen and display. Computing device 1030 shares many aspects of a computing component, e.g., computing component 290 shown in FIG. 2, non-limiting aspects of which have been described above herein. In an aspect, computing device 1030 includes circuitry to receive location information, correlate the location information with a microbe profile and/or a treatment map, select one or more treatment agents based on the correlation, and actuate the controllable valve of at least one of the one or more treatment agent reservoirs. In an aspect, computing device 1030 further includes circuitry to record delivery data, e.g., one or more treatment agents delivered, location, dose, time, and date. In an aspect, computing device 1030 includes circuitry to convert the recorded delivery data into a treatment map. In an aspect, computing device 1030 includes circuitry to report the delivery data to a user, e.g., the individual, a medical practitioner or other practitioner, a pharmacy, or supplier of the one or more treatment agents.

In an aspect, computing device 1030, treatment unit 1020, and the location-capture component 1010 are incorporated into a kiosk, e.g., a medical kiosk in a medical facility or pharmacy, or a commercial kiosk at a cosmetic counter. In an aspect, the treatment of the individual's skin surface at a kiosk includes at least one of treatment with one or more treatment agents based on a microbe profile and/or treatment map, a printout of the microbe profile and/or treatment map, a printout of the recorded delivery data, recommendations for follow-up treatment, recommendations for products, e.g., one or more treatment agents, and product coupons. The kiosk experience can further include transmitting information associated with the microbe profile, treatment map, recorded delivery data, recommended follow-up treatment, recommendations for products, and product coupons to the individual's personal computing device, e.g., a smart phone or tablet device.

Figure 11:
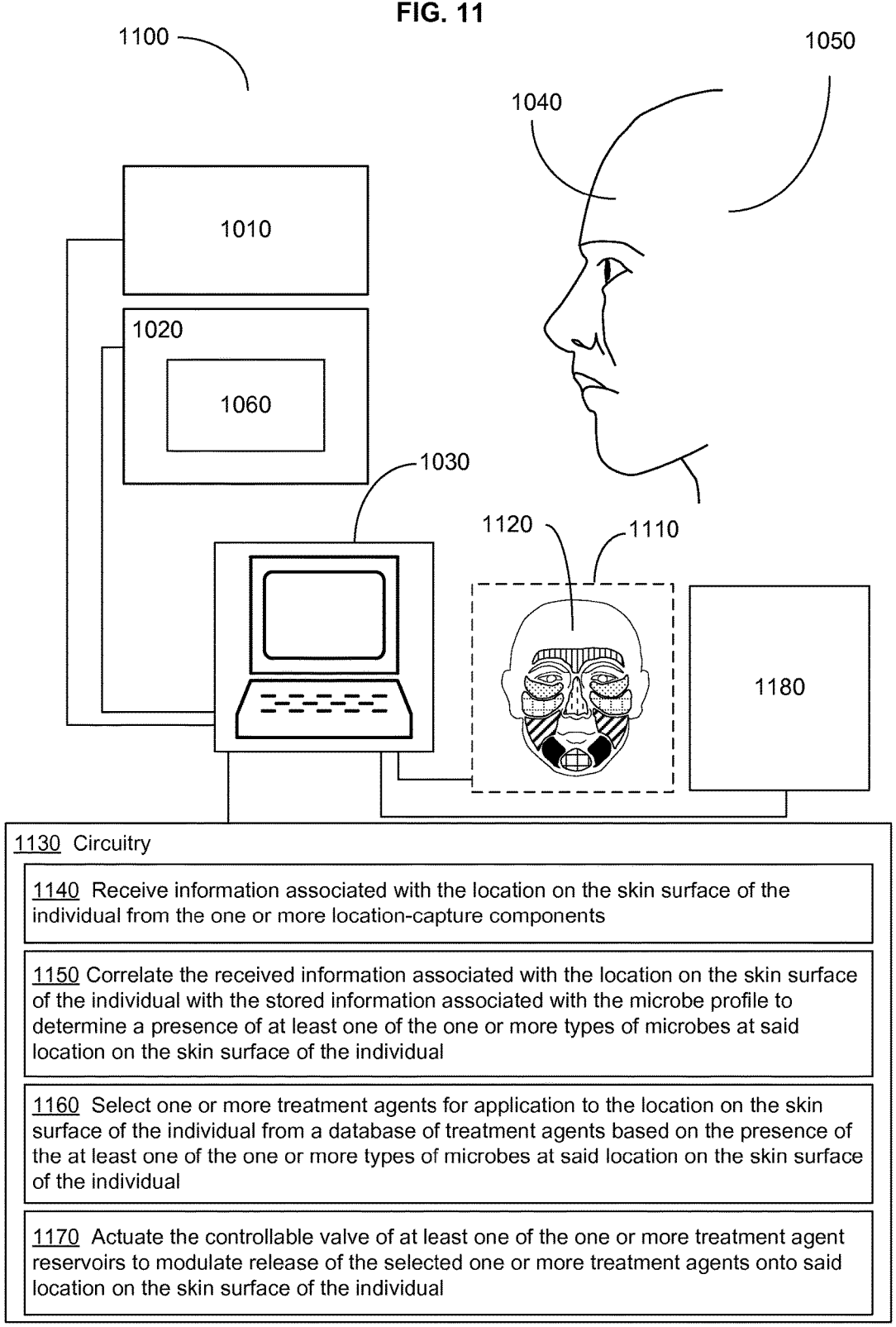
FIG. 11 shows a system including a microbe profile for treating a skin surface.

FIG. 11 shows aspects of a system for treating a skin surface including a microbe profile. System 1100 includes one or more location-capture components 1010, treatment unit 1020, and computing device 1030. System 1100 includes one or more location-capture components 1010 including circuitry to determine a location on skin surface 1040 of individual 1050. System 1100 includes treatment unit 1020 including one or more treatment agent reservoirs 1060, each of the one or more treatment agent reservoirs 1060 including a controllable valve. System 1100 further includes computing device 1030 operably coupled to one or more location-capture components 1010 and the controllable valve of each of one or more treatment agent reservoirs 1060. Computing device 1030 of system 1100 includes data storage component 1110, microbe profile 1120, and database of treatment agents 1180.

Data storage component 1110 is configured to store information associated with a microbe profile 1120, microbe profile 1120 including a two-dimensional spatial distribution of one or more types of microbes on the skin surface of the individual. In an aspect, the data storage component of the computing device includes a removable data storage component, e.g., a memory card, memory stick, flash drive, or a compact disk. In an aspect, the information associated with the microbe profile includes a web address to remotely access the microbe profile. In an aspect, the information associated with the microbe profile is updatable. In an aspect, the entirety of the microbe profile is updateable. For example, a more recently generated microbe profile might replace a previously generated microbe profile. In an aspect, the update includes adding information, e.g., the identity of one or more types of microbes. In an aspect, the update includes subtracting information, e.g., subtracting information related to microbes no longer of interest. In an aspect, the data storage component includes circuitry to receive the microbe profile from a remote source, e.g., a remote computing device, a microbe profiling device, or through the Internet.

In an aspect, microbe profile 1120 includes a feature map of the skin surface of the individual. In an aspect, the feature map includes one or more images of the skin surface of the individual. In an aspect, the feature map includes one or more fiducial markers on the skin surface of the individual. In an aspect, the feature map includes one or more coordinates.

Computing device 1030 further includes circuitry 1130. Circuitry 1130 of computing device 1030 includes circuitry 1140 to receive information associated with the location on skin surface 1040 of individual 1050 from one or more location-capture components 1010. Circuitry 1130 of computing device 1030 includes circuitry 1150 to correlate the received information associated with the location on skin surface 1040 of individual 1050 with the stored information associated with microbe profile 1120 to determine a presence of at least one of the one or more types of microbes at said location on skin surface 1040 of individual 1050. Circuitry 1130 of computing device 1030 further includes circuitry 1160 to select one or more treatment agents for application to the location on skin surface 1040 of individual 1050 from a database of treatment agents 1180 based on the presence of the at least one of the one or more types of microbes at said location on skin surface 1040 of individual 1050. Circuitry 1130 further includes circuitry 1170 to actuate the controllable valve of at least one of one or more treatment agent reservoirs 1060 to modulate release of the selected one or more treatment agents onto said location on skin surface 1040 of individual 1050.

Computing device 1030 of system 1100 includes circuitry to execute one or more instructions, the one or more instructions include one or more instructions for receiving information associate with the location on the skin surface of the individual from the location-capture component, one or more instructions for correlating the received information with the location on the skin surface of the individual with the stored information associated with the microbe profile to determine a presence of at least one of the one or more types of microbes at said location on the skin surface of the individual, one or more instructions for selecting one or more treatment agents for application to the location on the skin surface of the individual from a database of treatment agents based on the presence of the at least one of the one or more types of microbes at said location on the skin surface of the individual, and one or more instructions for actuating the controllable valve of at least one of the one or more treatment agent reservoirs to modulate release of the selected one or more treatment agents onto said location on the skin surface of the individual.

Computing device 1030 of system 1100 includes circuitry 1140 to receive information associated with the location on the skin surface of the individual from location-capture component 1010. In an aspect, the computing device includes circuitry to receive the information associated with the location on the skin surface of the individual from at least one of an image capture device, a fiducial reader, or an inertial navigation device. In an aspect, the computing device includes circuitry to receive information associated with a measured feature of the location on the skin surface of the individual from the location-capture component. In an aspect, the computing device includes circuitry to receive at least one of one or more images, one or more fiducial markers, or one or more coordinates representative of the location on the skin surface of the individual.

Computing device 1030 of system 1100 includes circuitry 1150 to correlate the received information associated with the location on the skin surface of the individual with the stored information associated with the microbe profile to determine a presence of at least one of the one or more types of microbes at said location on the skin surface of the individual. In an aspect, the computing device includes circuitry to align the location on the skin surface of the individual with one or more locations on a feature map of the skin surface of the individual embedded in the microbe profile. In an aspect, the computing device includes circuitry to align one or more images of the location on the skin surface of the individual with images of one or more locations on the feature map of the skin surface of the individual embedded in the microbe profile. In an aspect, the computing device includes circuitry to align one or more fiducial markers of the location on the skin surface of the individual with the fiducial marker of one or more locations on the feature map of the skin surface of the individual embedded in the microbe profile. In an aspect, the computing device includes circuitry to align one or more coordinates of the location on the skin surface of the individual with coordinates of one or more locations on the feature map of the skin surface of the individual embedded in the microbe profile.

Computing device 1030 of system 1100 includes circuitry 1160 to select one or more treatment agents for application to the location on the skin surface of the individual from database of treatment agents 1180 based on the presence of the at least one of the one or more types of microbes at said location on the skin surface of the individual. In an aspect, the database of treatment agents is stored in the data storage component. In an aspect, the database of treatment agents reflects the one or more treatment agents available for use in the system. In an aspect, the database of treatment agents reflects the one or more treatment agents currently present in the one or more treatment agent reservoirs. In an aspect, the database of treatment agents is updatable. For example, the database of treatment agents can be updated to add or subtract one or more treatment agents. For example, the database of treatment agents can be updated to reflect the one or more treatment agents incorporated into the one or more treatment agent reservoirs of the system. For example, each removable treatment agent reservoir may include a code, e.g., a bar code, including information to update the database of treatment agents. For example, updates to the database of treatment agents may reflect changes in the treatment map and/or the microbe profile of the individual. In an aspect, the database of treatment agents includes a look-up table including one or more treatment agents matched with one or more types of microbes. In an aspect, the database of treatment agents includes information associated with one or more treatment agents matched with information associated with one or more types of microbes.

Computing device 1030 of system 1100 includes circuitry 1170 to actuate the controllable valve of at least one of the one or more treatment agent reservoirs to modulate release of the selected one or more treatment agents onto said location on the skin surface of the individual. In an aspect, the computing device includes circuitry to actuate the controllable valve of each of two or more treatment agent reservoirs. For example, the computing device can include circuitry to actuate the controllable valve of each of two or more treatment agent reservoirs simultaneously. For example, the computing device can include circuitry to actuate the controllable valve of each of two or more treatment agent reservoirs sequentially. In an aspect, the computing device includes circuitry to actuate the controllable valve of each of the two or more treatment agent reservoirs in a treatment pattern.

Figure 12:
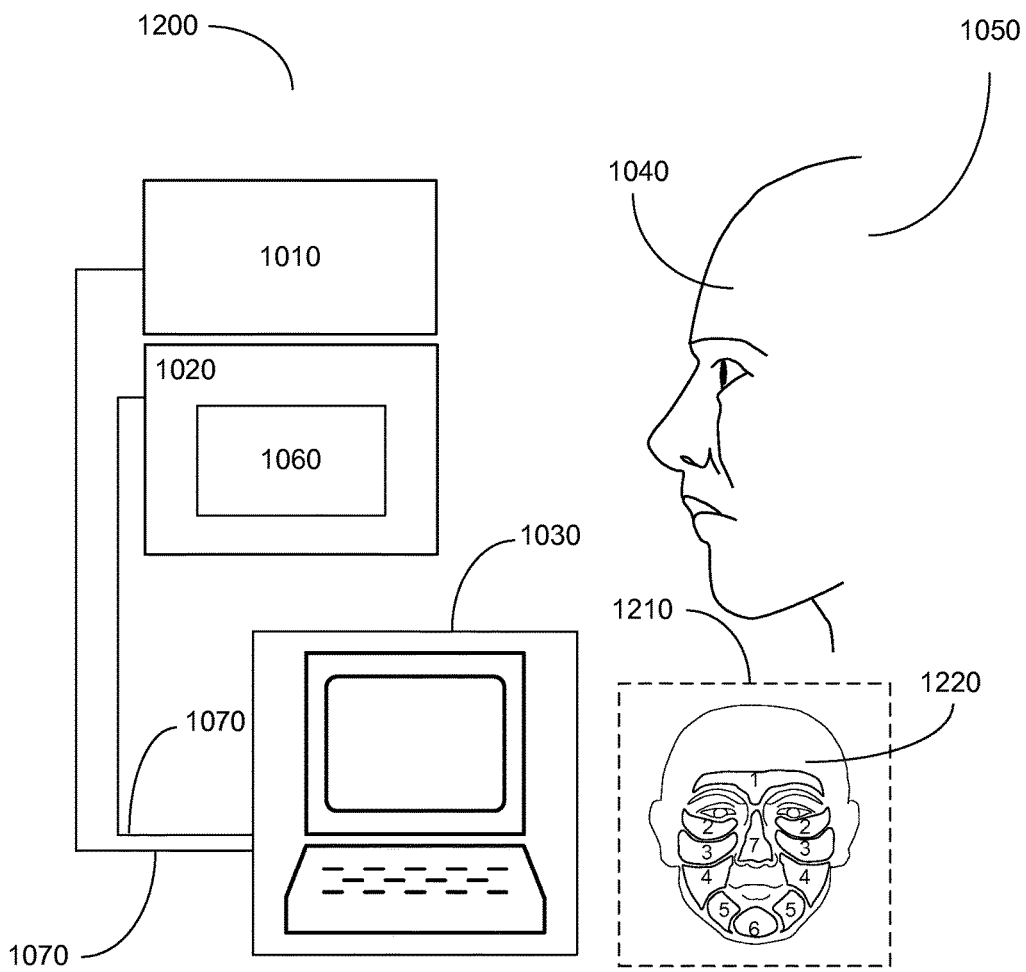
FIG. 12 shows a system including a treatment map for treating a skin surface.

FIG. 12 shows a system for treating a skin surface including a treatment map. System 1200 includes one or more location-capture components 1010, treatment unit 1020, and computing device 1030. System 1200 includes one or more location-capture components 1010 including circuitry to determine a location on skin surface 1040 of individual 1050. System 1200 includes treatment unit 1020 including one or more treatment agent reservoirs 1060, each of one or more treatment agent reservoirs 1060 including a controllable valve. System 1200 further includes computing device 1030 operably coupled to one or more location-capture components 1010 and treatment unit 1020 through one or more communication links 1070.

System 1200 further includes data storage components 1210 configured to store information associated with treatment map 1220, treatment map 1220 including a two-dimensional spatial distribution of one or more treatment agents for application to one or more locations on skin surface 1040 of individual 1050. In an aspect, the data storage component of the computing device includes a removable data storage component, e.g., a memory card, a memory stick, a flash drive, or a compact disk. In an aspect, the stored information associated with the treatment map includes a web address to remotely access the treatment map. In an aspect, the information associated with the treatment map is updatable. In an aspect, the entirety of the treatment map is updatable. In an aspect, the update includes adding information, e.g., adding one or more additional treatment agents. In an aspect, the update includes subtracting information, e.g., subtracting one or more treatment agents from the treatment map. In an aspect, the update includes updating the treatment map to reflect the one or more treatment agents available in the one or more treatment agent reservoirs of the treatment unit. In an aspect, the update to the treatment map reflects changes to an individual's microbe profile or other skin condition. In an aspect, the data storage component includes circuitry to receive the treatment map from a remote source, e.g., a remote computing device, a microbe profiling device, or through the Internet.

In an aspect, treatment map 1220 corresponds to a microbe profile, the microbe profile including a two-dimensional spatial distribution of one or more types of microbes on the skin surface of the individual. In an aspect, the two-dimensional spatial distribution of the one or more treatment agents for application to the skin surface of the individual overlaps a two-dimensional spatial distribution of one or more types of microbes on the skin surface of the individual. In an aspect, treatment map 1220 includes a feature map of the skin surface of the individual. In an aspect, the feature map of the skin surface of the individual includes one or more images, one or more fiducial markers, and/or one or more coordinates of the skin surface of the individual. In an aspect, the feature map of the skin surface of the individual is embedding in the treatment map.

Computing device 1030 of system 1200 further includes circuitry 1230. Circuitry 1230 of system 1200 includes circuitry 1240 to receive information associated with the location on skin surface 1040 of the individual 1050 from the one or more location-capture components 1010. Circuitry 1230 of system 1200 includes circuitry 1250 to correlate the received information associated with the location on skin surface 1040 of individual 1050 with the stored information associated with treatment map 1220 to select the one or more treatment agents for application at said location on skin surface 1040 of individual 1050. Circuitry 1230 of system 1200 further includes circuitry 1260 to actuate the controllable valve of at least one of one or more treatment agent reservoirs 1060 to modulate release of the selected one or more treatment agents for application at said location on skin surface 1040 of individual 1050.

Computing device 1030 of system 1200 includes circuitry to execute one or more instructions, the one or more instructions include one or more instructions for receiving information associate with the location on the skin surface of the individual from the location-capture component, one or more instructions for correlating the received information with the location on the skin surface of the individual with the stored information associated with the treatment map to select the one or more treatment agents for application at said location, and one or more instructions for activating the controllable valve of at least one of the one or more treatment agent reservoirs to modulate release of the selected one or more treatment agents for application at said location on the skin surface of the individual.

Computing device 1030 of system 1200 includes circuitry to receive information associated with the location on the skin surface of the individual from the one or more location-capture components. In an aspect, computing device 1030 of system 1200 includes circuitry to receive the information associated with the location on the skin surface of the individual from at least one of an image capture device, a fiducial reader, or an inertial navigation device. In an aspect, the information associated with the location on the skin surface of the individual includes at least one of one or more images, one or more fiducial markers, or one or more coordinates representative of the location on the skin surface of the individual. In an aspect, computing device 1030 of system 1200 includes circuitry to receive at least one of one or more images, one or more fiducial markers, or one or more coordinates representative of the location on the skin surface of the individual.

Computing device 1030 of system 1200 includes circuitry to correlate the received information associated with the location on the skin surface of the individual with the stored information associated with the treatment map to select the one or more treatment agents for application at said location on the skin surface of the individual. In an aspect, computing device 1030 of system 1200 includes circuitry to align the location on the skin surface of the individual with one or more locations on a feature map of the skin surface of the individual embedded in the treatment map. In an aspect, computing device 1030 of system 1200 includes circuitry to align one or more images of the location on the skin surface of the individual with images of one or more locations on the feature map of the skin surface of the individual embedded in the treatment map. In an aspect, computing device 1030 of system 1200 includes circuitry to align one or more fiducial markers of the location on the skin surface of the individual with fiducial markers of one or more locations on the feature map of the skin surface of the individual embedded in the treatment map. In an aspect, computing device 1030 of system 1200 includes circuitry to align one or more coordinates of the location on the skin surface of the individual with coordinates of one or more locations on the feature map of the skin surface of the individual embedded in the treatment map.

Computing device 1030 of system 1200 includes circuitry to actuate the controllable valve of at least one of the one or more treatment agent reservoirs to modulate release of the selected one or more treatment agents for application at said location on the skin surface of the individual. In an aspect, the computing device includes circuitry to actuate the controllable valve of each of two or more treatment agent reservoirs. In an aspect, the computing device includes circuitry to actuate the controllable valve of each of the two or more treatment agent reservoirs in a pattern. For example, the computing device can include circuitry to actuate the controllable valve of each of two or more treatment agent reservoirs simultaneously. For example, the computing device can include circuitry to actuate the controllable valve of each of two or more treatment agent reservoirs sequentially.

Figure 13A:
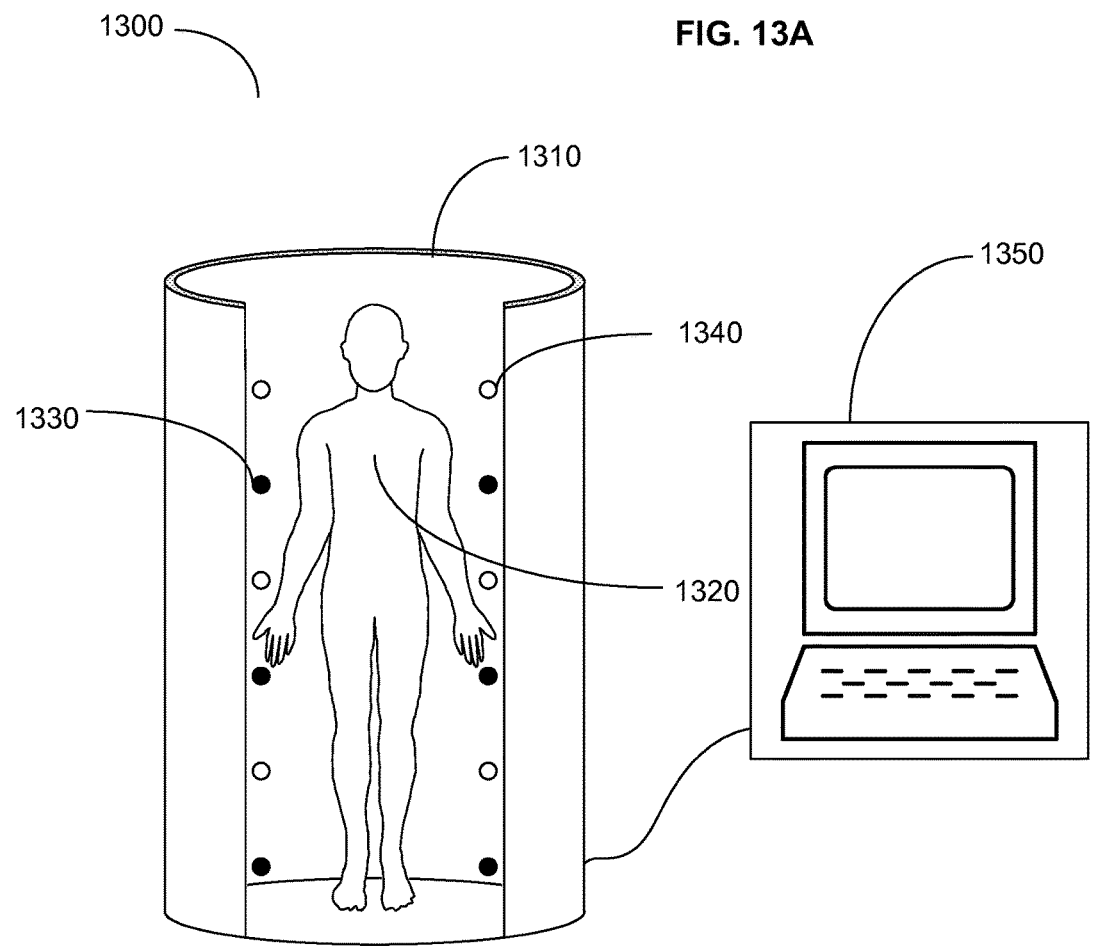
FIG. 13A shows a side-view of a system for treating a skin surface including a walk-in treatment unit.
Figure 13B:
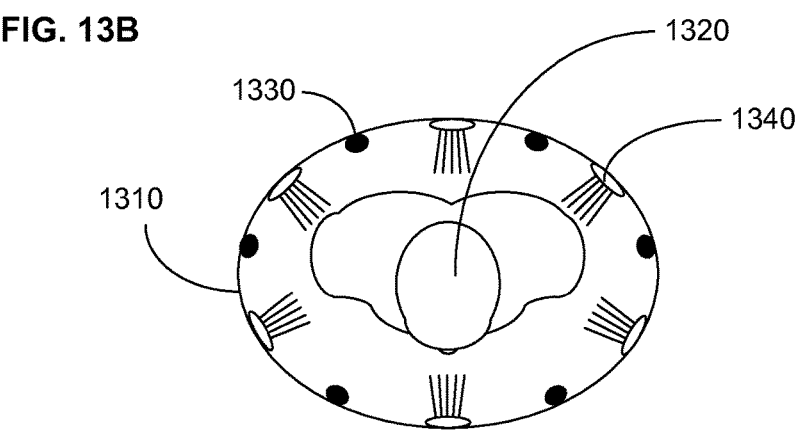
FIG. 13B shows a top-view of a system for treating a skin surface including a walk-in treatment unit.

In an aspect, a system for delivering a skin treatment includes a treatment unit and one or more location capture components incorporated into a walk-in enclosure sized to treat the entirety of the skin surface of the individual, the walk-in enclosure including one or more treatment agent reservoirs. FIGS. 13A and 13B show aspects of a system for treating a skin surface of an individual including a walk-in treatment unit. System 1300 includes walk-in enclosure 1310. In an aspect, walk-in enclosure 1310 is a treatment unit including one or more treatment agent reservoirs. In an aspect, walk-in enclosure 1310 includes a height, e.g., 7 feet, and a cross-sectional diameter, e.g., 3 feet, sufficient to accommodate an adult individual 1320. In an aspect, walk-in enclosure 1310 includes a door, e.g., a sliding door, which allows individual 1320 to be completely surrounded by the walls of the walk-in enclosure and the associated components. Walk-in enclosure 1310 includes multiple location-capture components 1330 within the interior of walk-in enclosure 1310. One or more location-capture components 1330 include circuitry to determine a location on a skin surface of the individual. The one or more location-capture components can include at least one of one or more image capture devices, one or more fiducial readers, or one or more inertial navigation devices.

In an aspect, walk-in enclosure 1310 includes one or more treatment agent reservoirs. In an aspect, the one or more treatment agent reservoirs are distributed in a pattern within walk-in enclosure 1310 to treat the entirety of the skin surface of the individual. In an aspect, at least one of the one or more treatment agent reservoirs of walk-in enclosure 1310 includes an amiable nozzle in fluid communication with the controllable valve of the at least one of the one or more treatment agent reservoirs. Walk-in enclosure 1310 further includes multiple outlets 1340, each of the outlets 1340 in fluid communication with one or more treatment agent reservoirs. In an aspect, each of outlets 1340 includes a controllable valve. In an aspect, the outlets 1340 include a spray nozzle for delivering an aerosolized or spray formulation of the one or more treatment agents. See, e.g., U.S. Pat. No. 6,199,557 to Laughlin titled "Method of and Apparatus for Automatically Coating the Human Body," which is incorporated herein by reference.

System 1300 further includes computing device 1350. In an aspect, computing device 1350 includes a data storage component configured to store information associated with a microbe profile, the microbe profile including a two-dimensional spatial distribution of one or more types of microbes on the skin surface of individual 1320. In an aspect, computing device 1350 further includes circuitry to receive information associated with the location on the skin surface of individual 1320 from the one or more location-capture components 1330; circuitry to correlate the received information associated with the location on the skin surface of the individual with the stored information associated with the microbe profile to determine a presence of at least one of the one or more types of microbes at said location on the skin surface of individual 1320; circuitry to select one or more treatment agents for application to the location on the skin surface of individual 1320 from a database of treatment agents based on the presence of the at least one of the one or more types of microbes at said location on the skin surface of individual 1320; and circuitry to actuate the controllable valve of at least one of the outlets 1340 in fluid communication with one or more treatment agent reservoirs associated with treatment unit 1310 to modulate release of the selected one or more treatment agents onto said location on the skin surface of individual 1320.

In an aspect, computing device 1350 includes a data storage component configured to store information associated with a treatment map, the treatment map including a two-dimensional spatial distribution of one or more treatment agents for application to one or more locations on the skin surface of individual 1320. In an aspect, computing device 1350 further includes circuitry to receive information associated with the location on the skin surface of individual 1320 from the one or more location-capture components 1330; circuitry to correlate the received information associated with the skin surface of individual 1320 with the stored information associated with the treatment map to select the one or more treatment agents for application at said location on the skin surface of the individual; and circuitry to actuate the controllable valve of at least one of the outlets 1340 in fluid communication with one or more treatment agent reservoirs associated with treatment unit 1310 to modulate release of the selected one or more treatment agents onto said location on the skin surface of individual 1320.

FIG. 13B shows a top-view of walk-in enclosure 1310 in which individual 1320 is completely enclosed in the walk-in treatment unit. Walk-in enclosure 1310 includes location-capture components 1330 and outlets 1340 connected to one or more treatment agent reservoirs and configured to controllably deliver one or more treatment agents to the skin surface of individual 1320. In an aspect, computing device 1350 includes circuitry to actuate the controllable valve of each of two or more treatment agent reservoirs. In an aspect, computing device 1350 includes circuitry to actuate the controllable valve of each of two or more treatment agent reservoirs in a treatment pattern. In an aspect, the treatment pattern is a spatial treatment pattern, a temporal treatment pattern, or a combination thereof.

Figure 14:
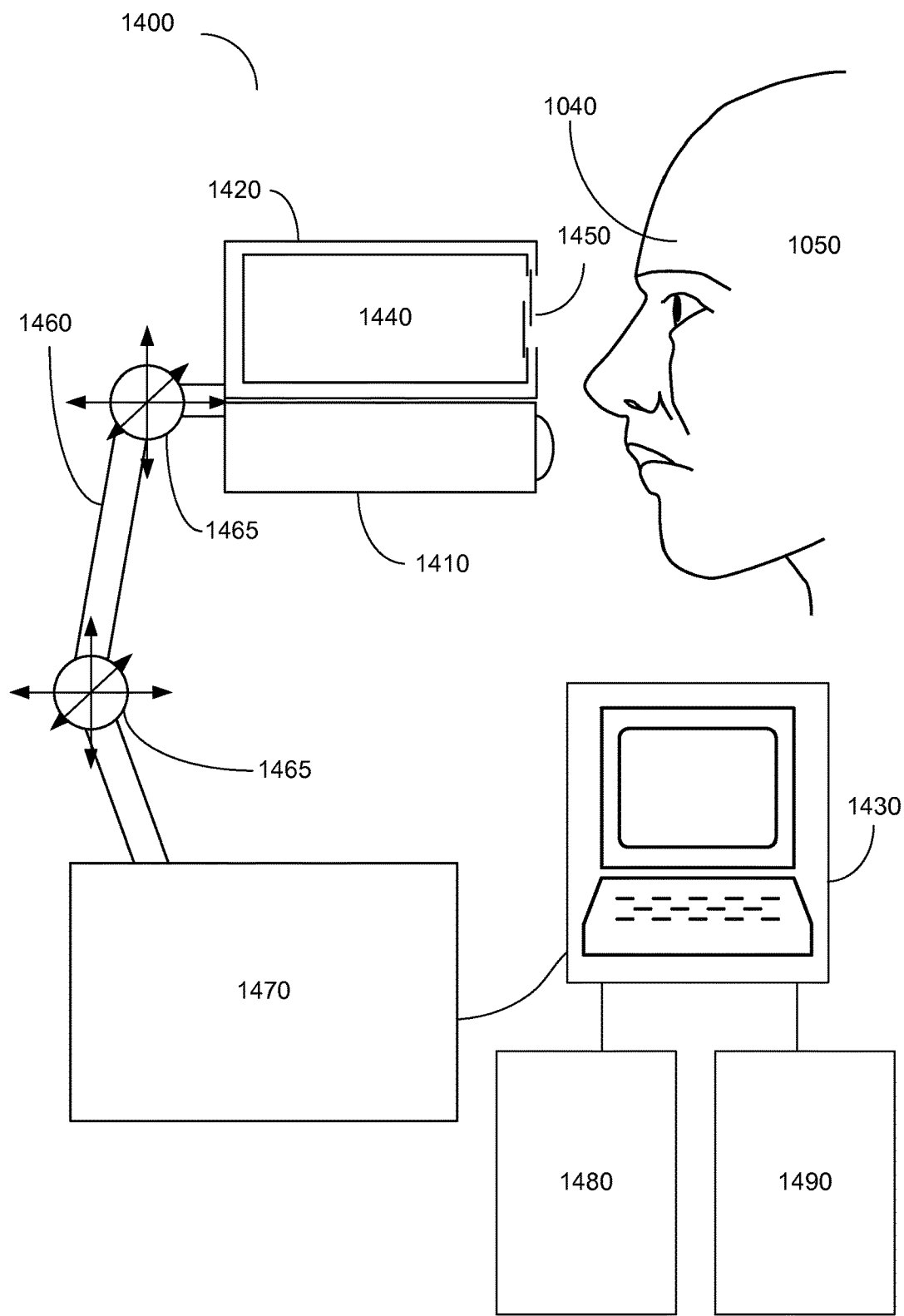
FIG. 14 shows a system for treating a skin system including a treatment unit attached to a motivatable portion.

In an aspect, a system for delivering a skin treatment includes a motivatable portion attached to a treatment unit, the motivatable portion operably coupled to a computing device and including circuitry to move the treatment unit over the skin surface of an individual to deliver one or more treatment agents according at least one of a microbe profile or a treatment map. FIG. 14 shows aspects of a system for treating a skin surface of an individual including a motivatable portion. System 1400 includes one or more location-capture components 1410, treatment unit 1420, and computing device 1430. One or more location-capture components 1410 include circuitry to determine a location on skin surface 1040 of individual 1050. Treatment unit 1420 includes one or more treatment agent reservoirs 1440, each of the one or more treatment agent reservoirs 1440 including a controllable valve 1450. In an aspect, treatment unit 1420 is attached to motivatable component 1460. In an aspect, at least one of one or more location-capture components 1410 is attached to motivatable component 1460. In an aspect, one or more location-capture components 1410 and treatment unit 1420 are bundled into a single unit attached to motivatable portion 1460. In an aspect, motivatable portion 1460 includes one or more pivot points 1465 with potential movement of at least 3 degrees of freedom. In an aspect, motivatable portion 1460 includes circuitry to autonomously move attached treatment unite 1420 over skin surface 1040 of individual 1050. In an aspect, motivatable portion 1460 includes circuitry to autonomously move attached treatment unit 1420 in a pattern over an area of skin surface 1040 of individual 1050. In an aspect, motivatable portion 1460 is attached to controller 1470. Controller 1470 includes circuitry to control the movement of motivatable portion 1460 in response to commands from computing device 1430. For example, computing device 1430 may send controller 1470 a movement pattern to guide movement of motivatable portion 1460 and attached treatment unit 1420 and one or more location-capture components 1410. For example, computing device 1430 may send controller 1470 a movement pattern according to a microbe profile or a treatment map.

System 1400 further includes computing device 1430. Computing device 1430 includes data storage component 1480. In an aspect, data storage component 1480 is configured to store information associated with a microbe profile, the microbe profile including a two-dimensional spatial distribution of one or more types of microbe on skin surface 1040 of individual 1050. In an aspect, data storage component 1480 is configured to store information associated with a treatment map, the treatment map including a two-dimensional spatial distribution of one or more treatment agents for application to one or more locations on the skin surface of the individual.

Computing device 1430 further includes circuitry 1490. In an aspect, circuitry 1490 includes circuitry to receive information associated with the location on the skin surface of the individual from the one or more location-capture components, correlate the received information associated with the location on the skin surface of the individual with the stored information associated with the microbe profile to determine a presence of at least one of the one or more types of microbes at said location on the skin surface of the individual, select one or more treatment agents for application to the location on the skin surface of the individual from a database of treatment agents based on the presence of the at least one of the one or more types of microbes at said location on the skin surface of the individual, and actuate the controllable valve of at least one of one or more treatment agent reservoirs to modulate release of the selected one or more treatment agents onto said location on the skin surface of the individual. In an aspect, computing device 1430 instructs controller 1470 to move motivatable portion 1460 in a pattern consistent with the microbe profile. For example, the computing device can instruct the controller to move the motivatable portion in a pattern consistent with the boundaries of the microbe profile, e.g., back and forth, and/or up and down over the skin surface of an individual's face or other body part, to deliver the selected one or more treatment agents to the appropriate locations on the skin surface.

In an aspect, circuitry 1490 includes circuitry to receive information associated with the location on skin surface of the individual from the one or more location-capture components, correlate the received information associated with the location on the skin surface of the individual with the stored information associated with the treatment map to select the one or more treatment agents for application at said location on the skin surface of the individual, and actuate the controllable valve of at least one of the one or more treatment agent reservoirs to modulate release of the selected one or more treatment agents for application at said location on the skin surface of the individual. In an aspect, computing device 1430 instructs controller 1470 to autonomously move motivatable portion 1460 in a pattern consistent with the treatment map. For example, the computing device can instruct the controller to move the motivatable portion in a pattern consistent with the boundaries of the treatment map, e.g., back and forth, and/or up and down over the skin surface of an individual's face or other body part.

In an aspect, a system for delivering a skin treatment can include a stationary portion including a treatment unit and at least one of the one or more location-capture components, the stationary portion configured to deliver the selected one or more treatment agents to the skin surface of a moving body part. For example, the system can include a desktop stationary portion over which a body part, e.g., an individual's hand, can be moved, imaged with an image capture device, and treated with one or more treatment agents based on the individual's personalized microbe profile or treatment map.

Methods of Delivering a Treatment to a Skin Surface

FIG. 15 is a flowchart of a method for delivering a treatment to a skin surface based on a microbe profile. The method includes in block 1500 receiving information associated with a location on the skin surface of an individual from a location-capture component of a skin-treatment delivery device, the skin-treatment delivery device including the location-capture component; one or more treatment agent reservoirs, each of the one or more treatment agent reservoirs including at least one port with a controllable valve; at least one conduit in fluid communication with the at least one port with the controllable valve and an opening defined by a surface of the skin-treatment delivery device; a data storage component configured to store information associated with a microbe profile, the microbe profile including a two-dimensional spatial distribution of one or more types of microbes at each of one or more locations on the skin surface of the individual; and a computing component including a processor and circuitry, the computing component operably coupled to the location-capture component, the controllable valve of each of the one or more treatment agent reservoirs, and the data storage component. The method further includes in block 1510, correlating the received information associated with the location on the skin surface of the individual with the information associated with the microbe profile to determine a presence of at least one of the one or more types of microbes at said location on the skin surface of the individual. The method includes in block 1520, selecting one or more treatment agents for application to the location on the skin surface of the individual from a database of treatment agents based on the presence of the at least one of the one or more types of microbes at said location on the skin surface of the individual. The method includes in block 1530, actuating the controllable valve of at least one of the one or more treatment agent reservoirs to modulate release of the selected one or more treatment agents onto said location on the skin surface of the individual. In an aspect, the method includes at least partially opening or partially closing the controllable valve of at least one of the one or more treatment agent reservoirs to modulate release of the selected one or more treatment agents onto said location on the skin surface of the individual.

The method of delivering a treatment to a skin surface includes receiving information associated with a location on the skin surface of an individual from a location-capture component. In an aspect, the method includes receiving the information associated with the location on the skin surface of the individual from an image capture device, e.g., a digital camera or other imaging device, non-limiting examples of which have been described above herein. In an aspect, the method includes receiving the information associated with the location on the skin surface of the individual from a fiducial reader, e.g., an image capture device, an electronic reader, a magnetic reader, or an RFID tag reader. In an aspect, the method includes receiving the information associated with the location on the skin surface of the individual from an inertial navigation device. In an aspect, the information associated with the location on the skin surface of the individual includes one or more features of the skin surface, e.g., one or more images, one or more fiducial markers, one or more physical landmarks, or one or more coordinates.

FIG. 16 shows further aspects of a method for delivering a treatment to a skin surface. In an aspect, the method includes in block 1600 receiving an update to the information associated with the location on the skin surface of the individual from the location-capture component in response to moving the skin-treatment delivery device to a new location on the skin surface of the individual. In an aspect, the method includes receiving an update to the information associated with the location on the skin surface of the individual from at least one of an image-capture device, a fiducial reader, or an inertial navigation device in response to moving the skin-treatment delivery device to a new location on the skin surface of the individual. For example, the method can include receiving updated images of the skin surface from a digital camera as the skin-treatment delivery device is moved from one location to another on the skin surface of the individual. For example, the method can include receiving updated fiducial reading, e.g., from a pattern of magnetic or RFID tags on the skin surface, from a fiducial reader as the skin-treatment delivery device is moved from one location to another on the skin surface of the individual. In an aspect, the method further includes reading one or more fiducials on the skin surface of the individual with the location-capture component to determine a location. For example, the method can include reading one or more fiducials that are physical landmarks, e.g., freckles, on the skin surface of the individual. For example, the method can include reading one or more fiducials that are fiducial markers, e.g., colored or magnetic tags, placed on the skin surface of the individual as reference point. In an aspect, the method includes receiving an update to the location on the skin surface of the individual from the location-capture component in response to moving a body part including the skin surface relative to a stationary skin-treatment delivery device.

In an aspect, the method includes receiving the information associated with the microbe profile from a remote source, as shown in block 1610 of FIG. 16. In an aspect, the method includes receiving the information associated with the microbe profile from a microbe profiling device. For example, the method can include receiving the information associated with the microbe profile from a hand-held microbe profiling device such as described in U.S. patent application Ser. Nos. 14/091,762 and 14/091,805, which are incorporated herein by reference. In an aspect, the method includes receiving the information associated with the microbe profile from a second computing device. For example, the method can include receiving the information associated with the microbe profile from a second computing device that is part of a microbe profiling system such as described in U.S. patent application Ser. Nos. 14/091,793 and 14/091,856, which are incorporated herein by reference. In an aspect, the method includes receiving the information associated with the microbe profile through the Internet. In an aspect, the method includes receiving the information associated with the microbe profile through a wired communication link, e.g., a wire communication link between a microbe profiling device or a second computing device and the skin-treatment delivery device. In an aspect, the method includes receiving the information associated with the microbe profile through a wireless communication link, e.g., a Bluetooth connection with a transmission unit of a microbe profiling device or a wireless Internet connection.

In an aspect, the method includes receiving an update to the information associated with the microbe profile, as shown in block 1620 of FIG. 16. In an aspect, the method includes receiving the update to the information associated with the microbe profile in response to profiling one or more types of microbe on the skin surface of the individual. For example, the method can include receiving the update to the microbe profile in response to re-profiling the microbe of the skin surface of the individual.

In an aspect, the method includes correlating the received information associated with the location on the skin surface of the individual with the stored information associated with the microbe profile by aligning the received information associated with the location on the skin surface of the individual with one or more reference locations embedded in the microbe profile, as shown in block 1630 of FIG. 16. In an aspect, the one or more reference locations embedded in the microbe profile includes a feature map including one or more images, one or more fiducial markers, and/or one or more coordinates representative of one or more locations on the skin surface of the individual. In an aspect, the method includes aligning one or more images of the location on the skin surface of the individual with images of the one or more reference locations embedded in the microbe profile. In an aspect, the method includes aligning one or more fiducial markers of the location on the skin surface of the individual with fiducial markers of one or more reference locations embedded in the microbe profile. In an aspect, the method includes aligning one or more coordinates of the location on the skin surface of the individual with coordinates of the one or more reference locations embedded in the microbe profile. In an aspect, the method includes using an alignment algorithm to align the received information associated with the location on the skin surface of the individual with one or more reference locations embedded in the microbe profile. Non-limiting examples of alignment algorithms have been described above herein.

In an aspect, the method further includes alerting a user if the correlation between the received information associated with the location on the skin surface of the individual and the stored information associated with the microbe profile indicates that the location on the skin surface of the individual is outside a boundary of the microbe profile, as shown in block 1640 of FIG. 16. For example, the method can including alerting the user, e.g., with a visual, audio, or haptic signal, if the location on the skin surface cannot be found in the reference locations embedded in the microbe profile.

In an aspect, the method includes selecting the one or more treatment agents for application to the location on the skin surface of the individual from a look-up table including treatment agents matched with types of microbes, as shown in block 1650 of FIG. 16. In an aspect, the method includes selecting one or more treatment agents available in the one or more treatment agent reservoirs. In an aspect, the method includes alerting a user if the selected one or more treatment agents are not available in the one or more treatment agent reservoirs.

FIG. 17 shows further aspects of a method for delivering a treatment to a skin surface. In an aspect, the method includes emitting one or more signals with a signal-generating component of the skin-treatment delivery device to notify a user of a condition, as shown in block 1700. In an aspect, the condition includes a condition of the location on the skin surface of the individual, a condition of the selected one or more treatment agents, a condition of the one or more treatment agent reservoirs, or any other condition of the skin-treatment delivery device. In an aspect, the method includes emitting one or more audible signals with an audible signal-generating component of the skin-treatment delivery device. In an aspect, the method includes emitting one or more optical signals with an optical signal-generating component of the skin-treatment delivery device. In an aspect, the method includes emitting one or more haptic signals with a haptic signal-generating component of the skin-treatment delivery device. In an aspect, the method further includes emitting the one or more signals with the signal-generating component of the skin-treatment delivery device to notify the user that the location on the skin surface of the individual is inside a boundary of the microbe profile. For example, the method can include emitting one or more audible, optical, or haptic signals to notify the user if the current measured location on the skin surface of the individual is inside the boundary of the microbe profile. In an aspect, the method further includes emitting the one or more signals with the signal-generating component of the skin-treatment delivery device to notify the user that the location on the skin surface of the individual is outside a boundary of the microbe profile. For example, the method can include emitting one or more audible, optical, or haptic signals to notify the user if the current measured location on the skin surface of the individual is outside the boundary of the microbe profile, indicating that the user should move the skin-treatment delivery device to a location within the boundary of the microbe profile. In an aspect, the method includes emitting the one or more signals with the signal-generating component of the skin-treatment delivery device to notify the user upon proximity of the skin-treatment delivery device to a treatment location associated with the microbe profile. In an aspect, the method includes emitting the one or more signals with the signal-generating component of the skin-treatment delivery device to notify the user in response to completion of delivery of the selected one or more treatment agents at a treatment location associated with the microbe profile. In an aspect, the method includes emitting the one or more signals with the signal-generating component of the skin-treatment delivery device to notify a user of a future treatment location. In an aspect, the method further includes emitting the one or more signals with the signal-generating component of the skin-treatment delivery device to notify a user to interact with an actuation component of the skin-treatment delivery device for manual actuation of the controllable valve of at least one of the one or more treatment agent reservoirs. For example, the method can include emitting one or more audible, optical, or haptic signals to the user to indicate that the device is in an appropriate location for manual actuation of the controllable valve of at least one of the one or more treatment agent reservoirs. In an aspect, the method includes emitting one or more signals with the signal-generating component of the skin-treatment delivery device to notify a user that the selected one or more treatment agents are not available in the one or more treatment agent reservoirs. In an aspect, the method includes emitting one or more signals with the signal-generating component of the skin-treatment delivery device to notify a user to replace at least one of the one or more treatment agent reservoirs to include at least one treatment agent reservoir including the selected one or more treatment agents.

In an aspect, the method includes recording delivery data to the data storage component of the skin-treatment delivery device, the delivery data including the location on the skin surface of the individual and the one or more treatment agents delivered to said location, as shown in block 1710 of FIG. 17. For example, the method can include recording which treatments are delivered to the skin surface as the skin-treatment delivery device is moved from one location to another over the skin surface of the individual. In an aspect, the delivery data can further include dosing information, e.g., how much of the one or more treatment agents were delivered to said location. In an aspect, the delivery data can further include the time of dosing, e.g., what time of day were the one or more treatment agents applied to the skin surface of the individual. In an aspect, the method includes converting the recorded delivery data into a treatment map. For example, the method can include recording delivery data while manually actuating the controllable valve of at least one of the one or more treatment agent reservoirs while moving from one location to another over the skin surface of the individual and converting said delivery data into a treatment map for future use. In an aspect, the method includes retrieving recorded delivery data from a past delivery event to inform a future delivery event, as shown in block 1720 of FIG. 17.

In an aspect, the method includes actuating the controllable valve of at least one of the one or more treatment agent reservoirs in response to a user interacting with an actuation component on the skin-treatment delivery device, as shown in block 1730 of FIG. 17. For example, the method can include pushing a button or flipping a switch attached to the outside of the skin-treatment delivery device to manually actuate the controllable valve of at least one of the one or more treatment agent reservoirs. For example, the method can include pushing a button or flipping a switch attached to the outside of the skin-treatment delivery device to manually actuate the controllable valve in response to a signal, e.g., an optic, audible, or haptic signal, indicating an appropriate location on the skin surface of the individual to deliver one or more treatment agents.

FIG. 18 shows a flowchart of a method for delivering a treatment to a skin surface based on a treatment map. The method includes in block 1800 receiving information associated with a location on the skin surface of an individual from a location-capture component of a skin-treatment delivery device, the skin-treatment delivery device including the location-capture component; one or more treatment agent reservoirs, each of the one or more treatment agent reservoirs including at least one port with a controllable valve; at least one conduit in fluid communication with the at least one port with the controllable valve and an opening defined by a surface of the skin-treatment delivery device; a data storage component configured to store information associated with a treatment map, the treatment map including a two-dimensional spatial distribution of one or more treatment agents for application on the skin surface of the individual; and a computing component including a processor and circuitry, the computing component operably coupled to the location-capture component, the controllable valve of each of the one or more treatment agent reservoirs, and the data storage component. The method further includes in block 1810 correlating the received information associated with the location on the skin surface of the individual with stored information associated with the treatment map to select the one or more treatment agents for application at said location on the skin surface of the individual. The method further includes in block 1820 actuating the controllable valve of at least one of the one or more treatment agent reservoirs to modulate release of the selected one or more treatment agents for application to said location on the skin surface of the individual. In an aspect, the method includes at least partially opening or closing the controllable valve of at least one of the one or more treatment agent reservoirs to modulate release of the selected one or more treatment agents.

FIG. 19 shows further aspects of a method for delivering a treatment to a skin surface based on a treatment map. In an aspect, a method of delivering a treatment to a skin surface includes receiving information associated with the location on the skin surface of the individual from at least one of an image capture device, a fiducial reader, or an inertial navigation device. In an aspect, the method includes receiving an update to the information associated with the location on the skin surface of the individual form the location-capture component in response to moving the skin-treatment delivery device to a new location on the skin surface of the individual, as shown in block 1900.

In an aspect, the method further includes receiving the information associated with the treatment map from a remote source, as shown in block 1910. In an aspect, the method includes receiving the information associated with the treatment map from at least one of a microbe profiling device, a second computing device, or the Internet. In an aspect, the method includes receiving an update to the information associated with the treatment map, as shown in block 1920. For example, the method can include receiving an update to the treatment map that includes an addition or subtraction of one or more treatment agents. For example, the method can include receiving an update to the treatment map that includes a redistribution or a change in dose of the one or more treatment agents over a treatment area, e.g., the face of an individual. In an aspect, the method includes receiving an update to the information associated with the treatment map in response to an update to a microbe profile, as shown in block 1930. For example, a change in the spatial distribution and/or identity of one or more types of microbes making up the microbe profile may lead to a change in the treatment map, either in where a particular treatment agent is applied or the type of treatment agent applied to a particular location. In an aspect, the method includes receiving an update to the information associated with the treatment map in response to changes in treatment practice. For example, the method can include receiving an update to the information associated with the treatment map that includes a new treatment agent, e.g., a new probiotic or prebiotic agent. For example, the method can include receiving an update to the information associated with the treatment map that includes a different antimicrobial agent, anti-inflammatory, or chemotherapy agent.

In an aspect, the method includes correlating the received information associated with the location on the skin surface of the individual with the stored information associated with the treatment map to select the one or more treatment agent for application at said location on the skin surface of the individual by aligning the received information associated with location on the skin surface of the individual with one or more reference locations embedded in the treatment map, as shown in block 1940 of FIG. 19. In an aspect, the method includes aligning the received information associate with the location on the skin surface of the individual with one or more reference locations on a feature map embedded in the treatment map. In an aspect, the method includes aligning one or more images of the location on the skin surface of the individual with images of the one or more reference locations embedded in the treatment map. In an aspect, the method includes aligning one or more fiducial markers of the location on the skin surface of the individual with fiducial markers of one or more reference locations embedded in the treatment map. In an aspect, the method includes aligning one or more coordinates of the location of the skin surface of the individual with coordinates of one or more reference locations embedded in the treatment map. In an aspect, the method further includes alerting a user if the correlation between the received information associated with the location on the skin surface of the individual and the stored information associated with the treatment map indicates that the location on the skin surface of the individual is outside a boundary of the treatment map, as shown in block 1950.

FIG. 20 shows further aspects of a method of delivering a treatment to a skin surface. In an aspect, the method includes emitting one or more signals with a signal-generating component of the skin-treatment delivery device to notify a user of a condition, as shown in block 2000. In an aspect, the method includes emitting one or more audible signals, e.g., beeps, with an audible signal-generating component of the skin-treatment delivery device. In an aspect, the method includes emitting one or more optical signals, e.g., a flashing light, with an optical signal-generating component of the skin-treatment delivery device. In an aspect, the method includes emitting one or more haptic signals, e.g., rumbling the device, with a haptic signal-generating component of the skin-treatment delivery device. In an aspect, the method includes emitting the one or more signals with the signal-generating component of the skin-treatment delivery device to notify a user that the location on the skin surface of the individual is outside a boundary of the treatment map. In an aspect, the method includes emitting the one or more signals with the signal-generating component of the skin-treatment delivery device to notify a user that the location on the skin surface of the individual is inside a boundary of the treatment map. In an aspect, the method includes emitting the one or more signals with the signal-generating component of the skin-treatment delivery device to notify a user to modify motion of the device, e.g., to slow down near a specific treatment location. In an aspect, the method includes emitting the one or more signals with the signal-generating component of the skin-treatment delivery device to notify a user upon proximity of the skin-treatment delivery device to a treatment location associated with the treatment map. In an aspect, the method includes emitting the one or more signals with the signal-generating component of the skin-treatment delivery device to notify a user in response to completion of delivery of the selected one or more treatment agents at a treatment location associated with the treatment map. In an aspect, the method includes emitting the one or more signals with the signal-generating component of the skin-treatment delivery device to notify a user of a future treatment location. In an aspect, the method includes the emitting one or more signals with the signal-generating component of the skin-treatment delivery device to notify a user to interact with an actuation component of the skin-treatment delivery device to manually actuate the controllable valve of at least one of the one or more treatment agent reservoirs.

In an aspect, a method of delivering a treatment to a skin surface includes recording delivery data to the data storage component of the skin-treatment delivery device, the delivery data including the location on the skin surface of the individual and the one or more treatment agents delivered to said location, as shown in block 2010. In an aspect, the delivery data further includes at least one of the dose of each of the one or more treatment agents, the time of day of treatment, or any other information associated with dosing the one or more treatment agents. In an aspect, the method includes converting the delivery data into a treatment map for future use. In an aspect, the method further includes retrieving recorded delivery data from a past delivery event to inform a future delivery event, as shown in block 2020. In an aspect, a method of delivering a treatment to a skin surface includes actuating the controllable valve of at least one of the one or more treatment agent reservoirs in response to a user interacting with an actuation component on the skin-treatment delivery device, as shown in block 2030. In an aspect, method includes recording delivery data while manually actuating the controllable valve and converting the recorded delivery data into a treatment map for future use.

Generating a Treatment Map

FIG. 21 shows a flowchart of a method for generating a treatment map from a microbe profile. The method for generating the treatment map is implemented on a computing device. The method includes receiving a two-dimensional microbe profile of a skin surface of an individual, the two-dimensional microbe profile including a two-dimensional spatial distribution of one or more types of microbes at each of one or more locations on the skin surface of the individual, as shown in block 2100. The method further includes selecting one or more treatment agents from a database of treatment agents, the selected one or more treatment agents to treat at least one of the one or more types of microbes at each of the one or more locations on the skin surface of the individual, as shown in block 2110. The method includes generating the treatment map by mapping the selected one or more treatment agents to treat the at least one of the one or more types of microbes at each of the one or more locations on the skin surface of the individual to each of one or more corresponding locations on the two-dimensional microbe profile of the skin surface of the individual, as shown in block 2120. The method further includes reporting the generated treatment map to a user, as shown in block 2130.

In an aspect, the method includes generating the treatment map from a microbe profile using a computing device, e.g., a desktop computer. In an aspect, the method includes generating the treatment map from a microbe profile using a computing device associated with a microbe profiling system or microbe profiling device. In an aspect, the method includes generating the treatment map from a microbe profile using a computing component associated with a skin-treatment delivery device.

FIG. 22 shows further aspects of a method for generating a treatment map. The method for generating a treatment map includes receiving a two-dimensional microbe profile of the skin surface of an individual. In an aspect, the method includes receiving the two-dimensional microbe profile from an internal source, as shown in block 2200. For example, the method can include using a computing component or device associated with microbe profiling device or system to generate a treatment map from a microbe profile generated by said microbe profiling device or system. In an aspect, the method includes receiving the two-dimensional microbe profile from an external source, as shown in block 2210. In an aspect, the method includes receiving the two-dimensional microbe profile from at least one of a microbe profiling device, a second computing device, or the Internet, as shown in block 2220.

In an aspect, the method includes receiving the two-dimensional microbe profile overlaid with a feature map of the skin surface of the individual, the feature map of the skin surface of the individual including at least one of an image map, a fiducial marker map, or a coordinate map of the skin surface of the individual, as shown in block 2230.

FIG. 23 shows further aspects of a method of generating a treatment map implemented on a computing device. The method includes selecting one or more treatment agents from a database of treatment agents. In an aspect, the method includes selecting the one or more treatment agents from a database of treatment agents stored in the computing device, as shown in block 2300. For example, the computing device used for generating the treatment map can include a stored database of treatment agents, the database including one or more treatment agents matched with one or more types of microbes. In an aspect, the method includes selecting the one or more treatment agents from a database of treatment agents stored in a remote location, as shown in block 2310. For example, the method can include selecting the one or more treatment agents from a database of treatment agents stored on a second computing device, the second computing device accessible by wireless communication, e.g., through the Internet. In an aspect, the method includes comparing the one or more selected treatment agents with a second database of treatment agents identified as either compatible or non-compatible with the individual. For example, the method can include comparing the selected one or more treatment agents with a second database personalized for the individual and containing treatment agents to which the individual is allergic or sensitive, e.g., a particular antibiotic.

In an aspect, the method includes selecting one or more probiotics from the database of treatment agents, as shown in block 2320. Non-limiting examples of probiotics have been described above herein. In an aspect, the method includes selecting one or more prebiotics from the database of treatment agents, as shown in block 2330. For example, the method can include selecting prebiotics from the database of treatment agents to promote maintenance or growth of "good" microbes on the skin surface of the individual. Non-limiting examples of prebiotics have been described above herein. In an aspect, the method includes selecting one or more of an antimicrobial agent, a therapeutic agent, or a chemotherapeutic agent from the database of treatment agents, as shown in block 2340. For example, the method can include selecting an antibacterial agent from the database of treatment agents to treat one or more bacterial types at a location on the skin surface of the individual.

The method of generating a treatment map implemented on a computing device includes generating the treatment map by mapping the selected one or more treatment agents to treat the at least one of the one or more types of microbes at each of one or more locations on the skin surface of the individual to each of one or more corresponding locations on the two-dimensional microbe profile of the skin surface of the individual. In an aspect, the method includes incorporating the information associated with the selected one or more treatment agents at each of the one or more corresponding locations on the two-dimensional microbe profile, as shown in block 2350 of FIG. 23. In an aspect, the method further includes incorporating information associated with at least one of a name, dose, or a dose schedule associated with the selected one or more treatment agents at each of the one or more corresponding locations on the two-dimensional microbe profile, as shown in block 2370.

In an aspect, the method includes selecting a treatment route based upon at least one of a correlation between microbe profiles at different locations and a correlation between selected treatment agents at different location. In an aspect, the method includes selecting a treatment route that includes a temporal component. For example, the method may include indicating in the treatment map that a first treatment agent needs to be administered at a given location before a second treatment agent is administered. In an aspect, the method includes selecting a treatment route that includes a spatial component. For example, the method may include indicating in the treatment map the administration of a first treatment agent at all appropriate locations for that agent should precede administration of second treatment agent at all appropriate locations for that second agent.

FIG. 24 shows further aspects of a method of generating a treatment map implemented with a computing device. In an aspect, the method includes mapping the selected one or more treatment agents to treat the at least one of the one or more types of microbes at each of the one or more locations on the skin surface of the individual to each of one or more corresponding locations on a feature map associated with the two-dimensional microbe profile, as shown in block 2400. In an aspect, the method includes mapping the selected one or more treatment agents to a feature map including one or more images associated with one or more locations on the skin surface of the individual. In an aspect, the method includes mapping the selected one or more treatment agents to a feature map including one or more fiducial markers associated with one or more locations on the skin surface of the individual. In an aspect, the method includes mapping the selected one or more treatment agents to a feature map include one or more coordinates associated with one or more locations of the skin surface of the individual.

In an aspect, the method further includes reporting the generated treatment map to a user. In an aspect, the method includes reporting the generated treatment map to a user who is the individual being treated. In an aspect, the method includes reporting the generated treatment map to a user who is a medical practitioner or other professional treating the individual. In an aspect, the method includes reporting the generated treatment map to a user who is a distributer or manufacturer of the one or more treatment agents. For example, the method can include reporting the treatment map to a computing device associated with a pharmacy or a cosmetics counter. In an aspect, the method includes reporting the generated treatment map to the user on a display, e.g., the display of the computing device, as shown in block 2410 of FIG. 24. In an aspect, the method includes reporting the generated treatment map to the user on a printout, as shown in block 2420. For example, the generated treatment map can be printed out using a printer operably coupled to the computing device. In an aspect, the method includes reporting the generated treatment map to the user on a second computing device, as shown in block 2430.

In an aspect, the method further includes transmitting information associated with the generated treatment map. In an aspect, the method includes transmitting information associated with the generated treatment map to a remote source, as shown in block 2440 of FIG. 24. For example, the method can include generating the treatment map on a first computing device and then sending the generated treatment map to a second device. In an aspect, the method includes transmitting information associated with the generated treatment map to a second computing device, as shown in block 2450. For example, the method can include transmitting the information associated with the generated treatment map to a personal communication device, e.g., a mobile phone. For example, the method can include transmitting the information associated with the generated treatment map to a personal computer, e.g., a lap top or tablet computing device. For example, the method can include transmitting the information associated with the generated treatment map to a distributer of the one or more treatment agents, e.g., a pharmacy or a cosmetics counter. In an aspect, the method includes transmitting the information associated with the generated treatment map to a skin-treatment delivery system, non-limiting examples of which have been described above herein. In an aspect, the method includes transmitting information associated with the generated treatment map to a skin-treatment delivery device, as shown in block 2460. For example, the method can include transmitting the information associated with the generated treatment map to a skin-treatment delivery device such as described herein through a wired communication link, e.g., a USB link, or through a wireless communication link, e.g., a Bluetooth communication link. For example, the method can include transmitting the information associated with the generated treatment map to a portable data storage component, e.g., a memory card, for use with a skin-treatment delivery device or a skin-treatment delivery system. In an aspect, the generated treatment map is used to inform delivery of the selected one or more treatment agents to one or more locations on the skin surface of the individual.

FIG. 25 illustrates aspects of a system for generating a treatment map. System 2500 includes circuitry for generating a treatment map. System 2500 includes circuitry 2510 for receiving a two-dimensional microbe profile of a skin surface of an individual, the two-dimensional microbe profile including a two-dimensional spatial distribution of one or more types of microbes at each of one or more locations on the skin surface of the individual. System 2500 includes circuitry 2520 for selecting one or more treatment agents from a database of treatment agents, the selected one or more treatment agents to treat at least one of the one or more types of microbes at each of the one or more locations on the skin surface of the individual. System 2500 further includes circuitry 2530 for generating the treatment map by mapping the selected one or more treatment agents to treat the at least one of the one or more types of microbes at each of the one or more locations on the skin surface of the individual to one or more corresponding locations on the two-dimensional microbe profile of the skin surface of the individual. System 2500 further includes circuitry 2540 for reporting the generated treatment map to a user. In an aspect, system 2500 includes a computing device.

In an aspect, system 2500 includes circuitry for receiving the two-dimensional microbe profile. In an aspect, the system includes circuitry for receiving the two-dimensional microbe profile from an internal source, e.g., the computing device. In an aspect, the system includes circuitry for receiving the two-dimensional microbe profile from an external source, e.g., from a second computing device or the Internet. In an aspect, the system includes circuitry for receiving the two-dimensional microbe profile from computing component of a microbe profiling device or a computing device associated with a microbe profiling system. In an aspect, the system includes circuitry for receiving the two-dimensional microbe profile overlaid with a feature map of the skin surface of the individual, the feature map of the skin surface of the individual including at least one of an image map, a fiducial marker map, or a coordinate map of the skin surface of the individual.

In an aspect, system 2500 includes circuitry for selecting one or more treatment agents from a database of treatment agents. In an aspect, the system includes circuitry for selecting the one or more treatment agents from a database of treatment agents stored in the computing device. In an aspect, the system includes circuitry for selecting the one or more treatment agents from a database of treatment agents stored in a remote location, e.g., stored on a second computing device accessible through the Internet or other communications link. In an aspect, the system includes circuitry for selecting one or more probiotics from the database of treatment agents. In an aspect, the system includes circuitry for selecting one or more prebiotics from the database of treatment agents. In an aspect, the system includes circuitry for selecting one or more of an antimicrobial agent, a therapeutic agent, or a chemotherapeutic agent from the database of treatment agents. In an aspect, the system further includes circuitry for incorporating information associated with the selected one or more treatment agents at each of the one or more corresponding locations on the two-dimensional microbe profile. In an aspect, the system includes circuitry for incorporating information associated with at least one of a name, a dose, or a dosing schedule associated with the selected one or more treatment agents at each of the one or more corresponding locations on the two-dimensional microbe profile. In an aspect, the system includes circuitry for mapping the selected one or more treatment agents to treat the at least one of the one or more types of microbes at each of one or more locations on the skin surface of the individual to each of one or more corresponding locations on a feature map associated with the two-dimensional map, the feature map including at least one of an image map, a fiducial marker map, or a coordinate map.

In an aspect, system 2500 includes circuitry for reporting the generated treatment map to a user. In an aspect, the system includes circuitry for reporting the generated treatment map to the user on a display. In an aspect, the system includes circuitry for reporting the generated treatment map to the user on a printout. In an aspect, the system includes circuitry for reporting the generated treatment map to the user on a second computing device. In an aspect, system 2500 further includes circuitry for transmitting information associated with the generated treatment map. In an aspect, the system includes circuitry for transmitting the information associated with the generated treatment map to a remote source. In an aspect, the system includes circuitry for transmitting the information associated with the generated treatment map to a second computing device. For example, the system can include circuitry for transmitting the information associated with the generated treatment map via the Internet to a second computing device, e.g., a computing device associated with a pharmacy, a cosmetic counter, or other distributer of the one or more treatment agents. In an aspect, the system includes circuitry for transmitting the information associated with the generated treatment map to a skin-treatment delivery device. For example, the system can include circuitry for transmitting the information associated with the generated treatment map through a Bluetooth or other wireless communications link. In an aspect, the system includes circuitry for transmitting the information associated with the generated treatment map to a data storage component of a skin-treatment delivery device.

FIG. 26 illustrates aspects of a system for generating a treatment map. System 2600 includes computing device 2610 and circuitry 2620. Circuitry 2620 includes circuitry 2630 for receiving a two-dimensional microbe profile of a skin surface of an individual, the two-dimensional microbe profile including a two-dimensional spatial distribution of one or more types of microbes at each of one or more locations on the skin surface of the individual. Circuitry 2620 includes circuitry 2640 for selecting one or more treatment agents from a database of treatment agents, the selected one or more treatment agents to treat at least one of the one or more types of microbes at each of the one or more locations on the skin surface of the individual. Circuitry 2620 further includes circuitry 2650 for generating the treatment map by mapping the selected one or more treatment agents to treat the at least one of the one or more types of microbes at each of the one or more locations on the skin surface of the individual to one or more corresponding locations on the two-dimensional map of the skin surface of the individual. Circuitry 2620 further includes circuitry 2660 for reporting the generated treatment map to a user.

FIG. 27 shows aspects of a system for generating a treatment map. System 2700 includes computing device 2710 including a processor and non-transitory signal bearing medium 2720. Non-transitory signal-bearing medium 2720 includes one or more instructions for generating a treatment map. Non-transitory signal-bearing medium 2720 includes one or more instructions 2730 for receiving a two-dimensional microbe profile of a skin surface of an individual, the two-dimensional microbe profile including a two-dimensional distribution of one or more types of microbes at each of one or more locations of the skin surface of the individual. Non-transitory signal-bearing medium 2720 includes one or more instructions 2740 for selecting one or more treatment agents from database of treatment agents, the selected one or more treatment agents to treat at least one of the one or more types of microbes at each of the one or more locations on the skin surface of the individual. Non-transitory signal-bearing medium 2720 includes one or more instructions 2750 for generating a treatment map by mapping the selected one or more treatment agents to treat the at least one of the one or more types of microbes at each of the one or more locations on the skin surface of the individual to each of one or more corresponding locations on the two-dimensional microbe profile of the skin surface of the individual. Non-transitory signal-bearing medium 2720 further includes one or more instructions 2760 for reporting the generated treatment map to a user.

System 2700 includes non-transitory signal-bearing medium 2720 including one or more instructions for receiving the two-dimensional microbe profile. In an aspect, the non-transitory signal-bearing medium includes one or more instructions for receiving the two-dimensional microbe profile from an internal source, e.g., from within the computing device. In an aspect, the non-transitory signal-bearing medium includes one or more instructions for receiving the two-dimensional microbe profile from an external source. In an aspect, the non-transitory signal-bearing medium one or more instructions for receiving the two-dimensional microbe profile from a microbe profiling device. In an aspect, the non-transitory signal-bearing medium includes one or more instructions for receiving the two-dimensional map from a second computing device, e.g., a computing device in an office of a microbe profiling service provider. In an aspect, the non-transitory signal-bearing medium includes one or more instructions for receiving the two-dimensional microbe profile through the Internet. In an aspect, the non-transitory signal-bearing medium includes one or more instructions for receiving the two-dimensional microbe profile overlaid with a feature map of the skin surface of the individual, the feature map of the skin surface of the individual including at least one of an image map, a fiducial marker map, or a coordinate map of the skin surface of the individual.

System 2700 includes non-transitory signal-bearing medium 2720 including one or more instructions for selecting one or more treatment agents from a database of treatment agents. In an aspect, the non-transitory signal-bearing medium includes one or more instructions for selecting the one or more treatment agents from a database of treatment agents included in the computing device. In an aspect, the non-transitory signal-bearing medium includes one or more instructions for selecting the one or more treatment agents from a database of treatment agents stored in a remote location, e.g., on a second computing device accessible through the Internet. In an aspect, the non-transitory signal-bearing medium includes one or more instructions for selecting one or more probiotic agents from the database of treatment agents. In an aspect, the non-transitory signal-bearing medium includes one or more instructions for selecting one or more prebiotic agents from the database of treatment agents. In an aspect, the non-transitory signal-bearing medium includes one or more instructions for selecting at least one of an antimicrobial agent, a therapeutic agent, or a chemotherapeutic agent from the database of treatment agents. In an aspect, the non-transitory signal-bearing medium includes one or more instructions for incorporating information associated with the selected one or more treatment agents at each of the one or more corresponding locations on the two-dimensional microbe profile. In an aspect, the non-transitory signal-bearing medium includes one or more instructions for incorporating information associated with at least one of a name, a dose, or a dosing schedule associated with the selected one or more treatment agents at each of the one or more corresponding locations on the two-dimensional microbe profile. In an aspect, the non-transitory signal-bearing medium includes one or more instructions for mapping the selected one or more treatment agents to treat the at least one of the one or more types of microbes at each of the one or more locations on the skin surface of the individual to each of one or more corresponding locations on a feature map associated with the two-dimensional microbe profile.

System 2700 includes non-transitory signal-bearing medium 2720 including one or more instructions for reporting the generated treatment map to a user. In an aspect, non-transitory signal-bearing medium includes one or more instructions for reporting the generated treatment map to a user on a display, e.g., a display associated with computing device 2710. In an aspect, the non-transitory signal-bearing medium includes one or more instructions for reporting the generated treatment map to the user on a printout, e.g., using a printer operably coupled to computing device 2710. In an aspect, the system includes one or more instructions for reporting the generated treatment map to a user on a second computing device, e.g., a personal computing device or a mobile phone device.

System 2700 further non-transitory signal-bearing medium 2720 including one or more instructions for transmitting information associated with the generated treatment map. In an aspect, the non-transitory signal-bearing medium includes one or more instructions for transmitting information associated with the generated treatment map to a remote source. In an aspect, the non-transitory signal-bearing medium includes one or more instructions for transmitting information associated with the generated treatment map to a second computing device. In an aspect, the non-transitory signal-bearing medium includes one or more instructions for transmitting information associated with the generated treatment map to a skin-treatment delivery device. In an aspect, the non-transitory signal-bearing medium includes one or more instructions for transmitting information associated with the generated treatment map to a data storage component of a skin-treatment delivery device.

FIG. 28 shows aspects of an article of manufacture. Article of manufacture 2800 includes non-transitory signal-bearing medium 2810. Non-transitory signal-bearing medium 2810 includes one or more instructions for generating a treatment map. The one or more instructions include one or more instructions 2820 for receiving a two-dimensional microbe profile of a skin surface of an individual, the two-dimensional microbe profile including a two-dimensional spatial distribution of one or more types of microbes at each of one or more locations on the skin surface of the individual; one or more instructions 2830 for selecting one or more treatment agents from a database of treatment agents, the selected one or more treatment agents to treat at least one of the one or more types of microbes at each of the one or more locations on the skin surface of the individual; one or more instructions 2840 for generating the treatment map by mapping the selected one or more treatment agents to treat the at least one of the one or more types of microbes at each of the one or more locations on the skin surface of the individual to one or more corresponding locations on the two-dimensional microbe profile of the skin surface of the individual; and one or more instructions 2850 for reporting the generated treatment map to a user.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software (e.g., a high-level computer program serving as a hardware specification) implementation; or, yet again alternatively, the implementer may opt for some combination of hardware, software (e.g., a high-level computer program serving as a hardware specification), and/or firmware in one or more machines, compositions of matter, and articles of manufacture, limited to patentable subject matter under 35 U.S.C. § 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software (e.g., a high-level computer program serving as a hardware specification), and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software (e.g., a high-level computer program serving as a hardware specification) or firmware, or of gate arrays or programmable hardware, such as by performing a reception of or a transmission of one or more instructions in relation to one or more operations described herein. Alternatively or additionally, in some variants, an implementation can include special-purpose hardware, software (e.g., a high-level computer program serving as a hardware specification), firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, implementations may be provided, in whole or in part, by source code, such as C++ or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those skilled within the art that each function and/or operation within such block diagrams, flowcharts, or examples can be implemented, individually and/or collectively, by a wide range of hardware, software (e.g., a high-level computer program serving as a hardware specification), firmware, or virtually any combination thereof, limited to patentable subject matter under 35 U.S.C. 101. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. 101, and that designing the circuitry and/or writing the code for the software (e.g., a high-level computer program serving as a hardware specification) and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software (e.g., a high-level computer program serving as a hardware specification), firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications, programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

PROPHETIC EXAMPLES

Example 1: Skin-Treatment Delivery Device with a Treatment Map

A skin-treatment delivery device including a treatment map is described for treating Methicillin-Resistant *Staphylococcus aures* (MRSA) with a probiotic bacteria. The skin-treatment delivery device includes a plastic hand-held housing encasing the components of the skin-treatment delivery device including a treatment agent reservoir, an image-capture device, a docking site for a removable memory card, and a computing component.

The treatment agent reservoir includes a single port with a controllable spray valve. The treatment agent reservoir is filled with a suspension of probiotic, e.g., *Propionibacterium acnes* at a concentration of $10^5$ CFU/ml (ATCC9341; see Shu et al. (2013) PLoS ONE 8(2):e55380, which is incorporated herein by reference), in a biocompatible liquid, e.g., buffered saline and glycerol. The probiotic suspension further includes a pharmaceutical grade liquid propellant, e.g., 1,1,1,2-tetrafluoroethane (HFA-134a, from, e.g., DuPont, Wilmington, Del.), for use in generating an aerosol spray upon actuation of the spray valve.

The image-capture device includes the components of a small digital camera, such as that used in smart phone technology. See, e.g., Hayes "Next Generation Cell Phone Cameras," *Optics & Photonics News*, February 2012, pp. 16-21. The small digital camera includes a CMOS (complementary metal-oxide-semiconductor) image sensor as part of a digital camera module, examples of which are available from commercial sources (from, e.g., STMicroelectronics, Geneva, Switzerland; Toshiba America Electronic Components, Inc., Irvine, Calif.). The image-capture device may further include a flash unit in the form of an LED and autofocus functions.

A microbe profile including the two-dimensional spatial distribution of MRSA on the skin surface of the torso of an individual generated using a microbe profiling device as described in U.S. patent application Ser. No. 14/091,762 to Baym et al. titled "Devices and Methods for Profiling Microbiota of Skin," which is incorporated herein by reference, using a microbe capture region with a MRSA-specific antibody (from, e.g., Lifespan Biosciences Inc., Seattle, Wash.). The MRSA profile includes a fiducial marker map including physical landmarks, e.g., moles, on the skin surface of the torso of the individual. The MRSA profile including the fiducial marker map is transmitted to a computing device, e.g., a desktop computer in the medical practitioner's office, which includes circuitry to generate the MRSA treatment map. The circuitry associated with the desktop computer receives the MRSA profile from the microbe profiling device, e.g., from a removable data storage device such as a memory card, selects an agent, e.g., the suspension of probiotic *Propionibacterium acnes*, from a database of treatment agents stored in the desktop computer, and maps the application sites for the suspension of probiotic *Propionibacterium acnes* with the distribution of MRSA on the skin surface of the individual as indicated from the MRSA profile. The database of treatment agents can include a look-up table that matches treatment agents, e.g., probiotics, prebiotics, antimicrobials, therapeutic agents, chemotherapy agents, and immunomodulators, with specific microbes, e.g., with species and/or strains of bacteria, fungi, or viruses. The MRSA treatment map, including the fiducial marker map, is reported to a display associated with the desktop computer for viewing by the medical practitioner and can be printed to provide a hard copy of the MRSA treatment map to the individual. In addition, the MRSA treatment map can be transmitted to the skin-treatment delivery device by downloading the MRSA treatment map from the desktop computer and onto the memory card and inserting the memory card into skin-treatment delivery device.

The skin-treatment delivery device includes a computing component with a microprocessor and circuitry configured to perform various operations or instructions. The skin-treatment delivery device also includes a user interface, e.g., a small touchscreen display.

In operation, the individual being treated is instructed to lie down on his/her stomach while exposing the skin surface of the back torso to a medical practitioner. The medical practitioner slowly moves the hand-held skin-treatment delivery device over the skin surface. The image-capture device captures images including the fiducial markers, e.g., moles, on the skin surface. The circuitry of the computing component receives the information associated with the images and correlates this information with the MRSA treatment map and the fiducial marker map to determine which locations on the torso are indicated for treatment with the suspension of probiotic *Propionibacterium acnes*. A pattern matching algorithm is used for this correlation. The controllable valve of the treatment agent reservoir is actuated by an electrical current to release the suspension of probiotic *Propionibacterium acnes* at the locations on the torso that are indicated for treatment.

Example 2: Skin-Treatment Delivery Device with a Microbe Profile

A skin-treatment delivery device including a microbe profile is described for selectively treating gram-positive bacteria, e.g., *Staphylococcus aureus*, gram-negative bacteria, e.g., *Pseuodomonas aeruginosa*, and fungi, e.g., *Candida*, with antimicrobial agents. The skin-treatment delivery device includes a plastic hand-held housing encasing the components of the skin-treatment delivery device including three treatment agent reservoirs, an image-capture device, a docking site for a flash memory card, a signal-generating component, and a computing component.

Each of the three treatment agent reservoirs includes a single port with a controllable valve. The three treatment agent reservoirs are part of a modular system of replaceable reservoirs, each port of three treatment agent reservoirs controllably releases its contents into a common conduit in fluid communication with an opening in the hand-held housing of the device. Sprays emitted simultaneously from two or more of the treatment agent reservoirs mix on exit through the common conduit. In this example, the first treatment reservoir includes a solution of erythromycin for treating gram positive bacteria, e.g., *Staphylococcus aureus*, the second treatment reservoir includes a solution of polymyxin B for treating gram negative bacteria, e.g., *Pseuodomonas aeruginosa*, and the third treatment reservoir includes a solution of nystatin for treating the yeast fungus *Candida*. Each reservoir further includes a pharmaceutical grade liquid propellant, e.g., 1,1,1,2-tetrafluoroethane (HFA-134a, from, e.g., DuPont, Wilmington, Del.), for use in generating an aerosol spray upon actuation of the controllable valve.

The image-capture device includes the components of a small digital camera, such as that used in smart phone technology as described in Example 1. The image-capture device may further include a flash unit in the form of an LED and autofocus functions.

A microbe profile of the skin surface of the face of an individual is generated using a microbe profiling device as described in U.S. patent application Ser. No. 14/091,762 to Baym et al. titled "Devices and Methods for Profiling Microbiota of Skin," which is incorporated herein by reference. The microbe profile includes the two-dimensional spatial distribution of gram-positive bacteria *Staphylococcus aureus*, gram-negative bacteria *Pseuodomonas aeruginosa*, and fungus *Candida* on the skin surface of the individual's face. The microbe profile includes a feature map, e.g., a wide-angle photographic image, of the skin surface of the individual encompassed by the microbe profile. The information associated with the microbe profile is transferred from the microbe profiling device to a flash memory card, e.g., a microSD card (from, e.g., SunDisk Corporation, Milpitas, Calif.), compatible with the skin-treatment delivery device. The flash memory card further includes a database of treatment agents including at least the agents included in the three treatment agent reservoirs, e.g., erythromycin, gentamicin, and nystatin. Other antimicrobial agents may also be included in the database of treatment agents.

The skin-treatment delivery device includes a computing component with a microprocessor and circuitry configured to perform various operations or instructions related to receiving location information, correlating a location with the microbe profile, selecting a treatment agent, and actuating a controllable valve. The skin-treatment delivery device further includes an audible signal-generating component, e.g., an audio chip, which is operably coupled to the computing component. The audible signal-generating component provides audible signals to the user during the course of treatment.

In operation, the individual being treated is instructed to sit in a reclining seat. The medical practitioner slowly moves the hand-held skin-treatment delivery device over the skin surface of the individual's face. The digital camera module captures images of the skin of the individual's face as the device moves from one location to the next. The audible signal-generating component provides an audible signal, e.g., a single beep, to notify the user to hold the current position of the device to allow imaging and application of treatment agents and a second audible signal, e.g., two beeps, to notify the user to move to another location on the skin surface. The circuitry of the computing component receives the information associated with the images and correlates this information with the microbe profile and the feature map to determine which microbes, gram-positive bacteria *Staphylococcus aureus*, gram-negative bacteria *Pseuodomonas aeruginosa*, and/or fungus *Candida*, are present at a given location. A pattern matching algorithm is used for this correlation. The circuitry further selects a treatment agent, e.g., erythromycin, gentamicin, and/or nystatin, from the database of treatment options. The controllable valves of the respective treatment agent reservoirs are actuated to modulate release of the treatment agents at the location. Once treatment is complete at a given location, the audible signal-generator beeps twice to notify the user to move to a new location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A skin-treatment delivery device, comprising:
  a hand-held housing including
    one or more treatment agent reservoirs, each of the one or more treatment agent reservoirs including at least one port with a controllable valve, each of the one or more treatment agent reservoirs configured to store and controllably release one or more treatment agents;
    at least one conduit in fluid communication with the at least one port with the controllable valve and an opening defined by a surface of the hand-held housing;
    a data storage component;
    a personalized microbe profile stored in the data storage component, the personalized microbe profile including a feature map of a skin surface of an individual overlaid with a two-dimensional spatial distribution of one or more types of microbes at each of one or more locations on the skin surface of the individual;
    a location-capture component including circuitry to measure a feature of a location on the skin surface of the individual; and
    a computing component including a processor, the computing component operably coupled to the controllable valve of each of the one or more treatment agent reservoirs, the data storage component, and the location-capture component, the computing component including circuitry to receive information associated with the measured feature of the location on the skin surface of the individual from the location-capture component;

map the received information associated with the measured feature of the location on the skin surface of the individual to the feature map associated with the personalized microbe profile to determine which of the one or more types of microbes of the personalized microbe profile is associated with said location;

select at least one of the one or more treatment agents stored in the one or more treatment reservoirs for application to said location on the skin surface of the individual based on which of the one or more types of microbes is associated with said location; and actuate the controllable valve of at least one of the one or more treatment agent reservoirs to modulate release of the selected at least one of the one or more treatment agents onto said location on the skin surface of the individual.

2. The device of claim 1, wherein at least one of the one or more treatment agent reservoirs comprises a replaceable cartridge.

3. The device of claim 1, wherein the one or more treatment agents include at least one of one or more probiotics, one or more prebiotics, one or more antimicrobial agents, or one or more therapeutic agents.

4. The device of claim 1, further comprising:
a mixing chamber including a mixing mechanism, the mixing chamber in fluid communication with the at least one conduit.

5. The device of claim 1, wherein the location-capture component comprises at least one of an image capture device, a fiducial reader, or an inertial navigation device.

6. The device of claim 1, wherein the feature map of the skin surface of the individual includes at least one of one or more images of the skin surface of the individual, one or more fiducial markers on the skin surface of the individual, or one or more coordinates overlaid with the two-dimensional distribution of the one or more types of microbes at each of the one or more locations on the skin surface of the individual.

7. The device of claim 1, wherein the data storage component includes circuitry to receive the information associated with the personalized microbe profile from a remote source.

8. The device of claim 1, wherein the personalized microbe profile comprises at least one of an identity, a quantity, or a relative abundance of at least one of the one or more types of microbes at each of the one or more locations on the skin surface of the individual.

9. The device of claim 1, wherein the information associated with the measured feature of the location on the skin surface of the individual comprises information associated with at least one of one or more images of the location on the skin surface of the individual, one or more fiducial markers of the location on the skin surface of the individual, or one or more coordinates representative of the location on the skin surface of the individual.

10. The device of claim 1, wherein the computing component comprises circuitry to align the measured feature of the location on the skin surface of the individual with features of one or more locations on the feature map of the skin surface of the individual embedded in the personalized microbe profile.

11. The device of claim 1, further comprising:
circuitry to alert a user if the selected at least one of the one or more treatment agents is not currently available in the one or more treatment agent reservoirs.

12. The device of claim 1, further comprising:
an actuation interface accessible on an outer surface of the hand-held housing, the actuation interface including circuitry to transmit one or more signals to the computing component, the computing component including circuitry to actuate the controllable valve of at least one of the one or more treatment agent reservoirs in response to the one or more signals received from the actuation interface.

13. The device of claim 1, further comprising:
an idealized microbe profile including the feature map of the skin surface of the individual overlaid with a two-dimensional spatial distribution of one or more types of microbes ideal for each of one or more locations on the skin surface of the individual; and
circuitry to
map the received information associated with the measured feature of the location on the skin surface of the individual to the feature map associated with the idealized microbe profile to determine which of the one or more types of microbes of the idealized microbe profile is ideal for said location; and
select at least one of the one or more treatment agents stored in the one or more treatment reservoirs for application to said location on the skin surface of the individual based on which of the one or more types of microbes is ideal for said location.

14. The device of claim 1, further comprising:
a signal-generating component operably coupled to the computing component and including circuitry to emit one or more signals in response to receiving one or more signals from the operably coupled computing component.

15. The device of claim 14, wherein the signal-generating component is operable to emit the one or more signals to notify a user of a condition.

16. The device of claim 1, wherein the computing component includes circuitry to store delivery data, wherein the delivery data includes at least one of a treatment agent, a dose, a location of application to the skin surface of the individual, a time, or a date.

17. The device of claim 16, wherein the computing component includes circuitry to convert the delivery data into a personalized treatment map including the feature map of the skin surface of the individual overlaid with a two-dimensional distribution of the one or more treatment agents administered at each of one or more locations on the skin surface of the individual.

18. The device of claim 1, further comprising
a microbe capture region configured to capture one or more microbes from one or more regions of the skin surface of the individual;
at least one sensor component including circuitry to detect one or more signals emitted or reflected from the microbe capture region, the one or more signals representative of the captured one or more microbes; and
the microbe capture region and the at least one sensor component operably coupled to the computing component, the computing component including circuitry to
receive information associated with the one or more regions of the skin surface of the individual from the location-capture component;

receive sensor output from the at least one sensor component, the sensor output including information associated with the detected one or more signals emitted or reflected from the microbe capture region;
map the information associated with the location of said one or more regions of the skin surface of the individual to the information associated with the detected one or more signals emitted or reflected from the microbe capture region; and
generate the personalized microbe profile based on the mapping of the information associated with the location of said one or more regions of the skin surface of the individual to the information associated with the detected one or more signals emitted or reflected from the microbe capture region, the personalized microbe profile including the two-dimensional spatial distribution of the one or more types of microbes at each of the one or more locations on the skin surface of the individual.

19. The device of claim 18, wherein the computing component includes circuitry to modify selection of at least one of the one or more treatment agents stored in the one or more treatment agent reservoirs in response to a difference between a measured personalized microbe profile and a stored personalized microbe profile.

20. A method of delivering a treatment to a skin surface, comprising:
receiving information associated with a measured feature of a location on the skin surface of an individual from a location-capture component of a skin-treatment delivery device, the skin-treatment delivery device including the location-capture component;
one or more treatment agent reservoirs, each of the one or more treatment agent reservoirs including at least one port with a controllable valve, each of the one or more treatment agent reservoirs configured to store and controllably release one or more treatment agents;
at least one conduit in fluid communication with the at least one port with the controllable valve and an opening defined by a surface of the skin-treatment delivery device;
a data storage component;
a personalized microbe profile stored in the data storage component, the personalized microbe profile including a feature map of the skin surface of the individual overlaid with a two-dimensional spatial distribution of one or more types of microbes at each of one or more locations on the skin surface of the individual; and
a computing component including a processor and circuitry, the computing component operably coupled to the location-capture component, the controllable valve of each of the one or more treatment agent reservoirs, and the data storage component;
mapping the received information associated with the measured feature of the location on the skin surface of the individual to the feature map associated with the personalized microbe profile to determine which of the one or more types of microbes of the personalized microbe profile is associated with said location on the skin surface of the individual;
selecting at least one of the one or more treatment agents stored in the one or more treatment reservoirs for application to said location on the skin surface of the individual based on which of the one or more types of microbes is associated with said location on the skin surface of the individual; and
actuating the controllable valve of at least one of the one or more treatment agent reservoirs to modulate release of the selected at least one of the one or more treatment agents onto said location on the skin surface of the individual.

21. The method of claim 20, further comprising:
receiving an update to the information associated with the measured feature of the location on the skin surface of the individual from the location-capture component in response to moving the skin-treatment delivery device to a new location on the skin surface of the individual.

22. The method of claim 20, wherein mapping the received information associated with the measured feature of the location on the skin surface of the individual to the feature map of the skin surface of the individual associated with the personalized microbe profile comprises aligning the received information associated with the measured feature of the location on the skin surface of the individual with a feature in the feature map embedded in the personalized microbe profile.

23. The method of claim 20, further comprising:
alerting a user if the mapping between the received information associated with the measured feature of the location on the skin surface of the individual and the feature map associated with the personalized microbe profile indicates that the location on the skin surface of the individual is outside a boundary of the personalized microbe profile.

24. The method of claim 20, further comprising:
actuating the controllable valve of at least one of the one or more treatment agent reservoirs in response to a user interacting with a button or switch on the skin-treatment delivery device.

25. The method of claim 20, further comprising:
emitting one or more signals with a signal-generating component of the skin-treatment delivery device to notify a user of a condition.

26. The method of claim 25, further comprising:
emitting the one or more signals with the signal-generating component of the skin-treatment delivery device to notify the user to interact with an actuation component of the skin-treatment delivery device for manual actuation of the controllable valve of at least one of the one or more treatment agent reservoirs.

27. The method of claim 20, further comprising:
recording delivery data to the data storage component of the skin-treatment delivery device, the delivery data including the location on the skin surface of the individual and the one or more treatment agents delivered to said location.

28. The method of claim 27, further comprising:
converting the recorded delivery data into a personalized treatment map including the feature map of the skin surface of the individual overlaid with a two-dimensional distribution of the one or more treatment agents administered at each of one or more locations on the skin surface of the individual.

29. A system for delivering a skin treatment, comprising:
one or more location-capture components including circuitry to measure a feature of a location on a skin surface of an individual;
a treatment unit including one or more treatment agent reservoirs, each of the one or more treatment agent reservoirs including a controllable valve, each of the one or more treatment agent reservoirs configured to store and controllably release one or more treatment agents;

a personalized microbe profile including a feature map of the skin surface of the individual overlaid with a two-dimensional spatial distribution of one or more types of microbes at each of one or more locations on the skin surface of the individual;

a data storage component configured to store information associated with the personalized microbe profile; and a computing device including a processor, the computing device operably coupled to the one or more location-capture components, the treatment unit, and the data storage component, the computing device including circuitry to receive information associated with the measured feature of the location on the skin surface of the individual from the one or more location-capture components;

map the received information associated with the measured feature of the location on the skin surface of the individual to the feature map associated with the personalized microbe profile to determine which of the one or more types of microbes of the personalized microbe profile is associated with said location on the skin surface of the individual;

select at least one of the one or more treatment agents stored in the one or more treatment reservoirs for application to said location on the skin surface of the individual based on which of the one or more types of microbes is associated with said location on the skin surface of the individual; and actuate the controllable valve of at least one of the one or more treatment agent reservoirs to modulate release of the selected at least one of the one or more treatment agents onto said location on the skin surface of the individual.

30. The system of claim 29, wherein the one or more location-capture components comprise at least one of one or more image-capture devices, one or more fiducial readers, or one or more inertial navigation devices.

31. The system of claim 29, wherein the treatment unit and the one or more location-capture components are incorporated into a hand-held unit operably coupled to the computing device through a communications link.

32. The system of claim 29, wherein the computing device, the treatment unit, and the one or more location-capture components are incorporated into a kiosk.

33. The system of claim 29, wherein the feature map of the skin surface of the individual includes at least one of one or more images of the skin surface of the individual, one or more fiducial markers on the skin surface of the individual, or one or more coordinates overlaid with the two-dimensional spatial distribution of the one or more types of microbes at each of the one or more locations on the skin surface of the individual.

34. The system of claim 29, wherein the information associated with the measured feature of the location on the skin surface of the individual comprises at least one of one or more images of the location on the skin surface of the individual, one or more fiducial markers of the location on the skin surface of the individual, or one or more coordinates representative of the location on the skin surface of the individual.

35. The system of claim 29, wherein the computing device includes circuitry to align the measured feature of the location on the skin surface of the individual with a feature on the feature map of the skin surface of the individual overlaid with the personalized microbe profile.

36. The system of claim 29, wherein the computing device includes circuitry to actuate the controllable valve of each of two or more treatment agent reservoirs in a treatment pattern.

37. The system of claim 29, wherein the treatment unit and the one or more location-capture components are incorporated into a walk-in enclosure sized to treat the entirety of the skin surface of the individual, the walk-in enclosure including one or more treatment agent reservoirs.

38. The system of claim 37, wherein at least one of the one or more treatment agent reservoirs of the walk-in enclosure comprises an aimable nozzle in fluid communication with the controllable valve of the at least one of the one or more treatment agent reservoirs.

39. The system of claim 29, wherein the computing device includes circuitry to record delivery data.

40. The system of claim 39, wherein the computing device includes circuitry to convert the recorded delivery data into a personalized treatment map including the feature map of the skin surface of the individual overlaid with a two-dimensional distribution of the one or more treatment agents administered at each of one or more locations on the skin surface of the individual.

41. The system of claim 29, further comprising:

a motivatable portion attached to the treatment unit, the motivatable portion operably coupled to the computing device and including circuitry to autonomously move the treatment unit over the skin surface of the individual to deliver the one or more treatment agents according to the personalized microbe profile.

42. The system of claim 41, wherein at least one of the one or more location-capture components is attached to the motivatable portion.

43. The system of claim 41, wherein the motivatable portion includes circuitry to autonomously move the treatment unit in a pattern over the skin surface of the individual defined by the personalized microbe profile.

* * * * *